(12) United States Patent
Levien et al.

(10) Patent No.: US 9,713,675 B2
(45) Date of Patent: Jul. 25, 2017

(54) UNMANNED DEVICE INTERACTION METHODS AND SYSTEMS

(75) Inventors: Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 210 days.

(21) Appl. No.: 13/601,195

(22) Filed: Aug. 31, 2012

(65) Prior Publication Data
US 2014/0067167 A1 Mar. 6, 2014

Related U.S. Application Data

(63) Continuation-in-part of application No. 13/551,266, filed on Jul. 17, 2012, and a continuation-in-part of (Continued)

(51) Int. Cl.
| G01C 23/00 | (2006.01) |
| A61M 5/20 | (2006.01) |
| G05B 19/00 | (2006.01) |
| G05D 1/00 | (2006.01) |
| G05D 1/02 | (2006.01) |
| A63H 27/00 | (2006.01) |
| G05D 1/10 | (2006.01) |
| G06Q 10/08 | (2012.01) |
| A61M 5/00 | (2006.01) |

(52) U.S. Cl.
CPC ............ *A61M 5/20* (2013.01); *A63H 27/12* (2013.01); *G05B 19/00* (2013.01); *G05D 1/005* (2013.01); *G05D 1/0011* (2013.01); *G05D 1/0027* (2013.01); *G05D 1/0202* (2013.01); *G05D 1/102* (2013.01); *G06Q 10/08* (2013.01); *A61M 5/002* (2013.01)

(58) Field of Classification Search
CPC .... B64C 39/024; B64C 19/00; G05D 1/0044; G05D 1/0088; G05D 1/0094
USPC .............................. 701/2, 3, 11, 23, 24, 124
See application file for complete search history.

(56) References Cited

U.S. PATENT DOCUMENTS

| 4,410,151 A | 10/1983 | Hoppner et al. |
| 5,521,817 A | 5/1996 | Burdoin et al. |

(Continued)

FOREIGN PATENT DOCUMENTS

| CN | 102120489 A | 7/2011 |
| JP | 2008/180100 | 6/2000 |

(Continued)

OTHER PUBLICATIONS

Fischer, Markus; "A robot that flies like a bird" Online Video Clip; TED Conferences, LLC; Jul. 2011; accessed on Sep. 11, 2012; located at http://www.ted.com/talks/a_robot_that_flies_like_a_bird.html.

(Continued)

*Primary Examiner* — Shardul Patel

(57) ABSTRACT

Structures and protocols are presented for configuring an unmanned aerial device to participate in the performance of tasks, for using data resulting from such a configuration or performance, or for facilitating other interactions with such devices.

34 Claims, 35 Drawing Sheets

Related U.S. Application Data application No. 13/551,287, filed on Jul. 17, 2012, and a continuation-in-part of application No. 13/551,301, filed on Jul. 17, 2012, and a continuation-in-part of application No. 13/551,320, filed on Jul. 17, 2012, and a continuation-in-part of application No. 13/551,334, filed on Jul. 17, 2012, and a continuation-in-part of application No. 13/601,060, filed on Aug. 31, 2012, and a continuation-in-part of application No. 13/601,082, filed on Aug. 31, 2012, and a continuation-in-part of application No. 13/601,096, filed on Aug. 31, 2012, and a continuation-in-part of application No. 13/601,112, filed on Aug. 31, 2012, and a continuation-in-part of application No. 13/601,140, filed on Aug. 31, 2012, and a continuation-in-part of application No. 13/601,169, filed on Aug. 31, 2012.

(56) References Cited

U.S. PATENT DOCUMENTS

| | | |
|---|---|---|
| 5,615,847 A | 4/1997 | Bourlett |
| 5,695,153 A | 12/1997 | Britton et al. |
| 5,798,733 A | 8/1998 | Ethridge |
| 6,009,409 A | 12/1999 | Adler et al. |
| 6,033,316 A | 3/2000 | Nixon |
| 6,034,361 A | 3/2000 | Hudak |
| 6,052,682 A | 4/2000 | Miller et al. |
| 6,055,523 A | 4/2000 | Hillis |
| 6,058,312 A | 5/2000 | Kimura |
| 6,084,827 A | 7/2000 | Johnson et al. |
| 6,091,738 A | 7/2000 | Tsujikado et al. |
| 6,114,950 A | 9/2000 | Schaible et al. |
| 6,114,970 A | 9/2000 | Kirson et al. |
| 6,121,916 A | 9/2000 | McDade |
| 6,133,867 A | 10/2000 | Eberwine et al. |
| 6,163,745 A | 12/2000 | Purchase et al. |
| 6,167,186 A | 12/2000 | Kawasaki et al. |
| 6,176,451 B1 | 1/2001 | Drymon |
| 6,219,639 B1 | 4/2001 | Bakis et al. |
| 6,238,290 B1 | 5/2001 | Tarr et al. |
| 6,283,227 B1 | 9/2001 | Lerche et al. |
| 6,313,745 B1 | 11/2001 | Suzuki |
| 6,333,718 B1 | 12/2001 | Poncel et al. |
| 6,335,910 B1 | 1/2002 | Yoshizawa et al. |
| 6,356,196 B1 | 3/2002 | Wong et al. |
| 6,373,982 B1 | 4/2002 | Maier et al. |
| 6,374,182 B2 | 4/2002 | Bechtolsheim et al. |
| 6,377,875 B1 | 4/2002 | Schwaerzler |
| 6,400,304 B1 | 6/2002 | Chubbs, III |
| 6,430,182 B1 | 8/2002 | Oyama |
| 6,459,935 B1 | 10/2002 | Piersma |
| 6,463,354 B1 | 10/2002 | Pintsov |
| 6,463,420 B1 | 10/2002 | Guidice et al. |
| 6,470,989 B1 | 10/2002 | Puputti et al. |
| 6,473,824 B1 | 10/2002 | Kreissig et al. |
| 6,493,581 B2 | 12/2002 | Russell |
| 6,497,600 B1 | 12/2002 | Levy et al. |
| 6,513,015 B2 | 1/2003 | Ogasawara |
| 6,526,377 B1 | 2/2003 | Bubb |
| 6,535,585 B1 | 3/2003 | Hanson et al. |
| 6,538,581 B2 | 3/2003 | Cowie |
| 6,552,669 B2 | 4/2003 | Simon et al. |
| 6,569,690 B1 | 5/2003 | Houge et al. |
| 6,574,538 B2 | 6/2003 | Sasaki |
| 6,577,976 B1 | 6/2003 | Hoff et al. |
| 6,578,085 B1 | 6/2003 | Khalil et al. |
| 6,591,101 B1 | 7/2003 | Shimbori |
| 6,592,033 B2 | 7/2003 | Jennings et al. |
| 6,604,038 B1 | 8/2003 | Lesesky et al. |
| 6,604,044 B1 | 8/2003 | Kirk |
| 6,604,124 B1 | 8/2003 | Archbold |
| 6,609,317 B2 | 8/2003 | Myers |
| 6,669,653 B2 | 12/2003 | Paltieli |
| 6,692,449 B1 | 2/2004 | Brown |
| 6,694,177 B2 | 2/2004 | Eggers et al. |
| 6,694,228 B2 | 2/2004 | Rios |
| 6,711,555 B1 | 3/2004 | Sanders |
| 6,721,640 B2 | 4/2004 | Glenn et al. |
| 6,721,761 B2 | 4/2004 | Nagy et al. |
| 6,734,799 B2 | 5/2004 | Munch |
| 6,735,444 B2 | 5/2004 | Wingren |
| 6,742,037 B1 | 5/2004 | Hall et al. |
| 6,798,867 B1 | 9/2004 | Zirngibl et al. |
| 6,801,139 B2 | 10/2004 | Tretyak, Jr. |
| 6,826,534 B1 | 11/2004 | Gupta et al. |
| 6,847,856 B1 | 1/2005 | Bohannon |
| 6,847,865 B2 | 1/2005 | Carroll |
| 6,856,894 B1 | 2/2005 | Bodin et al. |
| 6,859,722 B2 | 2/2005 | Jones |
| 6,892,135 B1 | 5/2005 | Krull et al. |
| 6,901,330 B1 | 5/2005 | Krull et al. |
| 6,902,109 B2 | 6/2005 | Barta et al. |
| 6,917,863 B2 | 7/2005 | Matos |
| 6,923,404 B1 | 8/2005 | Liu et al. |
| 6,926,233 B1 | 8/2005 | Corcoran, III |
| 6,931,596 B2 | 8/2005 | Gutta et al. |
| 6,942,369 B2 | 9/2005 | Le Bars et al. |
| 6,963,279 B1 | 11/2005 | Martinelli et al. |
| 6,965,816 B2 | 11/2005 | Walker |
| 6,975,820 B2 | 12/2005 | Wong |
| 6,985,206 B2 | 1/2006 | Anderson et al. |
| 6,985,871 B2 | 1/2006 | Simon et al. |
| 6,991,304 B2 | 1/2006 | Villaume |
| 6,999,876 B2 | 2/2006 | Lambert et al. |
| 7,006,013 B2 | 2/2006 | Mitchell et al. |
| 7,010,098 B2 | 3/2006 | Moquin et al. |
| 7,013,350 B2 | 3/2006 | Enns et al. |
| 7,027,808 B2 | 4/2006 | Wesby |
| 7,029,031 B2 | 4/2006 | Moisel et al. |
| 7,035,856 B1 | 4/2006 | Morimoto |
| 7,092,566 B2 | 8/2006 | Krumm |
| 7,093,294 B2 | 8/2006 | Lingafelt et al. |
| 7,107,064 B2 | 9/2006 | Ito |
| 7,127,334 B2 | 10/2006 | Frink |
| 7,130,741 B2 | 10/2006 | Bodin et al. |
| 7,142,110 B2 | 11/2006 | Schmidtberg et al. |
| 7,143,937 B2 | 12/2006 | Rainey et al. |
| 7,154,275 B2 | 12/2006 | Zank et al. |
| 7,174,305 B2 | 2/2007 | Carruthers et al. |
| 7,177,948 B1 | 2/2007 | Kraft et al. |
| 7,222,081 B1 * | 5/2007 | Sone ............... G06Q 10/08 705/333 |
| 7,225,983 B2 | 6/2007 | Park et al. |
| 7,228,232 B2 | 6/2007 | Bodin et al. |
| 7,233,907 B2 | 6/2007 | Young |
| 7,240,075 B1 | 7/2007 | Nemirofsky et al. |
| 7,242,462 B2 | 7/2007 | Huang |
| 7,245,702 B1 | 7/2007 | Mahaney |
| 7,252,453 B1 | 8/2007 | Little |
| 7,262,730 B2 | 8/2007 | Larsson et al. |
| 7,280,696 B2 | 10/2007 | Zakrzewski et al. |
| 7,289,184 B2 | 10/2007 | Hirakata |
| 7,290,005 B2 | 10/2007 | Corston-Oliver et al. |
| 7,295,106 B1 | 11/2007 | Jackson et al. |
| 7,308,472 B2 | 12/2007 | Hasegawa |
| 7,315,548 B2 | 1/2008 | Joshi |
| 7,331,019 B2 | 2/2008 | Ananth et al. |
| 7,340,283 B1 | 3/2008 | Melick et al. |
| 7,346,188 B2 | 3/2008 | Aichi |
| 7,346,662 B2 | 3/2008 | Koch et al. |
| 7,346,675 B2 | 3/2008 | Givoly et al. |
| 7,359,346 B2 | 4/2008 | Kim |
| 7,361,183 B2 | 4/2008 | Ginn |
| 7,363,246 B1 | 4/2008 | Van Horn et al. |
| 7,370,078 B1 | 5/2008 | Woodruff |
| 7,383,174 B2 | 6/2008 | Paulin |
| 7,392,151 B2 | 6/2008 | Makela |
| 7,394,817 B2 | 7/2008 | Yap |
| 7,401,030 B1 | 7/2008 | Mather et al. |
| 7,406,515 B1 | 7/2008 | Joyce et al. |
| 7,431,243 B1 | 10/2008 | Allen |
| 7,437,305 B1 | 10/2008 | Kantarjiev et al. |
| 7,451,445 B1 | 11/2008 | Eppstein |

(56) References Cited

U.S. PATENT DOCUMENTS

| | | |
|---|---|---|
| 7,460,052 B2 | 12/2008 | Zemany et al. |
| 7,467,122 B2 | 12/2008 | Morita et al. |
| 7,474,212 B2 | 1/2009 | Nakagawa et al. |
| 7,476,796 B2 | 1/2009 | Iwase et al. |
| 7,477,993 B2 | 1/2009 | Sunshine et al. |
| 7,480,394 B2 | 1/2009 | Berlin et al. |
| 7,483,721 B1 | 1/2009 | Vesikivi |
| 7,492,926 B2 | 2/2009 | Kang |
| 7,494,464 B2 | 2/2009 | Rzesnitzek et al. |
| 7,495,576 B2 | 2/2009 | Maskeny et al. |
| 7,496,670 B1 | 2/2009 | Givoly |
| 7,502,684 B2 | 3/2009 | Haas |
| 7,516,082 B2 | 4/2009 | Sanville et al. |
| 7,532,896 B2 | 5/2009 | Friday et al. |
| 7,548,866 B2 | 6/2009 | Halavais et al. |
| 7,549,204 B1 | 6/2009 | Vangal-Ramamurthy et al. |
| 7,555,386 B2 | 6/2009 | Song |
| 7,559,456 B1 | 7/2009 | McKenzie |
| 7,571,101 B2 | 8/2009 | Humble |
| 7,574,077 B2 | 8/2009 | Zheng et al. |
| 7,581,702 B2 | 9/2009 | Olson et al. |
| 7,587,369 B2 | 9/2009 | Ginter et al. |
| 7,592,945 B2 | 9/2009 | Colburn et al. |
| 7,593,982 B2 | 9/2009 | Busey |
| 7,596,241 B2 | 9/2009 | Rittscher et al. |
| 7,596,248 B2 | 9/2009 | Cova et al. |
| 7,598,888 B2 | 10/2009 | Matuska et al. |
| 7,610,122 B2 | 10/2009 | Anderson |
| 7,610,213 B2 | 10/2009 | Jones et al. |
| 7,617,024 B2 | 11/2009 | Builta |
| 7,627,577 B1 | 12/2009 | Lee et al. |
| 7,630,806 B2 | 12/2009 | Breed |
| 7,631,065 B2 | 12/2009 | Schweitzer et al. |
| 7,631,834 B1 | 12/2009 | Johnson et al. |
| 7,634,426 B2 | 12/2009 | Craw et al. |
| 7,636,669 B1 | 12/2009 | Bergert |
| 7,636,687 B2 | 12/2009 | Foster et al. |
| 7,641,461 B2 | 1/2010 | Khoshnevis |
| 7,643,686 B2 | 1/2010 | Kraus et al. |
| 7,647,049 B2 | 1/2010 | Engdahl et al. |
| 7,647,171 B2 | 1/2010 | Horvitz et al. |
| 7,647,230 B2 | 1/2010 | Lee et al. |
| 7,647,232 B2 | 1/2010 | Moitra et al. |
| 7,647,875 B2 | 1/2010 | Landphair et al. |
| 7,648,513 B2 | 1/2010 | Green et al. |
| 7,653,697 B2 | 1/2010 | Isaacs et al. |
| 7,656,292 B2 | 2/2010 | Bartholf et al. |
| 7,658,156 B2 | 2/2010 | Wold et al. |
| 7,659,835 B2 | 2/2010 | Jung |
| 7,665,092 B1 | 2/2010 | Vengerov |
| 7,669,805 B2 | 3/2010 | Hors et al. |
| 7,670,329 B2 | 3/2010 | Flaherty et al. |
| 7,671,795 B2 | 3/2010 | Rofougaran |
| 7,680,691 B2 | 3/2010 | Kimball et al. |
| 7,693,565 B2 | 4/2010 | Shai et al. |
| 7,693,779 B2 | 4/2010 | Avery |
| 7,703,691 B2 | 4/2010 | Patel et al. |
| 7,705,714 B2 | 4/2010 | Mori |
| 7,713,229 B2 | 5/2010 | Veit et al. |
| 7,716,378 B2 | 5/2010 | Chen et al. |
| 7,716,667 B2 | 5/2010 | van Rietschote et al. |
| 7,717,255 B2 | 5/2010 | Scott et al. |
| 7,720,554 B2 | 5/2010 | DiBernardo et al. |
| 7,725,232 B2 | 5/2010 | Makela et al. |
| 7,733,214 B2 | 6/2010 | Sarig et al. |
| 7,733,223 B2 | 6/2010 | Levien et al. |
| 7,735,631 B2 | 6/2010 | Berdelle-Hilge |
| 7,737,878 B2 | 6/2010 | van Tooren et al. |
| 7,739,096 B2 | 6/2010 | Wegerich et al. |
| 7,739,157 B2 | 6/2010 | Bonner et al. |
| 7,739,202 B2 | 6/2010 | Kadaba |
| 7,743,051 B1 | 6/2010 | Kashyap et al. |
| 7,743,099 B2 | 6/2010 | Szeto |
| 7,750,778 B2 | 7/2010 | Fullerton et al. |
| 7,756,822 B2 | 7/2010 | Danner et al. |
| 7,761,480 B2 | 7/2010 | Toledano et al. |
| 7,764,179 B1 | 7/2010 | Strawder |
| 7,769,644 B2 | 8/2010 | Naghshineh et al. |
| 7,769,984 B2 | 8/2010 | Alexander et al. |
| 7,774,719 B2 | 8/2010 | Taylor |
| 7,775,329 B2 | 8/2010 | Eckenstein et al. |
| 7,778,792 B2 | 8/2010 | Huang et al. |
| 7,782,365 B2 | 8/2010 | Levien et al. |
| 7,783,506 B2 | 8/2010 | Vaughan et al. |
| 7,783,530 B2 | 8/2010 | Slemmer et al. |
| 7,784,946 B2 | 8/2010 | LeBlanc |
| 7,787,663 B2 | 8/2010 | Hartlove |
| 7,787,870 B2 | 8/2010 | Burgan et al. |
| 7,787,998 B2 | 8/2010 | Foucart et al. |
| 7,792,808 B2 | 9/2010 | Stuart et al. |
| 7,792,837 B1 | 9/2010 | Zhao |
| 7,797,077 B2 | 9/2010 | Hale |
| 7,805,306 B2 | 9/2010 | Mitsui |
| 7,806,371 B2 | 10/2010 | Troutman |
| 7,809,163 B2 | 10/2010 | Sheu |
| 7,818,190 B1 | 10/2010 | Sutherland |
| 7,819,315 B1 | 10/2010 | Pienkos |
| 7,822,463 B2 | 10/2010 | Meron et al. |
| 7,822,988 B2 | 10/2010 | Cameron et al. |
| 7,825,815 B2 | 11/2010 | Shears et al. |
| 7,835,971 B2 | 11/2010 | Stockton et al. |
| 7,836,186 B2 | 11/2010 | Lanahan et al. |
| 7,837,143 B2 | 11/2010 | Matos |
| 7,839,526 B2 | 11/2010 | Sato et al. |
| 7,840,346 B2 | 11/2010 | Huhtala et al. |
| 7,864,702 B2 | 1/2011 | Shah et al. |
| 7,865,186 B2 | 1/2011 | Kim et al. |
| 7,865,212 B2 | 1/2011 | Tysowski |
| 7,865,277 B1 | 1/2011 | Larson et al. |
| 7,865,356 B2 | 1/2011 | Weng et al. |
| 7,865,409 B1 | 1/2011 | Monaghan |
| 7,868,264 B2 | 1/2011 | Stemmle et al. |
| 7,869,444 B2 | 1/2011 | Menard et al. |
| 7,869,562 B2 | 1/2011 | Khamene et al. |
| 7,870,012 B2 | 1/2011 | Katz et al. |
| 7,870,117 B1 | 1/2011 | Rennison |
| 7,876,215 B1 | 1/2011 | Brady, Jr. |
| 7,877,515 B2 | 1/2011 | Andersson et al. |
| 7,881,497 B2 | 2/2011 | Ganguli et al. |
| 7,881,864 B2 | 2/2011 | Smith |
| 7,883,013 B2 | 2/2011 | Skaaksrud et al. |
| 7,885,222 B2 | 2/2011 | Cole |
| 7,889,913 B2 | 2/2011 | Wells |
| 7,890,221 B2 | 2/2011 | Kossentini |
| 7,893,848 B2 | 2/2011 | Chew |
| 7,893,960 B1 | 2/2011 | Wallach |
| 7,894,812 B1 | 2/2011 | Durig et al. |
| 7,895,013 B2 | 2/2011 | Dietz et al. |
| 7,899,027 B2 | 3/2011 | Castagnoli et al. |
| 7,899,617 B2 | 3/2011 | Kawakami et al. |
| 7,903,839 B2 | 3/2011 | Cresens |
| 7,908,221 B2 | 3/2011 | Bodmer et al. |
| 7,913,370 B2 | 3/2011 | Savoy |
| 7,916,066 B1 | 3/2011 | Osterweil |
| 7,917,514 B2 | 3/2011 | Lawler et al. |
| 7,919,060 B2 | 4/2011 | Funke et al. |
| 7,920,678 B2 | 4/2011 | Cooper et al. |
| 7,922,088 B2 | 4/2011 | Wang |
| 7,925,093 B2 | 4/2011 | Ikeda et al. |
| 7,929,559 B2 | 4/2011 | Hao |
| 7,931,238 B2 | 4/2011 | Builta et al. |
| 7,934,267 B2 | 5/2011 | Nordstrom et al. |
| 7,941,354 B2 | 5/2011 | Breen |
| 7,941,505 B2 | 5/2011 | Jaye |
| 7,945,470 B1 | 5/2011 | Cohen et al. |
| 7,947,916 B2 | 5/2011 | Stemmle |
| 7,947,936 B2 | 5/2011 | Bobinchak et al. |
| 7,948,447 B2 | 5/2011 | Weis et al. |
| 7,949,089 B2 | 5/2011 | Dafni et al. |
| 7,951,046 B1 | 5/2011 | Barber, Jr. |
| 7,953,806 B2 | 5/2011 | Lyle et al. |
| 7,956,769 B1 | 6/2011 | Pearl |
| 7,962,252 B2 | 6/2011 | Shams et al. |
| 7,962,254 B2 | 6/2011 | Bouchet et al. |

(56) References Cited

U.S. PATENT DOCUMENTS

| | | | |
|---|---|---|---|
| 7,962,283 B2 | 6/2011 | Zhang et al. |
| 7,969,922 B2 | 6/2011 | Fok et al. |
| 7,970,426 B2 | 6/2011 | Poe et al. |
| 7,970,539 B2 | 6/2011 | Lee |
| 7,970,660 B2 | 6/2011 | Bezos et al. |
| 7,970,735 B2 | 6/2011 | D'Hers et al. |
| 7,978,065 B2 | 7/2011 | Schnitz et al. |
| 7,978,084 B2 | 7/2011 | Dixon et al. |
| 7,979,309 B1 | 7/2011 | Stevens et al. |
| 7,979,585 B2 | 7/2011 | Chen et al. |
| 7,983,447 B2 | 7/2011 | Higuchi et al. |
| 7,983,759 B2 | 7/2011 | Stahmann et al. |
| 7,984,100 B1 | 7/2011 | King et al. |
| 7,995,731 B2 | 8/2011 | Vernick |
| 7,996,658 B2 | 8/2011 | Nagao et al. |
| 7,996,893 B2 | 8/2011 | Persaud-Deolall et al. |
| 8,004,563 B2 | 8/2011 | Talmon et al. |
| 8,006,194 B2 | 8/2011 | Berger et al. |
| 8,009,058 B2 | 8/2011 | Lehmann et al. |
| 8,014,917 B2 | 9/2011 | Hagenbuch |
| 8,014,974 B2 | 9/2011 | Doddek et al. |
| 8,019,283 B2 | 9/2011 | Eisenbach |
| 8,019,771 B2 | 9/2011 | Iwao |
| 8,023,485 B2 | 9/2011 | Shi et al. |
| 8,023,695 B2 | 9/2011 | Rhoads |
| 8,024,138 B2 | 9/2011 | Carroll et al. |
| 8,024,329 B1 | 9/2011 | Rennison |
| 8,026,850 B2 | 9/2011 | Seong et al. |
| 8,027,761 B1 | 9/2011 | Nelson |
| 8,029,228 B2 | 10/2011 | Marmur |
| 8,032,153 B2 | 10/2011 | Dupray et al. |
| 8,036,891 B2 | 10/2011 | Fulop |
| 8,037,839 B2 | 10/2011 | Thistle |
| 8,040,245 B2 | 10/2011 | Koblasz |
| 8,040,864 B2 | 10/2011 | Karaoguz et al. |
| 8,041,453 B2 | 10/2011 | Walker et al. |
| 8,041,649 B2 | 10/2011 | Mougey et al. |
| 8,041,664 B1 | 10/2011 | Lambert |
| 8,044,798 B2 | 10/2011 | Icove et al. |
| 8,050,243 B2 | 11/2011 | Ostergren |
| 8,051,429 B2 | 11/2011 | Williamson et al. |
| 8,051,764 B2 | 11/2011 | Jacobsen et al. |
| 8,061,842 B2 | 11/2011 | Czajka et al. |
| 8,064,647 B2 | 11/2011 | Bazakos et al. |
| 8,065,287 B2 | 11/2011 | Heyraud et al. |
| 8,066,460 B2 | 11/2011 | Brierton |
| 8,068,802 B2 | 11/2011 | Bhattacharya et al. |
| 8,074,642 B2 | 12/2011 | Bruce et al. |
| 8,074,941 B2 | 12/2011 | Daunois et al. |
| 8,078,107 B2 | 12/2011 | Eisenbach |
| 8,078,395 B2 | 12/2011 | Builta et al. |
| 8,081,967 B2 | 12/2011 | Stephens |
| 8,087,019 B1 | 12/2011 | Sobotka et al. |
| 8,090,132 B2 | 1/2012 | Tang et al. |
| 8,090,525 B2 | 1/2012 | Villiers |
| 8,090,526 B2 | 1/2012 | Marty et al. |
| 8,090,826 B2 | 1/2012 | Tran et al. |
| 8,091,463 B1 | 1/2012 | Moody |
| 8,094,009 B2 | 1/2012 | Allen et al. |
| 8,095,612 B2 | 1/2012 | Cowan et al. |
| 8,098,142 B2 | 1/2012 | Schofield et al. |
| 8,099,060 B2 | 1/2012 | Kirkup et al. |
| 8,099,339 B1 | 1/2012 | Pinsonneault et al. |
| 8,100,366 B2 | 1/2012 | Milanese et al. |
| 8,101,434 B2 | 1/2012 | Guillien et al. |
| 8,106,746 B2 | 1/2012 | Maltseff et al. |
| 8,107,608 B2 | 1/2012 | Sheha et al. |
| 8,108,083 B2 | 1/2012 | Kameyama |
| 8,108,091 B2 | 1/2012 | Chou et al. |
| 8,109,891 B2 | 2/2012 | Kramer et al. |
| 8,111,819 B2 | 2/2012 | Zegers |
| 8,112,475 B2 | 2/2012 | Tran et al. |
| 8,115,625 B2 | 2/2012 | Yoshioka et al. |
| 8,117,051 B2 | 2/2012 | Sauvage et al. |
| 8,121,083 B2 | 2/2012 | Wen et al. |
| 8,122,365 B2 | 2/2012 | Padmanabhuni et al. |
| 8,122,982 B2 | 2/2012 | Morey et al. |
| 8,127,233 B2 | 2/2012 | McDowell |
| 8,127,300 B2 | 2/2012 | Arimilli et al. |
| 8,128,026 B2 | 3/2012 | Shelton |
| 8,128,484 B2 | 3/2012 | Okada |
| 8,131,540 B2 | 3/2012 | Marchisio et al. |
| 8,131,652 B2 | 3/2012 | Gullo et al. |
| 8,131,745 B1 | 3/2012 | Hoffman et al. |
| 8,135,171 B2 | 3/2012 | Ho et al. |
| 8,135,708 B2 | 3/2012 | Morton |
| 8,135,764 B2 | 3/2012 | Iizuka et al. |
| 8,135,957 B2 | 3/2012 | Dinges et al. |
| 8,136,025 B1 | 3/2012 | Zhu et al. |
| 8,138,976 B2 | 3/2012 | Boyer et al. |
| 8,140,592 B2 | 3/2012 | Scott et al. |
| 8,141,814 B2 | 3/2012 | Kulesha |
| 8,144,881 B2 | 3/2012 | Crockett et al. |
| 8,145,199 B2 | 3/2012 | Tadayon et al. |
| 8,149,288 B2 | 4/2012 | Nakagomi et al. |
| 8,150,403 B2 | 4/2012 | Mock et al. |
| 8,151,201 B2 | 4/2012 | Sibley et al. |
| 8,151,272 B2 | 4/2012 | Sundaresan et al. |
| 8,155,805 B2 | 4/2012 | Spek |
| 8,156,542 B2 | 4/2012 | Huotari et al. |
| 8,160,615 B1 | 4/2012 | Barnes et al. |
| 8,160,906 B2 | 4/2012 | Smith et al. |
| 8,164,302 B2 | 4/2012 | Capizzo |
| 8,164,461 B2 | 4/2012 | Bischoff |
| 8,165,567 B2 | 4/2012 | Kim et al. |
| 8,165,932 B2 | 4/2012 | Schweitzer et al. |
| 8,166,484 B2 | 4/2012 | Kawato |
| 8,167,236 B2 | 5/2012 | Jess |
| 8,167,786 B2 | 5/2012 | Chu et al. |
| 8,170,532 B2 | 5/2012 | Wan et al. |
| 8,170,798 B2 | 5/2012 | Arita |
| 8,171,318 B2 | 5/2012 | Cornwell et al. |
| 8,171,394 B2 | 5/2012 | Taylor et al. |
| 8,171,460 B2 | 5/2012 | Pizzoli et al. |
| 8,171,474 B2 | 5/2012 | Mankovski |
| 8,171,567 B1 | 5/2012 | Fraser et al. |
| 8,172,459 B2 | 5/2012 | Abreu |
| 8,175,025 B2 | 5/2012 | Yanagihara |
| 8,176,156 B1 | 5/2012 | Sullivan |
| 8,179,253 B2 | 5/2012 | Zaruba et al. |
| 8,179,261 B2 | 5/2012 | Frabasile |
| 8,179,287 B2 | 5/2012 | Kato et al. |
| 8,179,496 B2 | 5/2012 | Liou et al. |
| 8,180,107 B2 | 5/2012 | Broaddus et al. |
| 8,180,827 B2 | 5/2012 | Lim |
| 8,181,119 B1 | 5/2012 | Ording |
| 8,181,168 B1 | 5/2012 | Lee et al. |
| 8,184,070 B1 | 5/2012 | Taubman |
| 8,184,860 B2 | 5/2012 | Muramatsu et al. |
| 8,184,914 B2 | 5/2012 | Kyyko et al. |
| 8,185,483 B2 | 5/2012 | Buendia et al. |
| 8,185,536 B2 | 5/2012 | Basu et al. |
| 8,186,589 B2 | 5/2012 | Ben Asher et al. |
| 8,192,698 B2 | 6/2012 | Londo et al. |
| 8,194,975 B2 | 6/2012 | Smith |
| 8,196,809 B2 | 6/2012 | Thorstensson |
| 8,198,568 B2 | 6/2012 | Klinghult |
| 8,200,084 B2 | 6/2012 | Bernstein et al. |
| 8,200,223 B2 | 6/2012 | Harada et al. |
| 8,200,247 B1 | 6/2012 | Starenky et al. |
| 8,200,491 B2 | 6/2012 | Gorin et al. |
| 8,200,583 B1 | 6/2012 | Adkins, III et al. |
| 8,201,143 B2 | 6/2012 | Reamey |
| 8,203,426 B1 | 6/2012 | Hirschfeld et al. |
| 8,204,770 B2 | 6/2012 | Sussman et al. |
| 8,207,869 B1 | 6/2012 | Judd et al. |
| 8,209,171 B2 | 6/2012 | Abbott et al. |
| 8,209,278 B1 | 6/2012 | Straus |
| 8,211,035 B2 | 7/2012 | Melker et al. |
| 8,219,116 B1 | 7/2012 | Ji et al. |
| 8,219,312 B2 | 7/2012 | Davidson et al. |
| 8,219,572 B2 | 7/2012 | Ghosh et al. |
| 8,224,508 B2 | 7/2012 | Bacabara et al. |
| 8,229,163 B2 | 7/2012 | Coleman et al. |

(56) References Cited

U.S. PATENT DOCUMENTS

| | | |
|---|---|---|
| 8,353,199 B1 | 1/2013 | Ma et al. |
| 8,565,913 B2 | 10/2013 | Emanuel et al. |
| 8,639,396 B1 | 1/2014 | Hirsch et al. |
| 8,688,598 B1 | 4/2014 | Shakes et al. |
| 8,930,044 B1 | 1/2015 | Peeters et al. |
| 8,948,935 B1 | 2/2015 | Peeters et al. |
| 8,983,682 B1 | 3/2015 | Peeters et al. |
| 9,022,324 B1 | 5/2015 | Abhyanker |
| 2003/0200726 A1 | 10/2003 | Rast |
| 2004/0134336 A1 | 7/2004 | Solomon |
| 2004/0143602 A1 | 7/2004 | Ruiz et al. |
| 2004/0233414 A1 | 11/2004 | Jamieson et al. |
| 2005/0093507 A1 | 5/2005 | Sliwa et al. |
| 2005/0139363 A1 | 6/2005 | Thomas |
| 2006/0139598 A1 | 6/2006 | Van Dijsseldonk et al. |
| 2006/0167596 A1* | 7/2006 | Bodin .......... G05D 1/0027 701/3 |
| 2006/0197835 A1* | 9/2006 | Anderson ......... H04N 7/183 348/117 |
| 2006/0221328 A1 | 10/2006 | Rouly |
| 2006/0249622 A1 | 11/2006 | Steele |
| 2007/0021880 A1 | 1/2007 | Appleby et al. |
| 2007/0061041 A1 | 3/2007 | Zweig |
| 2007/0152099 A1 | 7/2007 | Moreau |
| 2007/0152619 A1 | 7/2007 | Sugiyama et al. |
| 2007/0180318 A1 | 8/2007 | Morozumi |
| 2007/0192910 A1 | 8/2007 | Vu et al. |
| 2007/0225993 A1* | 9/2007 | Moore ............ G06Q 10/02 705/5 |
| 2008/0159622 A1 | 7/2008 | Agnihotri et al. |
| 2008/0185526 A1* | 8/2008 | Horak ............. G01J 5/08 250/353 |
| 2008/0190274 A1 | 8/2008 | Kirkpatrick |
| 2009/0008499 A1 | 1/2009 | Shaw |
| 2009/0050750 A1 | 2/2009 | Goossen |
| 2009/0055019 A1 | 2/2009 | Stiehl et al. |
| 2009/0198371 A1 | 8/2009 | Emanuel et al. |
| 2009/0207048 A1* | 8/2009 | He ................. G01C 23/00 340/973 |
| 2009/0232355 A1 | 9/2009 | Minear et al. |
| 2009/0243855 A1 | 10/2009 | Prokopuk |
| 2009/0299551 A1 | 12/2009 | So et al. |
| 2009/0322877 A1* | 12/2009 | Tigner ............. H04N 7/18 348/144 |
| 2010/0004798 A1* | 1/2010 | Bodin ............. G01S 19/14 701/2 |
| 2010/0084513 A1* | 4/2010 | Gariepy ........... B64C 39/024 244/190 |
| 2010/0174546 A1 | 7/2010 | Kim et al. |
| 2010/0198514 A1 | 8/2010 | Miralles |
| 2010/0224732 A1 | 9/2010 | Olson et al. |
| 2010/0250022 A1 | 9/2010 | Hines et al. |
| 2010/0252690 A1 | 10/2010 | Hothi et al. |
| 2010/0253594 A1 | 10/2010 | Szczerba et al. |
| 2011/0049288 A1 | 3/2011 | Suzuki |
| 2011/0049290 A1 | 3/2011 | Seydoux et al. |
| 2011/0081053 A1* | 4/2011 | Zheng ............. G06K 9/6247 382/118 |
| 2011/0084162 A1* | 4/2011 | Goossen ........... B64C 39/024 244/12.1 |
| 2011/0093361 A1 | 4/2011 | Morales |
| 2011/0102197 A1 | 5/2011 | Herwich |
| 2011/0139928 A1 | 6/2011 | Morris et al. |
| 2011/0221692 A1 | 9/2011 | Seydoux et al. |
| 2011/0288696 A1 | 11/2011 | Lefebure |
| 2012/0022719 A1 | 1/2012 | Matos |
| 2012/0091260 A1 | 4/2012 | Callou |
| 2012/0101632 A1 | 4/2012 | Ha et al. |
| 2012/0152654 A1 | 6/2012 | Marcus |
| 2012/0200703 A1 | 8/2012 | Nadir et al. |
| 2012/0210853 A1 | 8/2012 | Abershitz et al. |
| 2012/0215382 A1* | 8/2012 | Lee ............. G05D 1/0033 701/2 |
| 2012/0224732 A1* | 9/2012 | Secall ............ H04R 25/43 381/315 |
| 2012/0226394 A1 | 9/2012 | Marcus |
| 2012/0271491 A1* | 10/2012 | Spata ............. G01W 1/00 701/3 |
| 2012/0290152 A1 | 11/2012 | Cheung et al. |
| 2012/0304085 A1* | 11/2012 | Kim ............. G08B 13/19671 715/763 |
| 2012/0309288 A1 | 12/2012 | Lu |
| 2012/0320510 A1 | 12/2012 | Varga et al. |
| 2013/0006675 A1 | 1/2013 | Bowne et al. |
| 2013/0206921 A1 | 8/2013 | Paduano et al. |
| 2013/0238170 A1 | 9/2013 | Klinger |
| 2013/0314502 A1 | 11/2013 | Urbach et al. |
| 2014/0032021 A1* | 1/2014 | Metzler ......... G01S 5/0036 701/3 |
| 2014/0032034 A1 | 1/2014 | Raptopoulos et al. |
| 2014/0058786 A1 | 2/2014 | Marquet |
| 2014/0152017 A1 | 6/2014 | Bhusri |
| 2014/0172727 A1 | 6/2014 | Abhyanker et al. |
| 2014/0188776 A1 | 7/2014 | Shuster et al. |
| 2014/0263851 A1 | 9/2014 | Hine et al. |
| 2014/0316614 A1 | 10/2014 | Newman |
| 2014/0347482 A1* | 11/2014 | Weinmann ........ H04N 5/247 348/144 |
| 2015/0093956 A1 | 4/2015 | Mielniczek |
| 2015/0095882 A1 | 4/2015 | Jaeger et al. |
| 2015/0120094 A1 | 4/2015 | Kimchi et al. |
| 2015/0120126 A1 | 4/2015 | So et al. |
| 2015/0143806 A1 | 5/2015 | Friesth |
| 2016/0313734 A1 | 10/2016 | Enke |

FOREIGN PATENT DOCUMENTS

| | | |
|---|---|---|
| KR | 101339183 B1 | 12/2013 |
| NL | 1032982 C2 | 4/2008 |
| WO | WO 2005/076967 A2 | 8/2005 |
| WO | WO/2012/047977 | 4/2012 |
| WO | WO 2012/047977 A1 | 12/2012 |

OTHER PUBLICATIONS

Kumar, Vijay; "Robots that fly . . . and cooperate" Online Video Clip; TED Conferences, LLC; Feb. 2012; accessed on Sep. 11, 2012; located at http://www.ted.com/talks/vijay_kumar_robots_that_fly_and_cooperate.html.

Lermusiaux, Pierre; "Optimal paths for automated underwater vehicles (AUVs)" Online Video Clip; MITNewsOffice; published on Mar. 8, 2012; accessed on Sep. 11, 2012; located at http://www.youtube.com/watch?v=OtnOgefsm0w; also located at http://www.engadget.com/2012/03/12/mit-software-optimizes-paths-for-automated-undersea-vehicles/.

Song, Yale; "Guiding robot planes with hand gestures" Online Video Clip; MITNewsOffice; published on Mar. 13, 2012; accessed on Sep. 11, 2012; located at http://www.youtube.com/watch?v=VjVmLA8_uHY; also located at http://web.mit.edu/newsoffice/2012/robots-hand-gestures-0314.html.

Yu et al.; "FlyingBuddy2: A Brain-controlled Assistant for the Handicapped" Online Video Clip; Pervasive Computing Group at CCNT Lab, Zhejiang University, China; Presented at Ubicomp 2012; accessed on Sep. 11, 2012; located at http://www.youtube.com/watch?v=JH96O5niEnl&feature=youtu.be; also located at http://www.wired.com/gadgetlab/2012/08/zhejiang-university-china-brain-controlled-quadcopter/.

BBC; "Researchers use spoofing to 'hack' into a flying drone"; BBC News Technology; Jun. 29, 2012; pp. 1-3; located at http://www.bbc.com/news/technology-18643134.

Hambling, David; "Aussie Hovering Drone is Straight Outta *Avatar*"; Wired.com Danger Room; Dec. 17, 2009; pp. 1-2; located at http://www.wired.com/dangerroom/2009/12/australian-drone-perches-stares/.

Hardesty, Larry; "Guiding robot planes with hand gestures"; MITnews; Mar. 14, 2012; pp. 1-3; located at http://web.mit.edu/newsoffice/2012/robots-band-gestures-0314.html.

(56) References Cited

OTHER PUBLICATIONS

Hill, David J.; "TacoCopter—Tacos Delivered Straight to Your Home With GPS Guided Quadcopters"; Singularity Hub; Mar. 25, 2012; pp. 1-4; located at http://singularityhub.com/2012/03/25/tacocopter-tacos-delivered-straight-to-your-home-with-gps-guided-quadcopters/.

Murph, Darren; "MIT software optimizes paths for automated undersea vehicles"; Engaget; Mar. 12, 2012; pp. 1-4; located at http://www.engadget.com/2012/03/12/mit-software-optimizes-paths-for-automated-undersea-vehicles/.

Olivarez-Giles, Nathan; "Brain-Controlled Quadcopter Drone Takes Flight in China"; Wired.com Gadget Lab; Aug. 31, 2012; pp. 1-7; located at http://www.wired.com/gadgetlab/2012/08/zhejiang-university-china-brain-controlled-quadcopter/.

Israel Aerospace Industries; "Mosquito"; UAV; bearing a date of 2002; created on Nov. 30, 2015; 3 pages; located at: http://www.iai.co.il/2013/36720-36275-en/BusinessAreas_UnmannedAirSystems.aspx; (best copy available, as provided by Examiner).

Spinka, Ondrej et al.; "Low-Cost Reconfigurable Control System for Small UAVs"; bearing a date of Aug. 28, 2009; IEEE, ISSN:0278-0046, IEEE Transactions on Industrial Electronics; vol. 58, No. 3; bearing a date of Mar. 2011; pp. 880-889.

\* cited by examiner

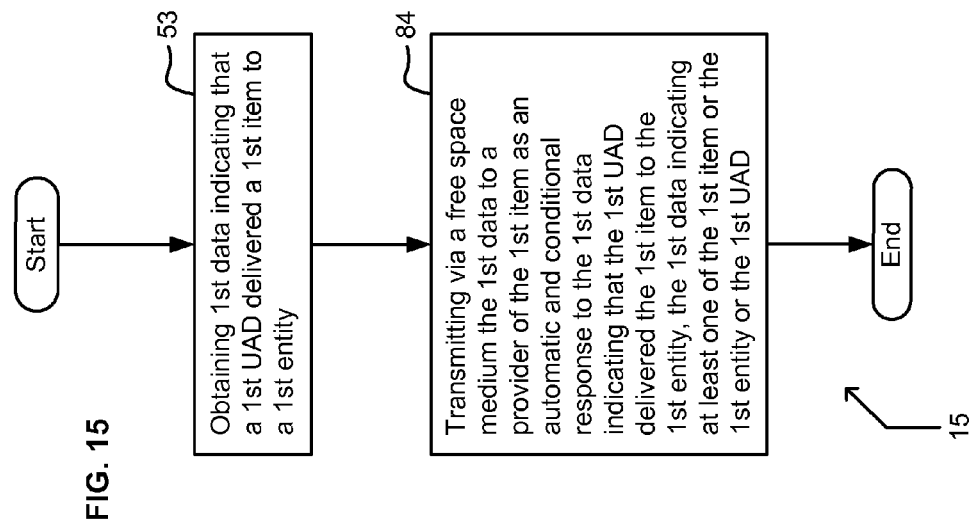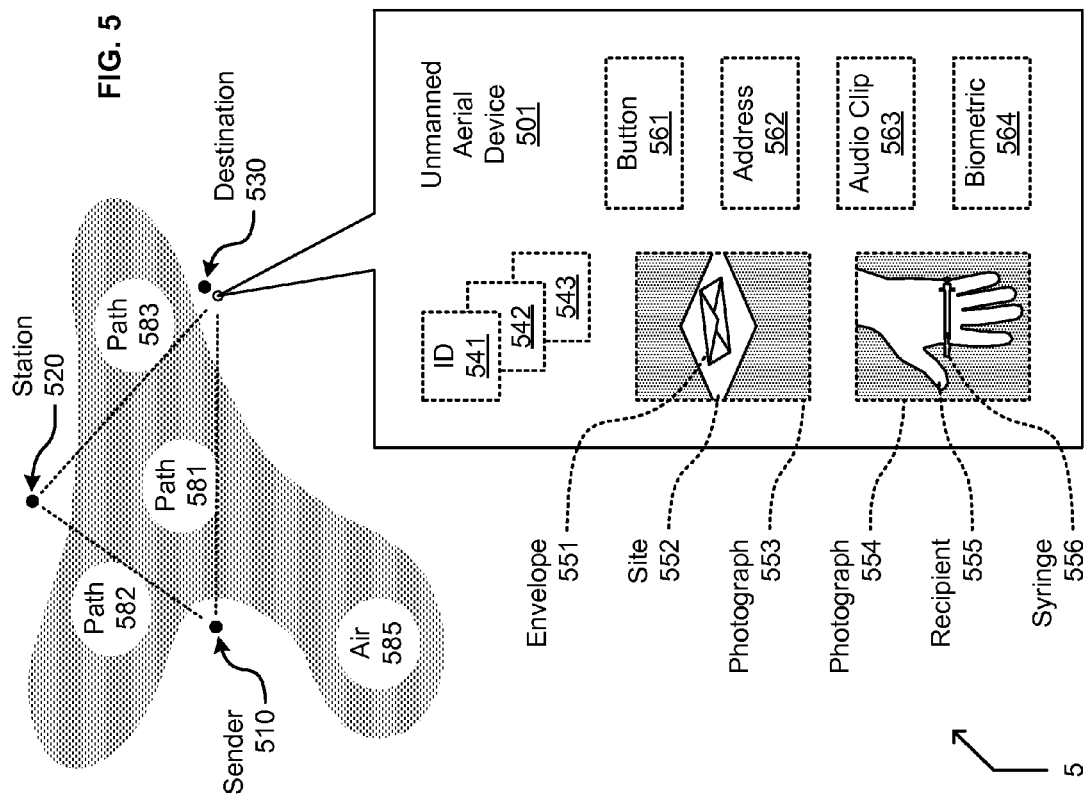

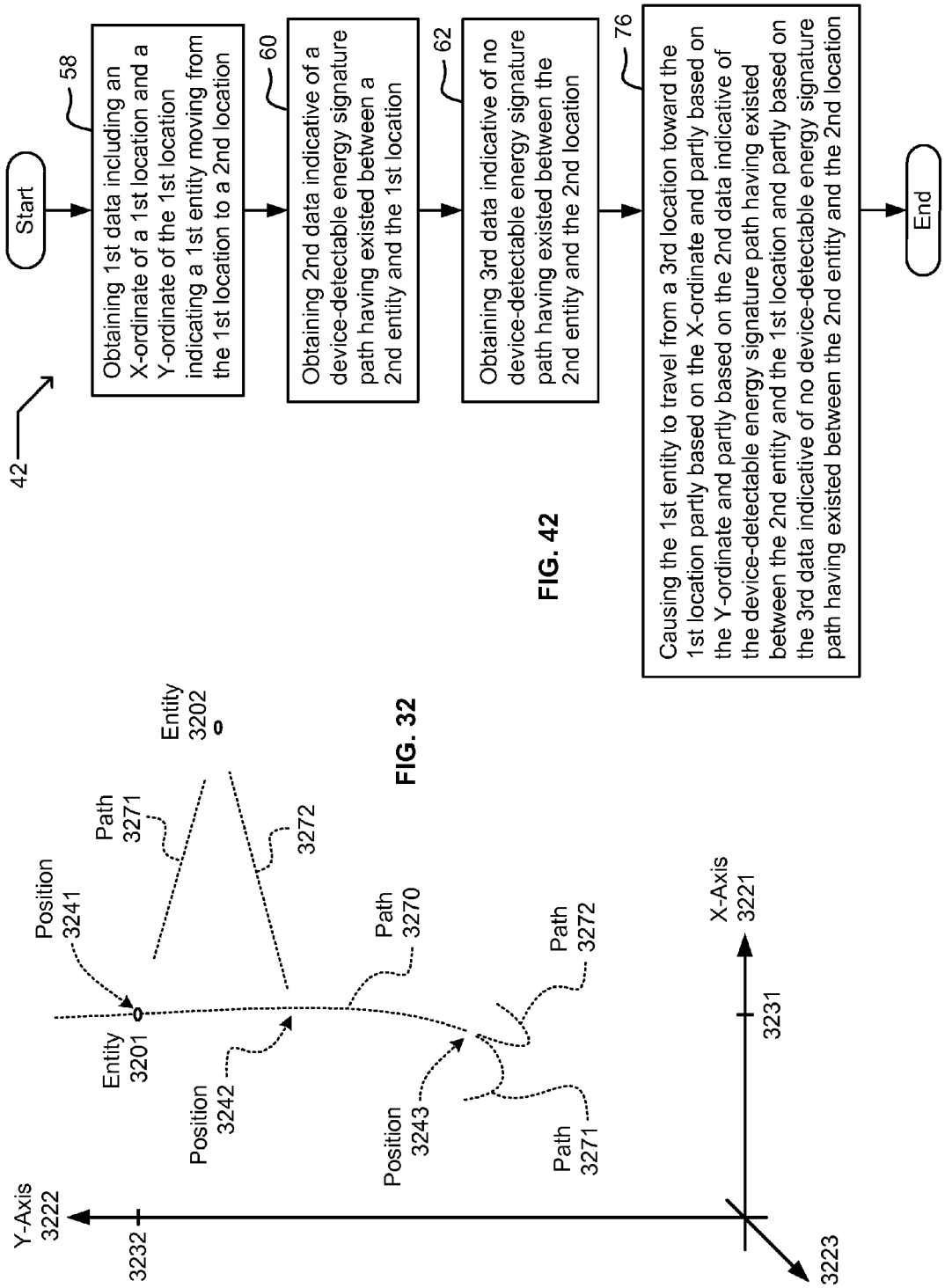

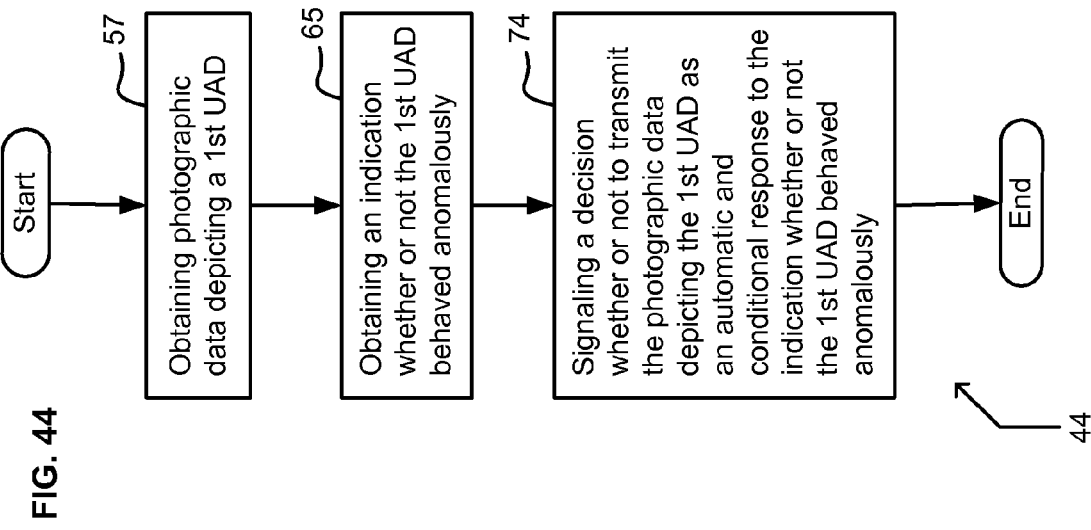
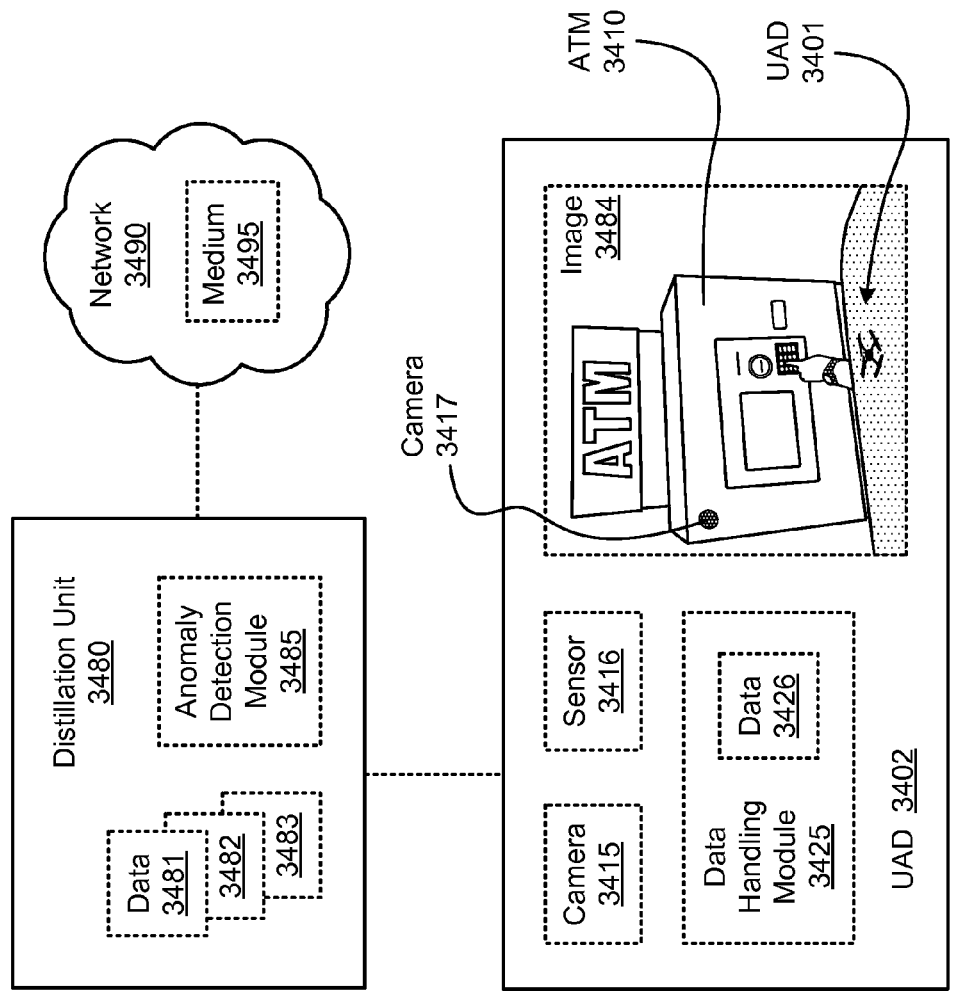

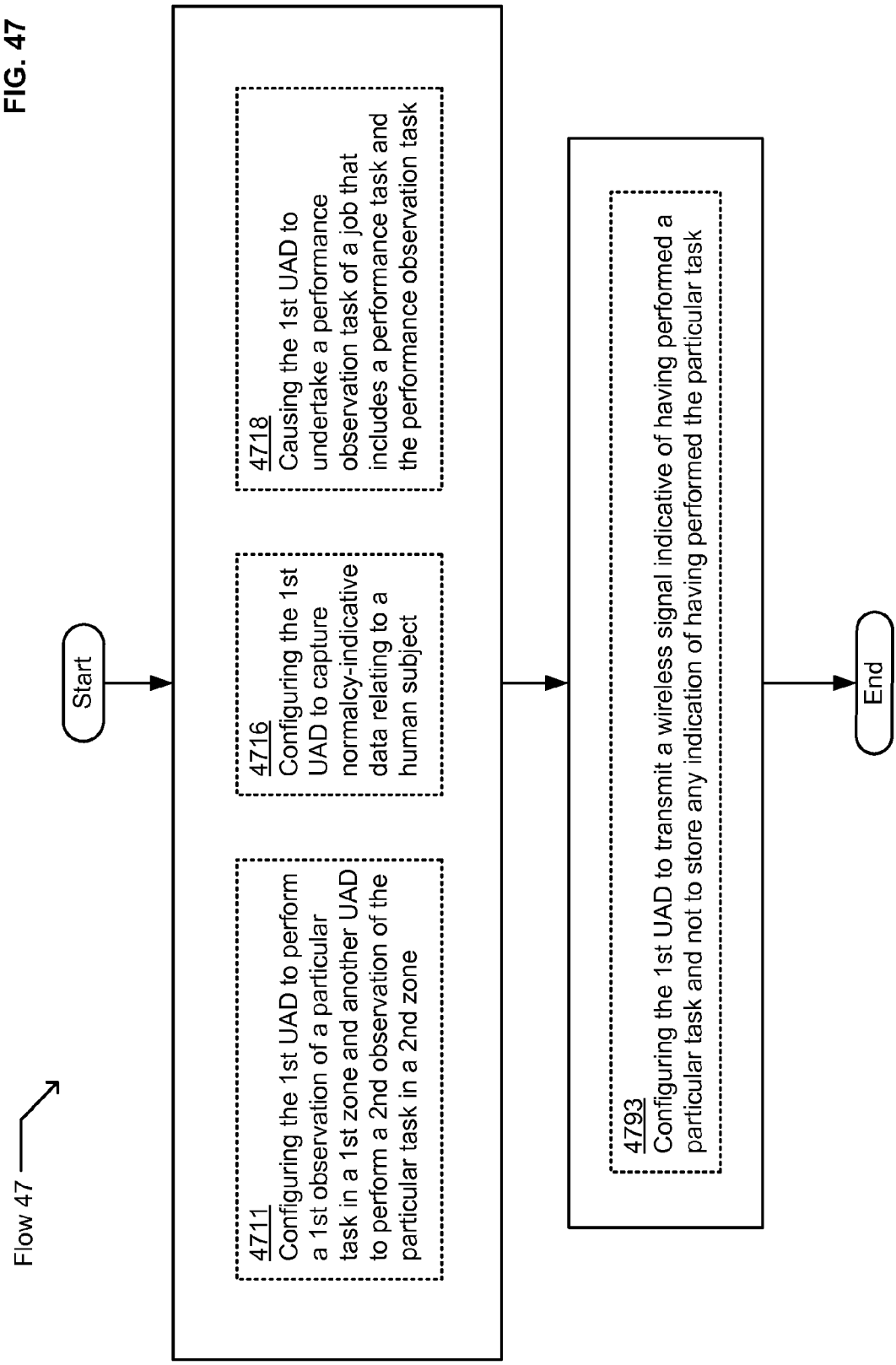

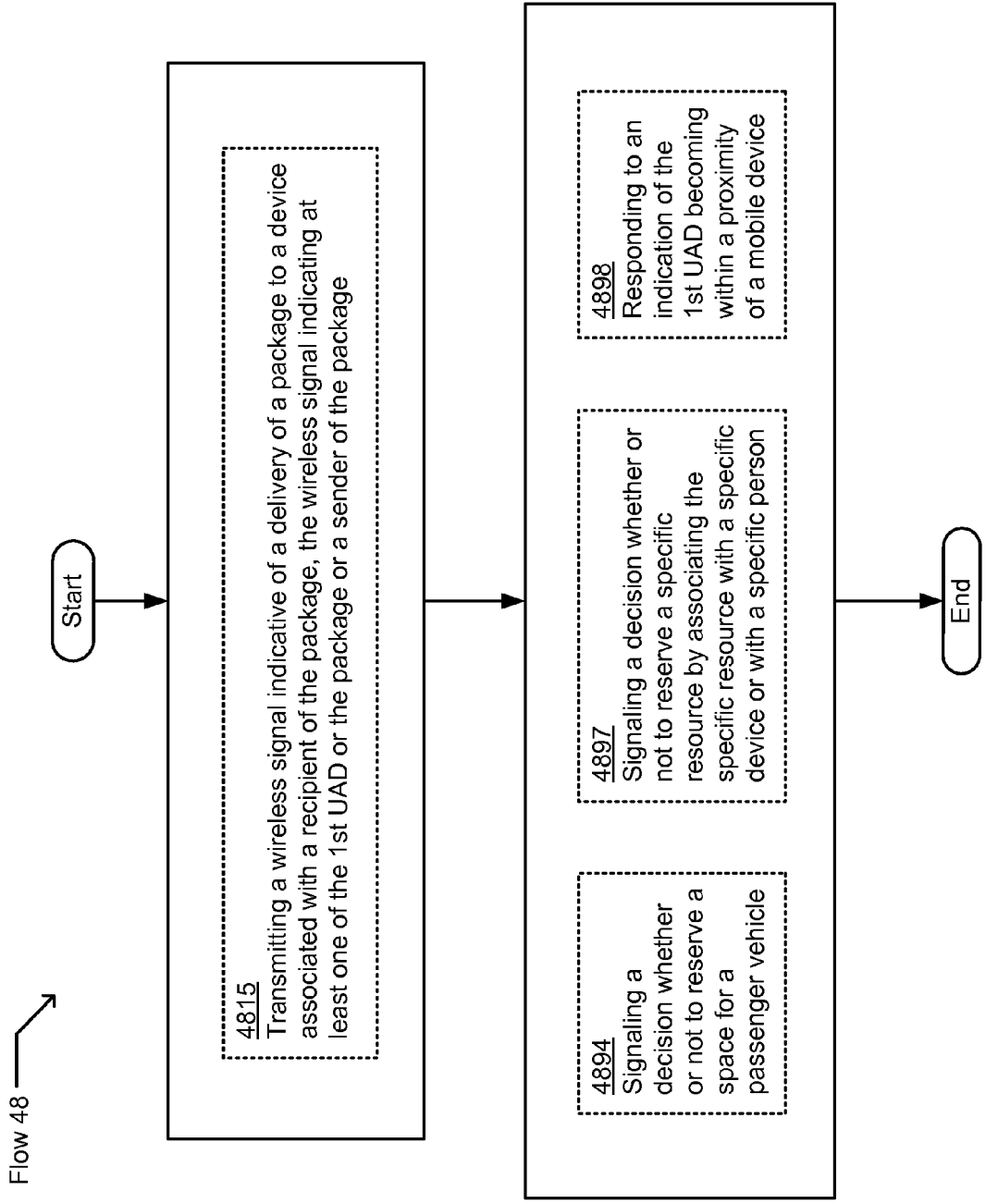

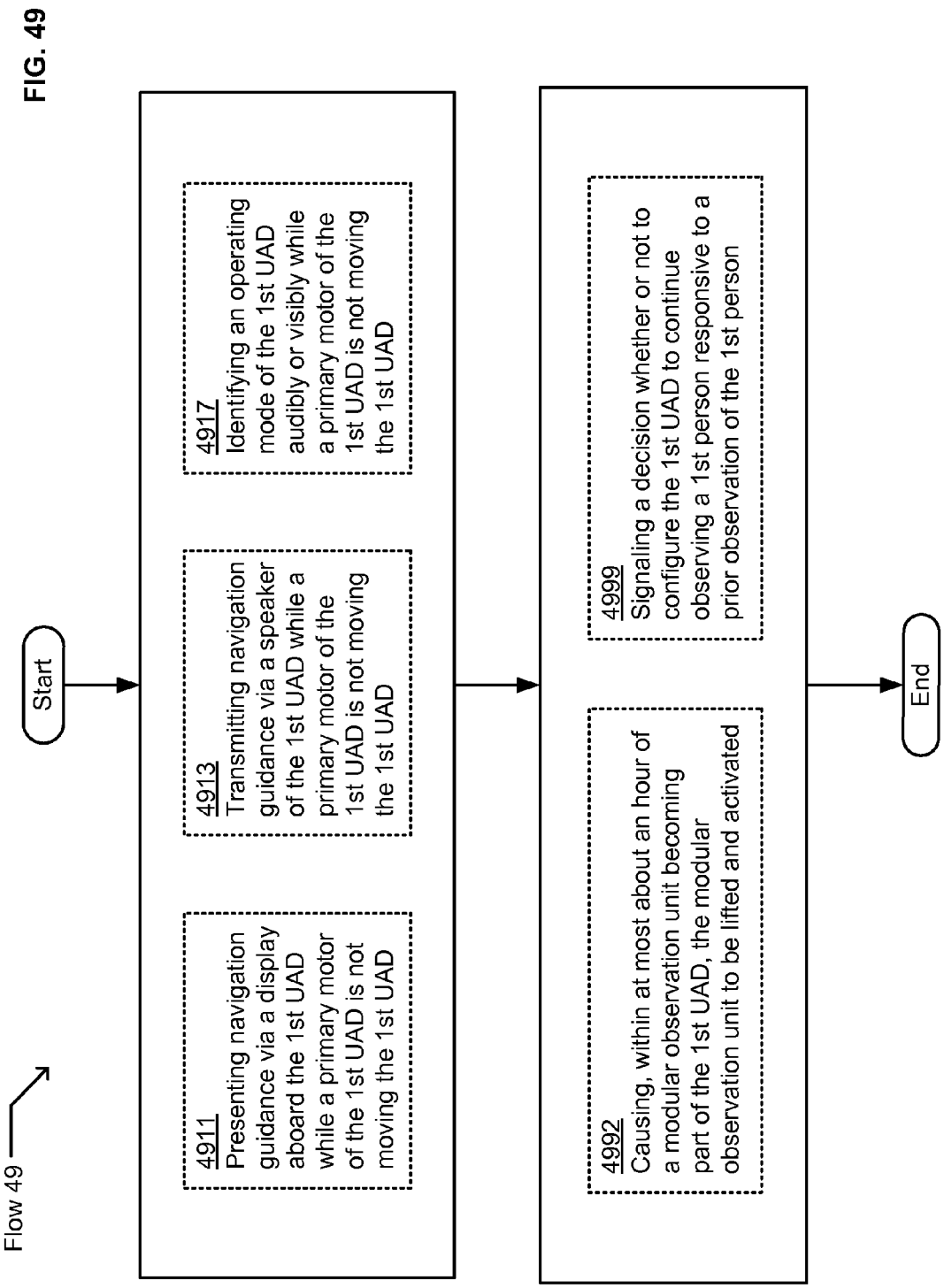

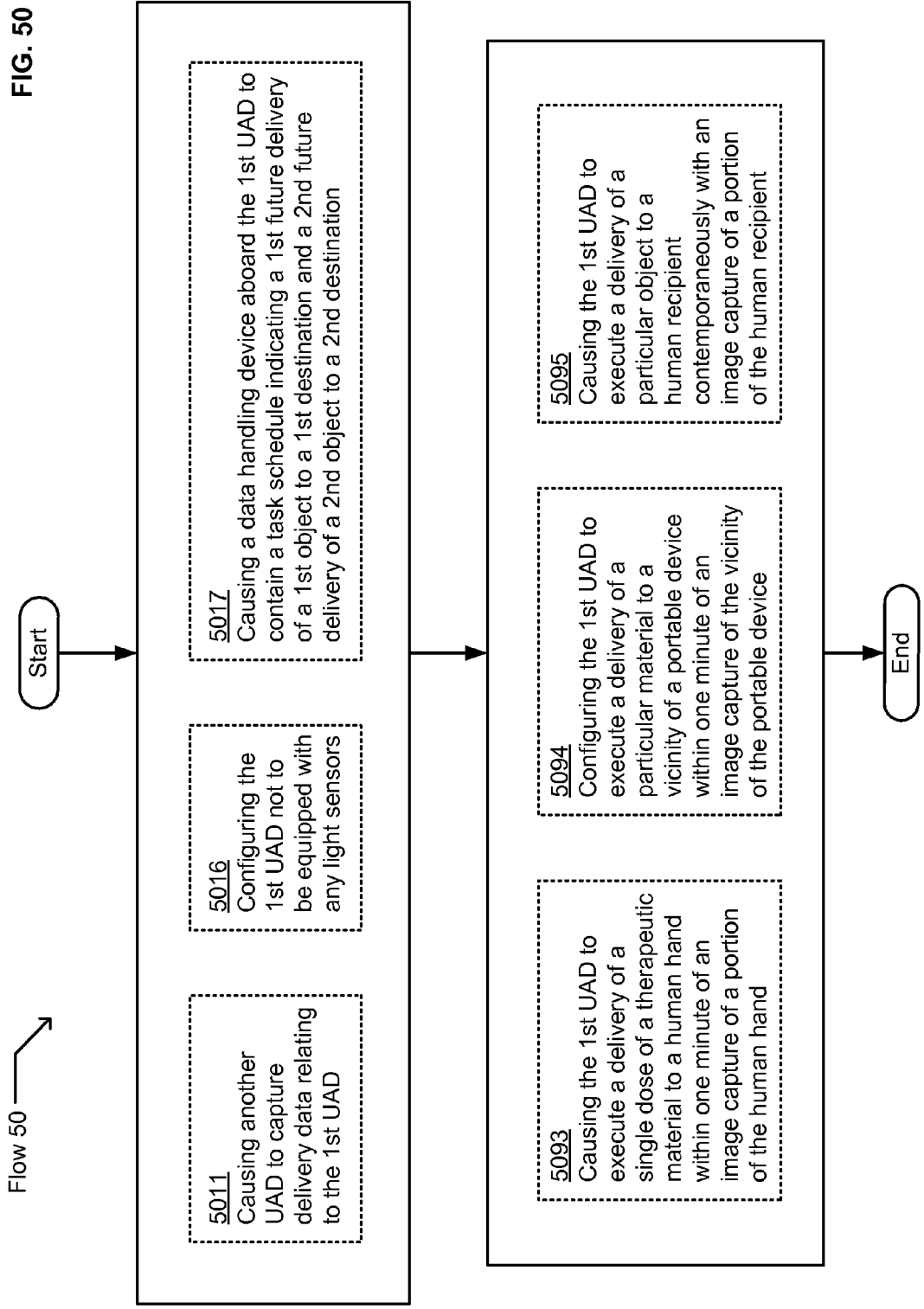

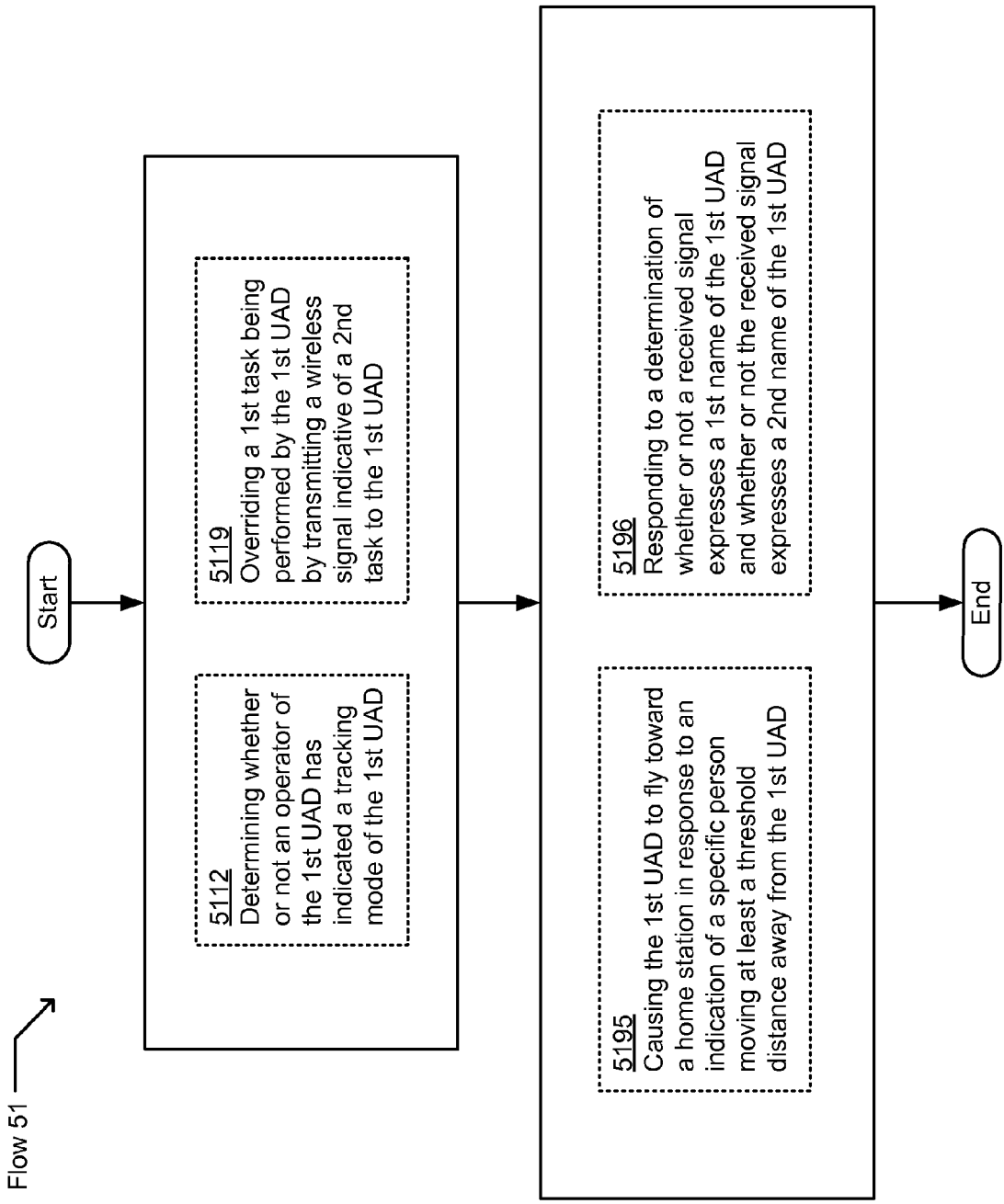

UNMANNED DEVICE INTERACTION METHODS AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. application Ser. Nos. 13/551,266, 13/551,287, 13/551,301, 13/551,320, and 13/551,334, each entitled UNMANNED DEVICE UTILIZATION METHODS AND SYSTEMS, naming Royce A. Levien, Richard T. Lord, Robert W. Lord, Mark A. Malamud, John D. Rinaldo, Jr., and Lowell L. Wood, Jr., as inventors, filed 17 Jul. 2012, each of which is currently co-pending or is an application of which a currently co-pending application is entitled to the benefit of the filing date. For purposes of the USPTO extra-statutory requirements, the present application likewise constitutes a continuation-in-part of U.S. application Ser. Nos. 13/601,060, 13/601,082, 13/601,096, 13/601,112, 13/601,140, and 13/601,169, each entitled UNMANNED DEVICE INTERACTION METHODS AND SYSTEMS, naming Royce A. Levien, Richard T. Lord, Robert W. Lord, Mark A. Malamud, John D. Rinaldo, Jr., and Lowell L. Wood, Jr., as inventors, filed on 31 Aug. 2012, each of which is currently co-pending or is an application of which a currently co-pending application is entitled to the benefit of the filing date.

For purposes of the USPTO extra-statutory requirements, the present application claims benefit of priority of U.S. application Ser. Nos. 13/551,266, 13/551,287, 13/551,301, 13/551,320, and 13/551,334, each entitled UNMANNED DEVICE UTILIZATION METHODS AND SYSTEMS, naming Royce A. Levien, Richard T. Lord, Robert W. Lord, Mark A. Malamud, John D. Rinaldo, Jr., and Lowell L. Wood, Jr., as inventors, filed 17 Jul. 2012, each of which was filed within the twelve months preceding the filing date of the present application or is an application of which a currently co-pending application is entitled to the benefit of the filing date. For purposes of the USPTO extra-statutory requirements, the present application likewise claims benefit of priority of U.S. application Ser. Nos. 13/601,060, 13/601,082, 13/601,096, 13/601,112, 13/601,140, and 13/601,169, each entitled UNMANNED DEVICE INTERACTION METHODS AND SYSTEMS, naming Royce A. Levien, Richard T. Lord, Robert W. Lord, Mark A. Malamud, John D. Rinaldo, Jr., and Lowell L. Wood, Jr., as inventors, filed on 31 Aug. 2012, each of which was filed within the twelve months preceding the filing date of the present application or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

BACKGROUND

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct." (e.g., that "software"—a computer program or computer programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

SUMMARY

In one or more various aspects, a method includes but is not limited to obtaining a descriptor of a first entity operating a first unmanned aerial device; obtaining an operatorship criterion; and signaling a decision whether or not to impede the first unmanned aerial device entering a particular region as an automatic and conditional result of applying the operatorship criterion to the descriptor of the first entity operating the first unmanned aerial device. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for obtaining a descriptor of a first entity operating a first unmanned aerial device; circuitry for obtaining an operatorship criterion; and circuitry for signaling a decision whether or not to impede the first unmanned aerial device entering a particular region as an automatic and conditional result of applying the operatorship criterion to the descriptor of the first entity operating the first unmanned aerial device. In addition to the foregoing, other system aspects are described in the claims, drawings, and text forming a part of the disclosure set forth herein.

In one aspect, a computer program product comprising an article of manufacture bears instructions including, but not limited to, obtaining a descriptor of a first entity operating a first unmanned aerial device; obtaining an operatorship criterion; and signaling a decision whether or not to impede the first unmanned aerial device entering a particular region as an automatic and conditional result of applying the operatorship criterion to the descriptor of the first entity operating the first unmanned aerial device. In addition to the foregoing, other computer program products are described in the claims, drawings, and text forming a part of the disclosure set forth herein.

In one aspect, a computer architecture comprising at least one level includes, but is not limited to, obtaining a descriptor of a first entity operating a first unmanned aerial device; obtaining an operatorship criterion; and signaling a decision whether or not to impede the first unmanned aerial device entering a particular region as an automatic and conditional result of applying the operatorship criterion to the descriptor of the first entity operating the first unmanned aerial device. In addition to the foregoing, other computer architecture details are described in the claims, drawings, and text forming a part of the disclosure set forth herein.

In one aspect, a device configured by computational language includes, but is not limited to, obtaining a descriptor of a first entity operating a first unmanned aerial device; obtaining an operatorship criterion; and signaling a decision whether or not to impede the first unmanned aerial device entering a particular region as an automatic and conditional result of applying the operatorship criterion to the descriptor of the first entity operating the first unmanned aerial device. In addition to the foregoing, other hardware aspects are described in the claims, drawings, and text forming a part of the disclosure set forth herein.

In one or more various aspects, a method includes but is not limited to detecting a first unmanned aerial device being within a vicinity of a portal; obtaining an indication of an identity of the first unmanned aerial device; and signaling a decision whether or not to allow an actuator to obstruct the portal partly based on the indication of the identity of the first unmanned aerial device and partly based on the first unmanned aerial device being within the vicinity of the portal. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for detecting a first unmanned aerial device being within a vicinity of a portal; circuitry for obtaining an indication of an identity of the first unmanned aerial device; and circuitry for signaling a decision whether or not to allow an actuator to obstruct the portal partly based on the indication of the identity of the first unmanned aerial device and partly based on the first unmanned aerial device being within the vicinity of the portal. In addition to the foregoing, other system aspects are described in the claims, drawings, and text forming a part of the disclosure set forth herein.

In one aspect, a computer program product comprising an article of manufacture bears instructions including, but not limited to, detecting a first unmanned aerial device being within a vicinity of a portal; obtaining an indication of an identity of the first unmanned aerial device; and signaling a decision whether or not to allow an actuator to obstruct the portal partly based on the indication of the identity of the first unmanned aerial device and partly based on the first unmanned aerial device being within the vicinity of the portal. In addition to the foregoing, other computer program products are described in the claims, drawings, and text forming a part of the disclosure set forth herein.

In one aspect, a computer architecture comprising at least one level includes, but is not limited to, detecting a first unmanned aerial device being within a vicinity of a portal; obtaining an indication of an identity of the first unmanned aerial device; and signaling a decision whether or not to allow an actuator to obstruct the portal partly based on the indication of the identity of the first unmanned aerial device and partly based on the first unmanned aerial device being within the vicinity of the portal. In addition to the foregoing, other computer architecture details are described in the claims, drawings, and text forming a part of the disclosure set forth herein.

In one aspect, a device configured by computational language includes, but is not limited to, detecting a first unmanned aerial device being within a vicinity of a portal; obtaining an indication of an identity of the first unmanned aerial device; and signaling a decision whether or not to allow an actuator to obstruct the portal partly based on the indication of the identity of the first unmanned aerial device and partly based on the first unmanned aerial device being within the vicinity of the portal. In addition to the foregoing, other hardware aspects are described in the claims, drawings, and text forming a part of the disclosure set forth herein.

In one or more various aspects, a method includes but is not limited to obtaining first data including optical data from a vicinity of a reference surface in contact with a first unmanned aerial device; signaling a decision as an automatic and conditional response to the application of a first recognition criterion to the optical data from the vicinity of the reference surface in contact with the first unmanned aerial device whether or not to cause the first unmanned aerial device to be disengaged from the reference surface; and signaling a decision as an automatic and conditional response to the application of the first recognition criterion to the optical data from the vicinity of the reference surface whether or not to cause the first unmanned aerial device to obtain second data with the first unmanned aerial device disengaged from the reference surface. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for obtaining first data including optical data from a vicinity of a reference surface in contact with a first unmanned aerial device; circuitry for signaling a decision as an automatic and conditional response to the application of a first recognition criterion to the optical data from the vicinity of the reference surface in contact with the first unmanned aerial device whether or not to cause the first unmanned aerial device to be disengaged from the reference surface; and circuitry for signaling a decision as an automatic and conditional response to the application of the first recognition criterion to the optical data from the vicinity of the reference surface whether or not to cause the first unmanned aerial device to obtain second data with the first unmanned aerial device disengaged from the reference surface. In addition to the foregoing, other system aspects are described in the claims, drawings, and text forming a part of the disclosure set forth herein.

In one aspect, a computer program product comprising an article of manufacture bears instructions including, but not limited to, obtaining first data including optical data from a vicinity of a reference surface in contact with a first unmanned aerial device; signaling a decision as an automatic and conditional response to the application of a first recognition criterion to the optical data from the vicinity of the reference surface in contact with the first unmanned aerial device whether or not to cause the first unmanned aerial device to be disengaged from the reference surface; and signaling a decision as an automatic and conditional response to the application of the first recognition criterion to the optical data from the vicinity of the reference surface whether or not to cause the first unmanned aerial device to obtain second data with the first unmanned aerial device disengaged from the reference surface. In addition to the foregoing, other computer program products are described in the claims, drawings, and text forming a part of the disclosure set forth herein.

In one aspect, a computer architecture comprising at least one level includes, but is not limited to, obtaining first data including optical data from a vicinity of a reference surface in contact with a first unmanned aerial device; signaling a decision as an automatic and conditional response to the application of a first recognition criterion to the optical data from the vicinity of the reference surface in contact with the first unmanned aerial device whether or not to cause the first unmanned aerial device to be disengaged from the reference surface; and signaling a decision as an automatic and conditional response to the application of the first recognition criterion to the optical data from the vicinity of the reference surface whether or not to cause the first unmanned aerial device to obtain second data with the first unmanned aerial device disengaged from the reference surface. In addition to the foregoing, other computer architecture details are described in the claims, drawings, and text forming a part of the disclosure set forth herein.

In one aspect, a device configured by computational language includes, but is not limited to, obtaining first data including optical data from a vicinity of a reference surface in contact with a first unmanned aerial device; signaling a decision as an automatic and conditional response to the application of a first recognition criterion to the optical data from the vicinity of the reference surface in contact with the first unmanned aerial device whether or not to cause the first unmanned aerial device to be disengaged from the reference surface; and signaling a decision as an automatic and conditional response to the application of the first recognition criterion to the optical data from the vicinity of the reference surface whether or not to cause the first unmanned aerial device to obtain second data with the first unmanned aerial device disengaged from the reference surface. In addition to the foregoing, other hardware aspects are described in the claims, drawings, and text forming a part of the disclosure set forth herein.

In one or more various aspects, a method includes but is not limited to obtaining operator input from an operator of a first unmanned aerial device as an earlier input component; obtaining environmental sensor input from a vicinity of the first unmanned aerial device as a later input component; and signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for obtaining operator input from an operator of a first unmanned aerial device as an earlier input component; circuitry for obtaining environmental sensor input from a vicinity of the first unmanned aerial device as a later input component; and circuitry for signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component. In addition to the foregoing, other system aspects are described in the claims, drawings, and text forming a part of the disclosure set forth herein.

In one aspect, a computer program product comprising an article of manufacture bears instructions including, but not limited to, obtaining operator input from an operator of a first unmanned aerial device as an earlier input component; obtaining environmental sensor input from a vicinity of the first unmanned aerial device as a later input component; and signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component. In addition to the foregoing, other computer program products are described in the claims, drawings, and text forming a part of the disclosure set forth herein.

In one aspect, a computer architecture comprising at least one level includes, but is not limited to, obtaining operator input from an operator of a first unmanned aerial device as an earlier input component; obtaining environmental sensor input from a vicinity of the first unmanned aerial device as a later input component; and signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component. In addition to the foregoing, other computer architecture details are described in the claims, drawings, and text forming a part of the disclosure set forth herein.

In one aspect, a device configured by computational language includes, but is not limited to, obtaining operator input from an operator of a first unmanned aerial device as an earlier input component; obtaining environmental sensor input from a vicinity of the first unmanned aerial device as a later input component; and signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component. In addition to the foregoing, other hardware aspects are described in the claims, drawings, and text forming a part of the disclosure set forth herein.

In one or more various aspects, a method includes but is not limited to obtaining first data including an X-ordinate of a first location and a Y-ordinate of the first location indicating a first entity moving from the first location to a second location; obtaining second data indicative of a device-detectable energy signature path having existed between a second entity and the first location; obtaining third data indicative of no device-detectable energy signature path having existed between the second entity and the second location; and causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for obtaining first data including an X-ordinate of a first location and a Y-ordinate of the first location indicating a first entity moving from the first location to a second location; circuitry for obtaining second data indicative of a device-detectable energy signature path having existed between a second entity and the first location; circuitry for obtaining third data indicative of no device-detectable energy signature path having existed between the second entity and the second location; and circuitry for causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location. In addition to the foregoing, other system aspects are described in the claims, drawings, and text forming a part of the disclosure set forth herein.

In one aspect, a computer program product comprising an article of manufacture bears instructions including, but not limited to, obtaining first data including an X-ordinate of a first location and a Y-ordinate of the first location indicating a first entity moving from the first location to a second location; obtaining second data indicative of a device-detectable energy signature path having existed between a second entity and the first location; obtaining third data indicative of no device-detectable energy signature path having existed between the second entity and the second location; and causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location. In addition to the foregoing, other computer program products are described in the claims, drawings, and text forming a part of the disclosure set forth herein.

In one aspect, a computer architecture comprising at least one level includes, but is not limited to, obtaining first data including an X-ordinate of a first location and a Y-ordinate of the first location indicating a first entity moving from the first location to a second location; obtaining second data indicative of a device-detectable energy signature path having existed between a second entity and the first location;

obtaining third data indicative of no device-detectable energy signature path having existed between the second entity and the second location; and causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location. In addition to the foregoing, other computer architecture details are described in the claims, drawings, and text forming a part of the disclosure set forth herein.

In one aspect, a device configured by computational language includes, but is not limited to, obtaining first data including an X-ordinate of a first location and a Y-ordinate of the first location indicating a first entity moving from the first location to a second location; obtaining second data indicative of a device-detectable energy signature path having existed between a second entity and the first location; obtaining third data indicative of no device-detectable energy signature path having existed between the second entity and the second location; and causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location. In addition to the foregoing, other hardware aspects are described in the claims, drawings, and text forming a part of the disclosure set forth herein.

In one or more various aspects, a method includes but is not limited to obtaining an indication of a first time interval from when a device-detectable energy signature path existed between a first entity and a second entity until a reference time and signaling a decision whether or not to change an aerial navigation protocol of the first entity as an automatic and conditional response to a result of comparing a threshold against the indication of the first time interval from when the device-detectable energy signature path existed between the first entity and the second entity until the reference time. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for obtaining an indication of a first time interval from when a device-detectable energy signature path existed between a first entity and a second entity until a reference time and circuitry for signaling a decision whether or not to change an aerial navigation protocol of the first entity as an automatic and conditional response to a result of comparing a threshold against the indication of the first time interval from when the device-detectable energy signature path existed between the first entity and the second entity until the reference time. In addition to the foregoing, other system aspects are described in the claims, drawings, and text forming a part of the disclosure set forth herein.

In one aspect, a computer program product comprising an article of manufacture bears instructions including, but not limited to, obtaining an indication of a first time interval from when a device-detectable energy signature path existed between a first entity and a second entity until a reference time and signaling a decision whether or not to change an aerial navigation protocol of the first entity as an automatic and conditional response to a result of comparing a threshold against the indication of the first time interval from when the device-detectable energy signature path existed between the first entity and the second entity until the reference time. In addition to the foregoing, other computer program products are described in the claims, drawings, and text forming a part of the disclosure set forth herein.

In one aspect, a computer architecture comprising at least one level includes, but is not limited to, obtaining an indication of a first time interval from when a device-detectable energy signature path existed between a first entity and a second entity until a reference time and signaling a decision whether or not to change an aerial navigation protocol of the first entity as an automatic and conditional response to a result of comparing a threshold against the indication of the first time interval from when the device-detectable energy signature path existed between the first entity and the second entity until the reference time. In addition to the foregoing, other computer architecture details are described in the claims, drawings, and text forming a part of the disclosure set forth herein.

In one aspect, a device configured by computational language includes, but is not limited to, obtaining an indication of a first time interval from when a device-detectable energy signature path existed between a first entity and a second entity until a reference time and signaling a decision whether or not to change an aerial navigation protocol of the first entity as an automatic and conditional response to a result of comparing a threshold against the indication of the first time interval from when the device-detectable energy signature path existed between the first entity and the second entity until the reference time. In addition to the foregoing, other hardware aspects are described in the claims, drawings, and text forming a part of the disclosure set forth herein.

In one or more various aspects, a method includes but is not limited to obtaining photographic data depicting a first unmanned aerial device; obtaining an indication whether or not the first unmanned aerial device behaved anomalously; and signaling a decision whether or not to transmit the photographic data depicting the first unmanned aerial device as an automatic and conditional response to the indication whether or not the first unmanned aerial device behaved anomalously. In addition to the foregoing, other method aspects are described in the claims, drawings, and text forming a part of the disclosure set forth herein.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for effecting the herein referenced method aspects. The circuitry and/or programming may be virtually any combination of hardware, software, and/or firmware configured to effect the herein referenced method aspects depending upon the design choices of the system designer, and limited to patentable subject matter under 35 USC 101.

An embodiment provides a system. In one implementation, the system includes but is not limited to circuitry for obtaining photographic data depicting a first unmanned aerial device; circuitry for obtaining an indication whether or not the first unmanned aerial device behaved anomalously; and circuitry for signaling a decision whether or not to transmit the photographic data depicting the first unmanned aerial device as an automatic and conditional response to the indication whether or not the first unmanned aerial device behaved anomalously. In addition to the foregoing, other system aspects are described in the claims, drawings, and text forming a part of the disclosure set forth herein.

In one aspect, a computer program product comprising an article of manufacture bears instructions including, but not limited to, obtaining photographic data depicting a first unmanned aerial device; obtaining an indication whether or not the first unmanned aerial device behaved anomalously; and signaling a decision whether or not to transmit the photographic data depicting the first unmanned aerial device as an automatic and conditional response to the indication whether or not the first unmanned aerial device behaved anomalously. In addition to the foregoing, other computer program products are described in the claims, drawings, and text forming a part of the disclosure set forth herein.

In one aspect, a computer architecture comprising at least one level includes, but is not limited to, obtaining photographic data depicting a first unmanned aerial device; obtaining an indication whether or not the first unmanned aerial device behaved anomalously; and signaling a decision whether or not to transmit the photographic data depicting the first unmanned aerial device as an automatic and conditional response to the indication whether or not the first unmanned aerial device behaved anomalously. In addition to the foregoing, other computer architecture details are described in the claims, drawings, and text forming a part of the disclosure set forth herein.

In one aspect, a device configured by computational language includes, but is not limited to, obtaining photographic data depicting a first unmanned aerial device; obtaining an indication whether or not the first unmanned aerial device behaved anomalously; and signaling a decision whether or not to transmit the photographic data depicting the first unmanned aerial device as an automatic and conditional response to the indication whether or not the first unmanned aerial device behaved anomalously. In addition to the foregoing, other hardware aspects are described in the claims, drawings, and text forming a part of the disclosure set forth herein.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent by reference to the detailed description, the corresponding drawings, and/or in the teachings set forth herein

BRIEF DESCRIPTION OF THE FIGURES

FIG. 5 depicts an exemplary environment featuring a UAD in a vicinity of a destination.

FIG. 15 depicts a high-level logic flow of an operational process described with reference to FIG. 5.

FIG. 19 depicts a high-level logic flow of an operational process described with reference to FIG. 9.

FIG. 32 depicts an entity only intermittently able to obtain an indication of another entity, one or both being UAD's.

FIG. 42 depicts a high-level logic flow of an operational process described with reference to FIG. 32.

FIG. 34 depicts an exemplary environment featuring a device configured to signal a decision whether or not to transmit a depiction of a UAD.

FIG. 44 depicts a high-level logic flow of an operational process described with reference to FIG. 34.

FIGS. 47-51 each depict intensive and extensive operations that may be performed in conjunction with one or more high-level logic flows shown in FIG. 15-19 or 38-44.

DETAILED DESCRIPTION

Figure 1:
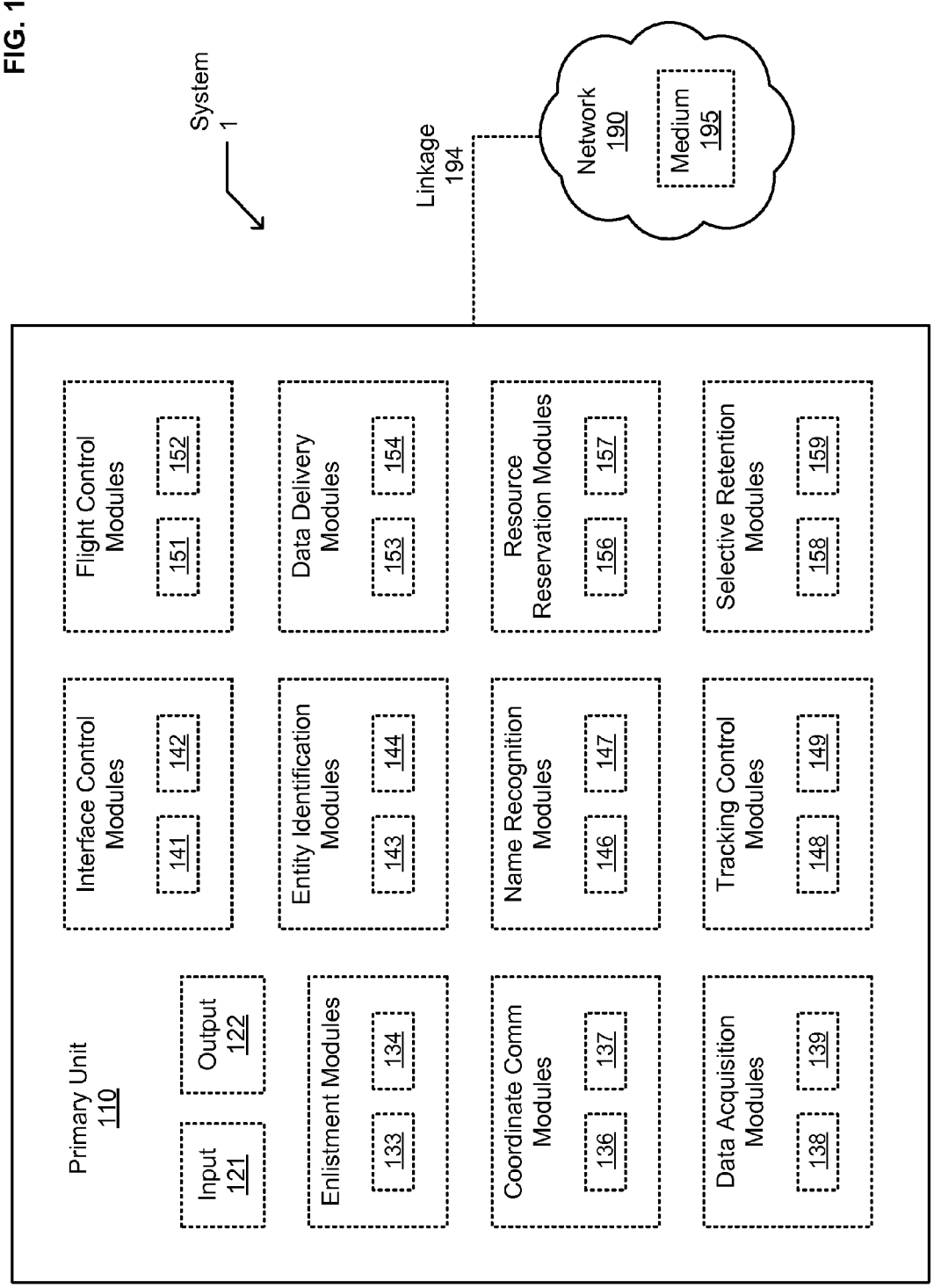
FIG. 1 depicts an exemplary environment featuring a primary unit operably linked to a network.

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof, limited to patentable subject matter under 35 U.S.C. 101. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof, limited to patentable subject matter under 35 U.S.C. 101.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

FIG. 1 depicts a context in which one or more technologies may be implemented. System 1 comprises a primary unit 110 that may comprise one or more instances of inputs 121; outputs 122; enlistment modules 133, 134; coordinate communication modules 136, 137; data acquisition modules 138, 139; interface control modules 141, 142; entity identification modules 143, 144; name recognition modules 146, 147; tracking control modules 148, 149; flight control modules 151, 152; data delivery modules 153, 154; resource reservation modules 156, 157; or selective retention modules 158, 159 as described in further detail below. In some contexts, primary unit 110 may be operably coupled to one or more networks 190 via one or more communication linkages 140. Instances of storage or other data-handling media 195 operably coupled to one or more such modules may, moreover, reside in primary unit 110 or network 190, as described below. As exemplified herein, a "module" may include special-purpose hardware, general-purpose hardware configured with special-purpose software, or other circuitry configured to perform one or more functions recited below. Also in some contexts such "modules" may be configured to establish or utilize an association (between two devices, e.g.) in response to common interactions (a backup from one device to the other, both logging into a password-access account, or sharing the same printer or router or other peripheral, e.g.). Moreover respective embodiments of primary unit 110 may implement substantially any combination thereof, as exemplified in protocols described below.

Figure 2:
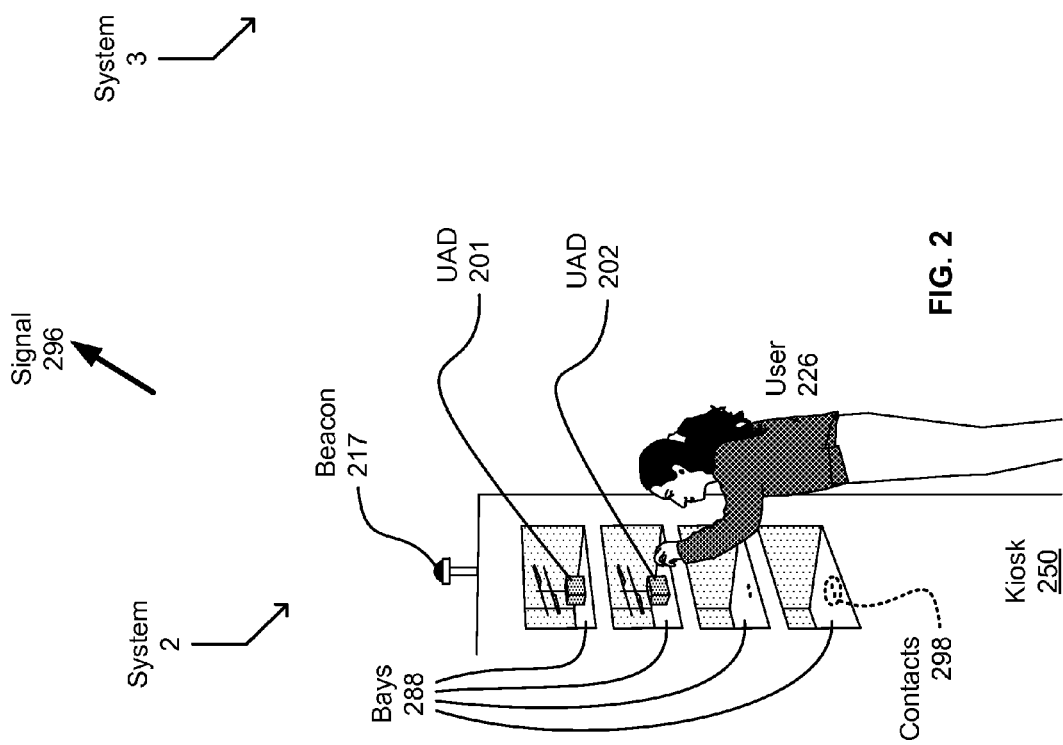
FIG. 2 depicts an exemplary environment featuring a user-accessible kiosk having several bays in which unmanned aerial devices (UAD's) may reside.

FIG. 2 depicts another context in which one or more technologies may be implemented. System 2 comprises a kiosk 250 having several bays 288 each large enough to receive a respective unmanned aerial device (UAD) 201, 202 and accessible to one or more users 226. In some variants kiosk 250 may also include one or more beacons 217 configured to emit an optical or other wireless homing signal 296 recognizable to one or more UAD's 201, 202. The signal 296 is distinctive enough to facilitate UAD's 201, 202 finding beacon 217 several meters or more away from kiosk 250. Moreover each of the bays 288 has protruding or recessed electrical contacts 298 therein to permit each UAD 201, 202 to recharge after it is placed or lands within the bay.

Figure 3:
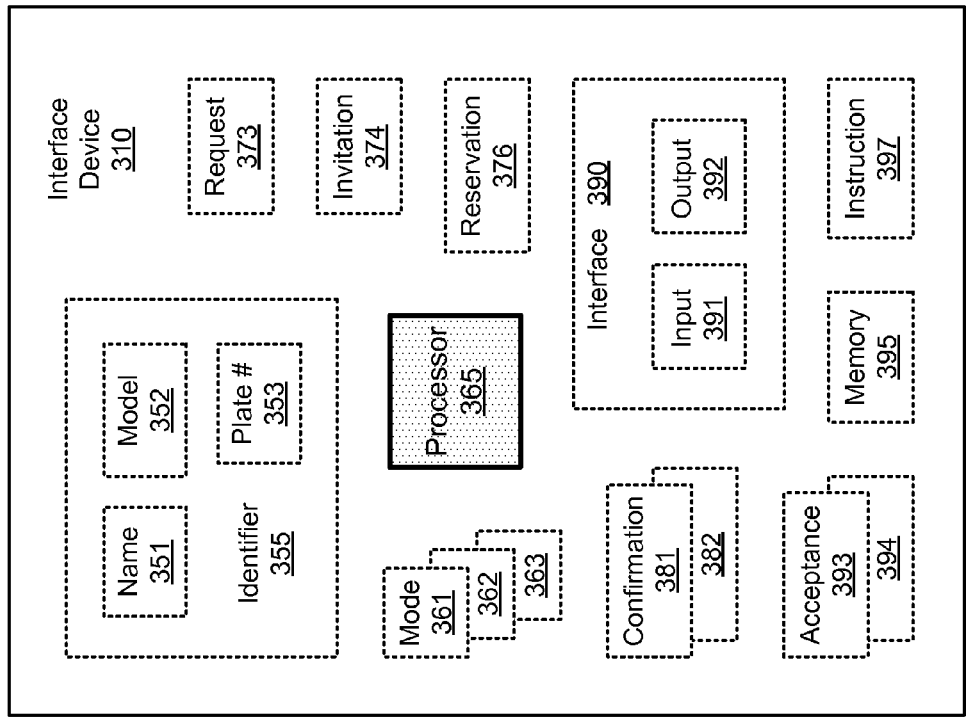
FIG. 3 depicts an exemplary environment featuring an interface device having at least one processor.

FIG. 3 depicts another system 3 in which one or more technologies may be implemented, one in which one or more instances of a name 351, model 352, or other identifier 355 refer to and identify interface device 310. In a context in which interface device 310 comprises a minivan or other passenger vehicle, for example, such identifier(s) 355 may comprise a plate number 353 of the vehicle. As explained below, interface device 310 may further include one or more instances (implemented in special-purpose circuitry or software executable by one or more processors 365, e.g.) of modes 361, 362, 363; requests 373; invitations 374; reservations 376; confirmations 381, 382; touchscreens or other local interfaces 390 (comprising one or more inputs 391 or outputs 392 physically accessible to or observable by a user at interface device 310, e.g.); acceptances 393, 394; memories 395; or instructions 397.

In light of teachings herein, numerous existing techniques may be applied for configuring special-purpose circuitry or other structures effective for conducting a context-specific structured dialog or other user interaction without undue experimentation or for configuring other decisions and devices as described herein. See, e.g., U.S. Pat. No. 8,024,329 ("Using inverted indexes for contextual personalized information retrieval"); U.S. Pat. No. 7,970,735 ("Cross varying dimension support for analysis services engine"); U.S. Pat. No. 7,920,678 ("Personal virtual assistant"); U.S. Pat. No. 7,870,117 ("Constructing a search query to execute a contextual personalized search of a knowledge base"); U.S. Pat. No. 7,761,480 ("Information access using ontologies"); U.S. Pat. No. 7,743,051 ("Methods, systems, and user interface for e-mail search and retrieval"); U.S. Pat. No. 7,593,982 ("Method, system, and computer program product for saving a search result within a global computer network"); U.S. Pat. No. 7,363,246 ("System and method for enhancing buyer and seller interaction during a group-buying sale"); U.S. Pat. No. 7,177,948 ("Method and apparatus for enhancing online searching sale"); U.S. Pat. No. 6,798,867 ("System and method for the creation and automatic deployment of personalized, dynamic and interactive voice services, with real-time database queries"); U.S. Pub. No. 2011/0081053 ("Methods and systems for occlusion tolerant face recognition"); U.S. Pub. No. 2008/0159622 ("Target object recognition in images and video").

Referring again to FIG. 1, network 190 may serve as a context for introducing one or more processes, systems or other articles described below. In some instances network 190 may include one or more search engines, satellites, servers, processors, routers, or other devices. In some contexts, one or more interface devices owned or operated by user 226 may interact through network 190 (e.g. with one or more other interface devices or networks as described herein). One or more such associated interface devices 310 may be mobile devices, in some contexts, or may function in cooperation (as a network subsystem, e.g.) even when remote from one another. Alternatively or additionally, one or more other interface devices owned or operated by user 226 may likewise interact locally or remotely with or through one another or other interface devices (through network 190, e.g.).

In some contexts, such interface devices (of FIG. 2, e.g.) may include or otherwise communicate with one or more instances of primary unit 110 and may include one or more instances of data outputs or other implementations of machines, articles of manufacture, or compositions of matter that include circuitry or other logic as described below. In some contexts, such implementations may be held or transmitted by conduits, storage devices, memories, other holding devices, or other circuitry for handling data or software (in a satellite, server, or router, e.g.) as described herein. In various embodiments, one or more instances of implementation components or implementation output data may each be expressed within any aspect or combination of software, firmware, or hardware as signals, data, designs, logic, instructions, or other such special-purpose expression or implementation. Interface devices (such as that of FIG. 2, e.g.) may likewise include one or more instances of lenses, transmitters, receivers, integrated circuits, antennas, output devices, reflectors, or input devices for handling data or communicating with local users or via linkage 140, for example.

Those skilled in the art will recognize that some list items may also function as other list items. In the above-listed types of media, for example, some instances of interface devices may include conduits or may also function as storage devices that are also holding devices. One or more transmitters may likewise include input devices or bidirectional user interfaces, in many implementations of interface devices 310. Each such listed term should not be narrowed by any implication from other terms in the same list but should instead be understood in its broadest reasonable interpretation as understood by those skilled in the art.

"Apparent," "automatic," "selective," "conditional," "indicative," "normal," "represented," "related," "partly," "responsive," "distilled," "local," "in a vicinity," "remote," "wireless," "periodic," "free," "aerial," "associated," "primary," "met," "passive," "implemented," "executable," "particular," "specific," "human," "performed," "impeded," "engaged," "earlier," "later," "detectable," "mobile," "of," "prior," "activated," "future," "light," "contemporaneous," "portable," "toward," or other such descriptors herein are used in their normal yes-or-no sense, not as terms of degree, unless context dictates otherwise. In light of the present disclosure those skilled in the art will understand from context what is meant by "vicinity," by being "in" or "at" a detection region, by "remote," and by other such positional descriptors used herein. "For" is not used to articulate a mere intended purpose in phrases like "circuitry for" or "instruction for," moreover, but is used normally, in descriptively identifying special purpose circuitry or code.

Some descriptions herein refer to a "distillation" of data. Such distillations can include an average, estimate, range, or other computation at least partly distilling a set of data. They can likewise include an indexing, sorting, summarization, distributed sampling, or other process having a purpose or effect of showing some aspect of the data more concisely or effectively than a conventional display or archiving of the entire data. Selecting a last portion of a data set can constitute a distillation, for example, in a context in which the data's utility apparently increases (medians or other cumulative computations, e.g.). Removing duplicative data or indexing available data are useful ways of "distilling" data so that it becomes manageable even while retaining some of its meaning. Those skilled in the art will recognize many useful modes of distilling data in light of the state of the art and of teachings herein.

In some embodiments, "signaling" something can include identifying, contacting, requesting, selecting, or indicating the thing. In some cases a signaled thing is susceptible to fewer than all of these aspects, of course, such as a task definition that cannot be "contacted."

In some embodiments, "status indicative" data can reflect a trend or other time-dependent phenomenon (indicating some aspect of an entity's condition, e.g.). Alternatively or additionally, a status indicative data set can include portions that have no bearing upon such status. Although some types of distillations can require authority or substantial expertise (e.g. making a final decision upon a risky procedure or other course of action), many other types of distillations can readily be implemented without undue experimentation in light of teachings herein.

In some embodiments, one or more applicable "criteria" can include maxima or other comparison values applied to durations, counts, lengths, widths, frequencies, signal magnitudes or phases, digital values, or other aspects of data characterization. In some contexts, such criteria can be applied by determining when or how often a recognizable pattern can be found: a text string, a quantity, a sound, an arrhythmia, a visible dilation, a failure to respond, a non-change, an allergic response, a symptom relating to an apparent condition of the user, or the like.

In some embodiments, "causing" events can include triggering, producing or otherwise directly or indirectly bringing the events to pass. This can include causing the events remotely, concurrently, partially, or otherwise as a "cause in fact," whether or not a more immediate cause also exists.

Some descriptions herein refer to an "indication whether" an event has occurred. An indication is "positive" if it indicates that the event has occurred, irrespective of its numerical sign or lack thereof, limited to patentable subject matter under 35 U.S.C. 101. Whether positive or negative, such indications may be weak (i.e. slightly probative), definitive, or many levels in between. In some cases the "indication" may include a portion that is indeterminate, such as an irrelevant portion of a useful photograph.

Figure 4:
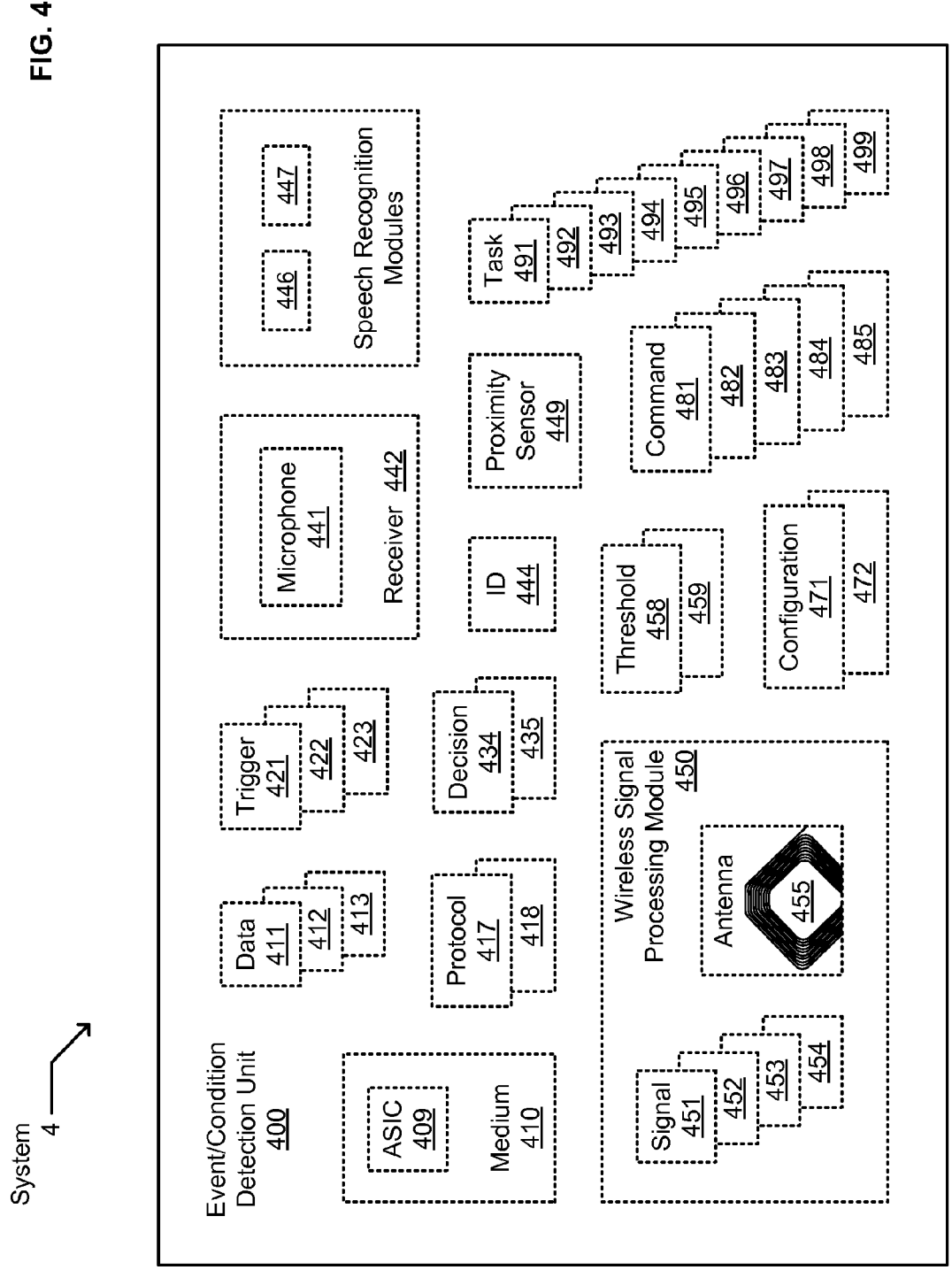
FIG. 4 depicts an exemplary environment featuring an event/condition detection unit.

FIG. 4 depicts another system 4 in which one or more technologies may be implemented. Event/condition detection unit 400 comprises special-purpose circuitry implemented as one or more application-specific integrated circuits (ASICs) 409 or other such data-handling media 410. Event/condition detection unit 400 may, in some variants, include one or more instances of data 411, 412, 413; hard-wired or other special-purpose protocols 417, 418; triggers 421, 422, 423; decisions 434, 435; microphones 441 or other receivers 442; identifiers 444; proximity sensors 449; wireless signal processing modules 450 (operable to handle one or more signals 451, 452, 453, 434 transmitted or received via antenna 455, e.g.); thresholds 458, 459; configurations 471, 472; commands 481, 482, 483, 484, 485; or tasks 491, 492, 493, 494, 495, 496, 497, 498, 499 (implemented in special-purpose circuitry or software executable by one or more processors 365, e.g.). In some variants, such commands 481-485 or tasks 491-499 may be received (from user 226, e.g.) via a microphone 441 and a speech recognition module 446, 447 or other such configurations of inputs 391. (In some embodiments, a "module" as described herein may include one or more of special-purpose circuitry or special-purpose device-executable code: code by which a processor 365 that is executing the code, for example, becomes a special-purpose machine.)

FIG. 5 depicts another system 5 in which one or more technologies may be implemented. An unmanned aerial device (UAD) 501 may travel among a sender 510 (of cargo to be delivered, e.g.), a station 520, and a destination 530 (of the cargo, e.g.) along travel paths 581, 582, 583 through the air 585 as shown. One or more media 195, 410 aboard UAD 501 may contain one or more identifiers 541 of cargo, identifiers 542 of destination 530, or identifiers 543 of the UAD 501 tasked with delivery. Such media may likewise contain other indicia of various planned or completed delivery tasks 491-499, such as a photograph 553 of an item of cargo (envelope 551, e.g.) having been delivered to a delivery site 552 (at destination 530, e.g.); a photograph 554 of a part of a recipient 555 or of an item of cargo (syringe 556, e.g.) being delivered to a destination (recipient 555, e.g.); addresses (of sender 510, station 520, or destination 530, e.g.); audio clips 563 (of recipient 555 refusing or accepting delivery, e.g.); or biometrics 564 (of sender 510 or recipient 555, e.g.). In some implementations, moreover, UAD 501 may implement or interact with one or more instances of interfaces 390 (having one or more buttons 561 thereon as inputs 391, e.g.) as described below.

With reference now to FIG. 15, shown is a high-level logic flow 15 of an operational process. Intensive operation 53 describes obtaining first data indicating that a first unmanned aerial device delivered a first item to a first entity (e.g. data acquisition module 138 receiving one or more addresses 562 or photographs 553 as data 411 indicating that one or more UAD's 501 delivered an envelope 551, signature document, or other article to a placement site 552 or other destination 530). This can occur, for example, in a context in which UAD 501 implements or interacts with primary unit 110, UAD 201, and event/condition detection unit 400 as described above. Alternatively or additionally, data 412 may include a biometric 564 (fingerprint, e.g.) or other manifestation of a recipient 555 receiving a medication (in a syringe 556 or capsule, e.g.) or other delivered material as described herein. Either such "first" data 411, 412 may likewise include one or more of an identifier 541 of the "first" item (envelope 551 or syringe 556, e.g.), an identifier 542 of the "first" entity (site 552 or recipient 555, e.g.), an identifier 543 (serial number or alias, e.g.) of the "first" UAD 201, 501 or other such indications signifying a successful delivery.

In light of teachings herein, numerous existing techniques may be applied for configuring special-purpose circuitry or other structures effective for dispatching a vehicle for making deliveries without undue experimentation or for configuring other decisions and devices as described herein. See, e.g., U.S. Pat. No. 8,140,592 ("Delivery operations information system with route adjustment feature and methods of use"); U.S. Pat. No. 8,041,649 ("Methods and systems for postcode-to-postcode delivery interval and routing calculation"); U.S. Pat. No. 7,947,916 ("Mail sorter system and method for moving trays of mail to dispatch in delivery order"); U.S. Pat. No. 7,868,264 ("System and process for reducing number of stops on delivery route by identification of standard class mail"); U.S. Pat. No. 7,739,202 ("Computer system for routing package deliveries"); U.S. Pat. No. 7,647,875 ("Seed hopper and routing structure for varying material delivery to row units"); U.S. Pat. No. 6,801,139 ("Method and system for delivering a time-efficient mobile vehicle route that encompasses multiple limited-duration events").

In light of teachings herein, numerous existing techniques may be applied for configuring special-purpose circuitry or other structures effective for data acquisition (relating to a delivery, e.g.) without undue experimentation or for configuring other decisions and devices as described herein. See, e.g., U.S. Pat. No. 8,111,819 ("Message server and method for notification of a user about the delivery of an electronic message"); U.S. Pat. No. 8,074,642 ("Visual indicator for an aerosol medication delivery apparatus and system"); U.S. Pat. No. 7,984,100 ("Email system automatically notifying sender status and routing information during delivery"); U.S. Pat. No. 7,713,229 ("Drug delivery pen with event notification means"); U.S. Pat. No. 7,559,456 ("Mail delivery indicator system"); U.S. Pat. No. 7,222,081 ("System and method for continuous delivery schedule including automated customer notification"); U.S. Pat. No. 6,902,109 ("Parcel delivery notice"); U.S. Pat. No. 6,859,722 ("Notification systems and methods with notifications based upon prior package delivery"); U.S. Pat. No. 6,535,585 ("System and method for notification upon successful message delivery"); U.S. Pat. No. 6,356,196 ("Verified receipt, notification, and theft deterrence of courier-delivered parcels").

In light of teachings herein, numerous existing techniques may be applied for configuring special-purpose circuitry or other structures effective for detecting and responding automatically to position data, optical data, auditory data, or other indications of a delivery without undue experimentation or for configuring other decisions and devices as described herein. See, e.g., U.S. Pat. No. 8,131,652 ("Residential delivery indicator"); U.S. Pat. No. 7,559,456 ("Mail delivery indicator system"); U.S. Pat. No. 7,483,721 ("Communication device providing diverse audio signals to indicate receipt of a call or message"); U.S. Pat. No. 7,346,662 ("Methods, systems, and products for indicating receipt of electronic mail"); U.S. Pat. No. 7,013,350 ("System setting flags based on address types in destination address field of a message to indicate different transports to deliver the message"); U.S. Pat. No. 7,006,013 ("System and method for visually indicating receipt of a radio communication directed to a uniquely identified vehicle").

In some embodiments described herein, a response (generating a decision, e.g.) to a stimulus is "conditional" if the stimulus can take on either a first possible value or a second possible value (or perhaps others) and in which the content (yes or no, e.g.) or occurrence of the response depends upon which of the possible stimuli are manifested. Likewise a response is "automatic" if it can occur (for at least one possible stimulus set, e.g.) without any human interaction.

Referring again to FIG. 15, extensive operation 84 describes transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device (e.g. data delivery module 153 transmitting a wireless signal 454 (radio frequency, e.g.) containing data 411, 412 indicating a delivery of the first item to the sender 510 of the first item). This can occur, for example, in a context in which data delivery module 153 receives such first data from data acquisition module 138; in which the first item comprises an envelope 551, syringe 556, material, or other such articles physically delivered by one or more UAD's 201, 501 to destination 530; in which such a UAD includes a data delivery module 153 configured to transmit such first data via a wireless signal path 581 (through air 585 or water vapor, e.g.); and in which sender 510 would otherwise be unwilling to entrust the item to be transferred via UAD 501. Alternatively or additionally, such a data delivery module 153 may be configured to transmit such first data indirectly (via a wireless signal path 583 through air 585 and through a station 520 that relays signal 454 to sender 510, e.g.). Alternatively or additionally, station 520 may include (an instance of) a data delivery module 153 configured to perform operation 84 by transmitting some or all such data 411, 412 wirelessly via path 582 as an automatic and conditional response to a suitable trigger 421. In respective embodiments, for example, a primary unit 110 may be configured to perform flow 15 such that trigger 421 comprises any of (1) UAD 501 delivering the first item to destination 530; (2) UAD 501 arriving at station 520 after having delivered the first item to destination 530; or (3) data delivery module 153 receiving an indication that UAD 201 delivered the first item to destination 530.

In light of teachings herein, numerous existing techniques may be applied for configuring special-purpose circuitry or other structures effective for deciding whether or not to route data through a free space medium without undue experimentation or for configuring other decisions and devices as described herein. See, e.g., U.S. Pat. No. 8,175,025 ("Wireless communication apparatus for selecting suitable transfer route on wireless network"); U.S. Pat. No. 8,099,060 ("Wireless/wired mobile communication device with option to automatically block wireless communication when connected for wired communication"); U.S. Pat. No. 8,090,132 ("Wireless communication headset with wired and wireless modes"); U.S. Pat. No. 8,081,967 ("Method to manage medium access for a mixed wireless network"); U.S. Pat. No. 8,040,864 ("Map indicating quality of service for delivery of video data to wireless device"); U.S. Pat. No. 7,899,027 ("Automatic route configuration in hierarchical wireless mesh networks"); U.S. Pat. No. 7,869,444 ("Mixed wireless and cabled data acquisition network"); U.S. Pat. No. 7,865,186 ("Method for operating wired and wireless phone services interconnectively"); U.S. Pat. No. 7,315,548 ("Method and apparatus for determining a route between a source node and a destination node in a wireless multihopping communication network"); U.S. Pat. No. 6,578,085 ("System and method for route optimization in a wireless internet protocol network"); U.S. Pat. No. 6,058,312 ("Automatic selecting apparatus for an optimum wireless communication route").

In light of teachings herein, numerous existing techniques may be applied for configuring special-purpose circuitry or other structures effective for mobile data delivery (deciding when to transmit data from or via a mobile device, e.g.) without undue experimentation or for configuring other decisions and devices as described herein. See, e.g., U.S. Pat. No. 8,200,223 ("Base station and data transfer method for transferring data when a mobile station performs a handover"); U.S. Pat. No. 7,865,212 ("Methods and apparatus for use in transferring user data between two different mobile communication devices using a removable memory card"); U.S. Pat. No. 7,359,346 ("Apparatus for controlling data transmission/reception between main system and remote system of BTS in mobile communication system"); U.S. Pat. No. 7,240,075 ("Interactive generating query related to telestrator data designating at least a portion of the still image frame and data identifying a user is generated from the user designating a selected region on the display screen, transmitting the query to the remote information system"); U.S. Pat. No. 7,107,064 ("Mobile communication device and method for determining whether to transmit position data"); U.S. Pat. No. 6,742,037 ("Method and apparatus for dynamic information transfer from a mobile target to a fixed target that tracks their relative movement and synchronizes data between them"); U.S. Pat. No. 6,694,177 ("Control of data transmission between a remote monitoring unit and a central unit"); U.S. Pat. No. 6,604,038 ("Apparatus, method, and computer program product for establishing a remote data link with a vehicle with minimal data transmission delay"); U.S. Pat. No. 6,591,101 ("Method of subscriber data control in a mobile communication network where subscriber data is transferred from a home mobile switching center to a destination mobile switching center").

Figure 6:
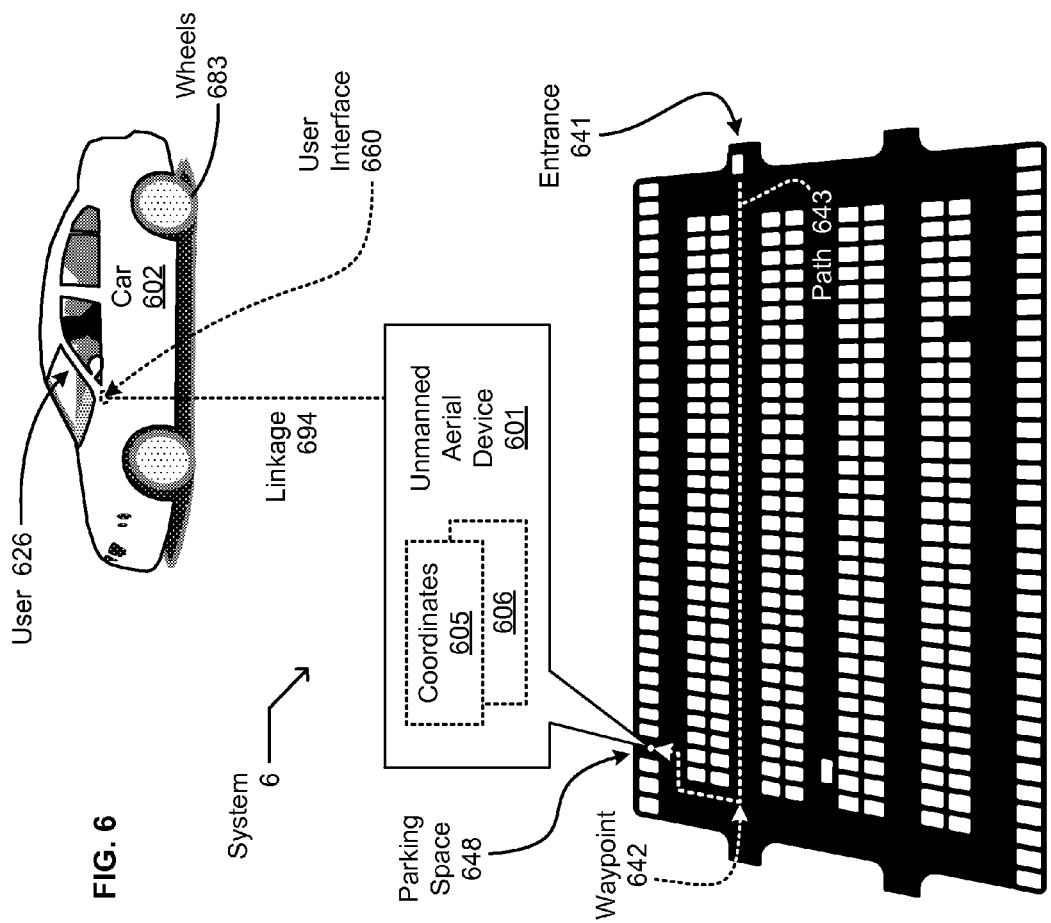
FIG. 6 depicts an exemplary environment featuring a UAD and another entity (a car or driver, e.g.) communicating about a resource (parking space, e.g.).

FIG. 6 depicts another system 6 in which one or more technologies may be implemented, one involving a passenger vehicle (car 602, e.g.) with wheels 683, pontoons, or other such support structures configured to facilitate transportation. As shown, car 602 is configured to bear at least one person (user 626, e.g.) and to include a user interface 660 (navigation system, e.g.). In a context in which such a passenger vehicle approaches an entrance 641 of a parking lot, UAD 601 may be configured (in association with the vehicle or with a zone comprising the parking lot, e.g.) to transmit to the vehicle information of interest. Such information can include coordinates 605, 606 (indicating an open parking space 648 or other location of interest, e.g.) or other positional information (indicating a recommended path 643 or waypoint 642 thereof, e.g.) transmitted via a wireless communication linkage 694.

Figure 16:
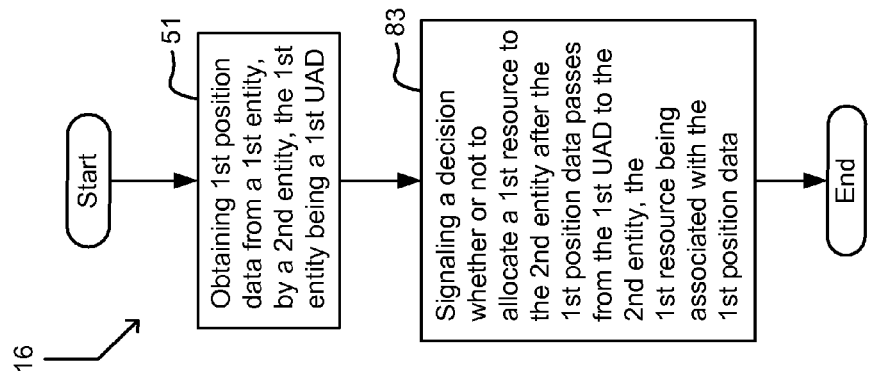
FIG. 16 depicts a high-level logic flow of an operational process described with reference to FIG. 6.

With reference now to FIG. 16, shown is a high-level logic flow 16 of an operational process. Intensive operation 51 describes obtaining first position data from a first entity, by a second entity, the first entity being a first unmanned aerial device (e.g. a coordinate communication module 136 resident in car 602 receiving two or more coordinates 605 from UAD 601 indicating the position of UAD 601). This can occur, for example, in a context in which UAD 601 implements one or more UAD's 201, 501 as described above; in which an instance of primary unit 110 is resident in one or both of the "first" and "second" entities; in which the "second" entity (car 602 or user 626, e.g.) has arrived at an entrance 641 of a crowded parking lot; in which UAD 601 has found and occupied a vacant parking space 648; and in which UAD 601 transmits its location (to a user interface 660 of the "second" entity, e.g.) via a wireless linkage 694 to assist a device or user (in finding and occupying the parking space 648, e.g.). In some contexts, the first UAD 601 may include an interface control module 141 configured to transmit turn-by-turn instructions, coordinates 605, or other such guidance, for example. See FIG. 17. Such guidance can, for example, lead a "second" device (UAD 202 or car 602, e.g.) or user 226, 626 thereof to a pickup or delivery site 552, an article or other material there, a person in a crowd, or other such resources and destinations having locations known to primary unit 110.

In light of teachings herein, numerous existing techniques may be applied for configuring special-purpose circuitry or other structures effective for coordinate communication (acquiring, transmitting, receiving, or using altitude or other positional coordinates, e.g.) without undue experimentation or for configuring other decisions and devices as described herein. See, e.g., U.S. Pat. No. 8,107,608 ("System and method for providing routing, mapping, and relative position information to users of a communication network"); U.S. Pat. No. 8,041,453 ("Method and apparatus for defining and utilizing product location in a vending machine"); U.S. Pat. No. 8,009,058 ("Tracking location and usage of a mechanical sub assembly (MSA) within an automated storage library utilizing a unique identifier associated with location coordinates of the MSA"); U.S. Pat. No. 7,819,315 ("Apparatus and method for providing product location information to customers in a store"); U.S. Pat. No. 7,705,714 ("Wheel position detecting device that performs dedicated local communication for each wheel and tire air pressure detecting device including the same"); U.S. Pat. No. 7,555,386 ("System and method for sharing position information using mobile communication system"); U.S. Pat. No. 6,609,317 ("Signs for display of store item location systems").

In light of teachings herein, numerous existing techniques may be applied for configuring special-purpose circuitry or other structures effective for locating particular individuals or other mobile targets without undue experimentation or for configuring other decisions and devices as described herein. See, e.g., U.S. Pat. No. 8,200,247 ("Confirming a venue of user location"); U.S. Pat. No. 8,106,746 ("Method, apparatus, and system for selecting and locating objects having radio frequency identification (RFID) tags"); U.S. Pat. No. 8,064,647 ("System for iris detection tracking and recognition at a distance"); U.S. Pat. No. 8,032,153 ("Multiple location estimators for wireless location"); U.S. Pat. No. 7,925,093 ("Image recognition apparatus"); U.S. Pat. No. 7,893,848 ("Apparatus and method for locating, identifying and tracking vehicles in a parking area"); U.S. Pat. No. 7,876,215 ("System and method for locating and notifying a mobile user of people having attributes or interests matching a stated preference"); U.S. Pat. No. 7,656,292 ("Flexible anti-theft pack for tracking and location"); U.S. Pat. No. 7,647,171 ("Learning, storing, analyzing, and reasoning about the loss of location-identifying signals"); U.S. Pat. No. 7,092,566 ("Object recognition system and process for identifying people and objects in an image of a scene"); U.S. Pat. No. 6,513,015 ("System and method for customer recognition using wireless identification and visual data transmission"); U.S. Pat. No. 6,219,639 ("Method and apparatus for recognizing identity of individuals employing synchronized biometrics").

In light of teachings herein, numerous existing techniques may be applied for configuring special-purpose circuitry or other structures effective for locating specific resources without undue experimentation or for configuring other decisions and devices as described herein. See, e.g., U.S. Pat. No. 8,194,975 ("Use of an intrinsic image in face recognition"); U.S. Pat. No. 7,659,835 ("Method and apparatus for recognizing parking slot by using bird's eye view and parking assist system using the same"); U.S. Pat. No. 7,480,394 ("Method and arrangement for recognizing objects in mail item images, their position and reading their postal information"); U.S. Pat. No. 6,592,033 ("Item recognition method and apparatus"); U.S. Pat. No. 6,373,982 ("Process and equipment for recognition of a pattern on an item presented"); U.S. Pat. No. 6,313,745 ("System and method for fitting room merchandise item recognition using wireless tag"); U.S. Pat. No. 6,121,916 ("Method and apparatus for recognizing stationary objects with a moving side-looking radar").

Referring again to FIG. 16, extensive operation 83 describes signaling a decision whether or not to allocate a first resource to the second entity after the first position data passes from the first unmanned aerial device to the second entity, the first resource being associated with the first position data (e.g. resource reservation module 156 confirming a reservation 376 of parking space 648 after coordinates 605 thereof arrive at user interface 660). This can occur, for example, in a context in which parking space 648 is the "first" resource; in which the "second" entity is identified as the driver (by name 351, e.g.) or as the car (by model 352 or license plate number 353, e.g.); in which UAD 601 and user interface 660 each contain an instance of primary unit 110; in which UAD 601 receives and announces one or more such identifiers (via a speaker, projector, or other output 122 of UAD 601, e.g.) to passersby; in which user 626 enters the decision by indicating whether or not to associate the "first" resource with an identifier 355 of the second entity via input 121 of user interface 660; and in which user 626 would otherwise be unable to reserve the resource before happening across it. In other applications of flow 16, such "first" resources may include a cashier or other living entity; a public table or other space; a power or network connection; an item for sale or other object; or other such resources that a device can deem available for allocation under conditions as described herein. Moreover such "second" entities may include UAD's or other devices or people as described herein (identified by entity identification module 143, e.g.).

In light of teachings herein, numerous existing techniques may be applied for configuring special-purpose circuitry or other structures effective for entity identification (associating a specific identifier with a device, user, group, or other entity, e.g.) without undue experimentation or for configuring other decisions and devices as described herein. See, e.g., U.S. Pat. No. 8,176,156 ("Server identification assignment in a distributed switched storage environment"); U.S. Pat. No. 8,136,025 ("Assigning document identification tags"); U.S. Pat. No. 7,970,426 ("Method of assigning provisional identification to a subscriber unit and group"); U.S. Pat. No. 7,877,515 ("Identity assignment for software components"); U.S. Pat. No. 7,495,576 ("Modular electronic sign and method of assigning a unique identifier to common modules of said sign"); U.S. Pat. No. 7,383,174 ("Method for generating and assigning identifying tags to sound files"); U.S. Pat. No. 6,721,761 ("System for assigning digital identifiers to telephone numbers and IP numbers"); U.S. Pat. No. 6,430,182 ("Fabric system and method for assigning identifier for fabric apparatus therefor"); U.S. Pat. No. 6,283,227 ("Downhole activation system that assigns and retrieves identifiers"); U.S. Pat. No. 6,114,970 ("Method of assigning a device identification"); U.S. Pat. No. 6,091,738 ("Transmission-equipment and method for assigning transmission-equipment identification number in transmission system").

In light of teachings herein, numerous existing techniques may be applied for configuring special-purpose circuitry or other structures effective for resource reservation (associating an entity identifier with a living or other resource, e.g.) without undue experimentation or for configuring other decisions and devices as described herein. See, e.g., U.S. Pat. No. 8,166,484 ("System for confirming and cancelling tentative resource reservation within the valid time indicates period during which the tentative reservation request is valid"); U.S. Pat. No. 8,160,906 ("System and method for improved rental vehicle reservation management"); U.S. Pat. No. 8,150,403 ("Reservation of mobile station communication resources"); U.S. Pat. No. 8,117,051 ("Method for determining the number of available transport seats in a computerized reservation system"); U.S. Pat. No. 8,065,287 ("Method and system for searching availability of an entity for purchase or reservation"); U.S. Pat. No. 7,956,769 ("Method and system for reservation-based parking"); U.S. Pat. No. 7,818,190 ("Camping reservation system, method and program"); U.S. Pat. No. 7,783,530 ("Parking reservation systems and related methods"); U.S. Pat. No. 7,783,506 ("System and method for managing reservation requests for one or more inventory items"); U.S. Pat. No. 7,693,779 ("Method and system for requesting a reservation for a set of equity instruments to be offered"); U.S. Pat. No. 7,634,426 ("Golf reservation system"); U.S. Pat. No. 7,548,866 ("Individual seat selection ticketing and reservation system").

Figure 7:
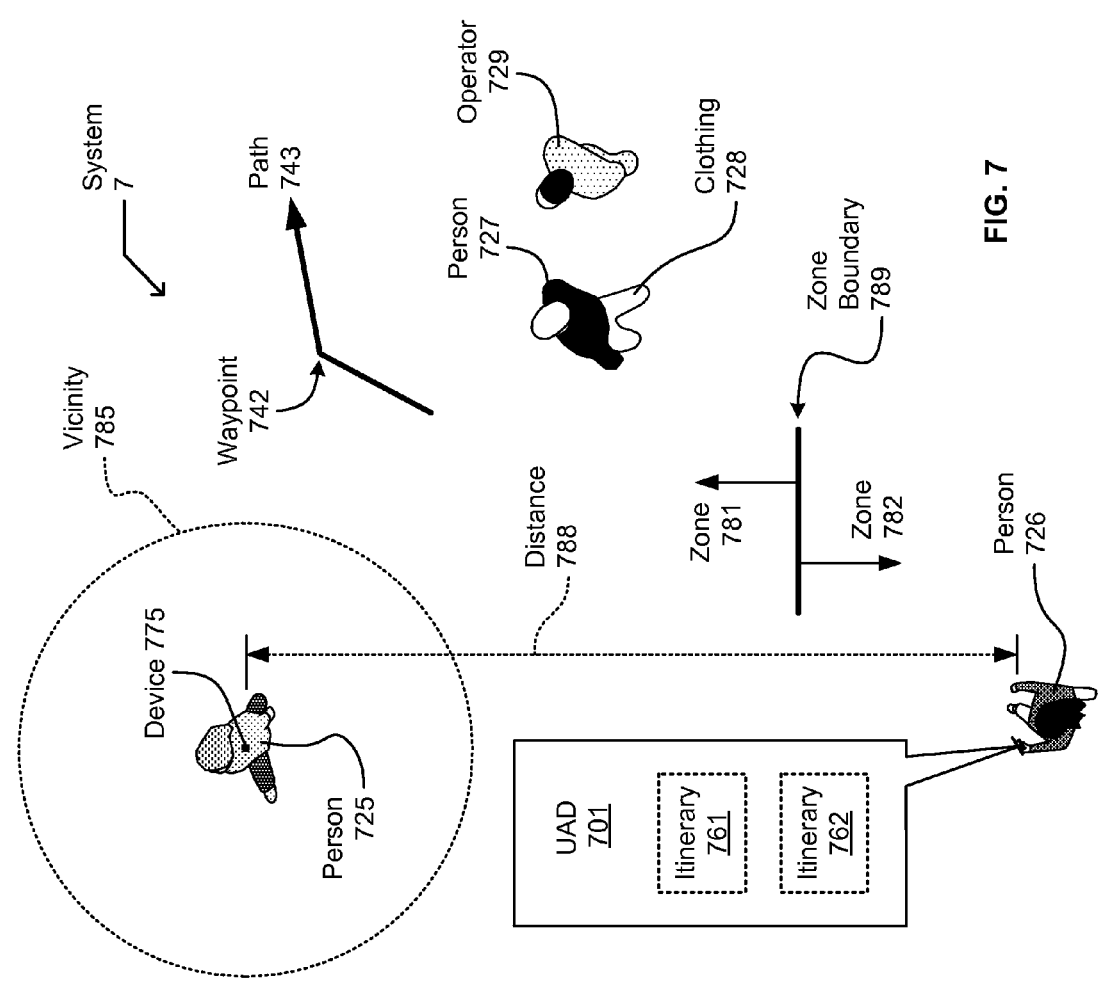
FIG. 7 depicts an exemplary environment featuring three pedestrians in one zone, one pedestrian in another zone, and at least one handheld UAD.

FIG. 7 depicts another system 7 in which one or more technologies may be implemented, depicting a view from above of several people 725, 726, 727 near a zone boundary 789 dividing two zones 781, 782 (areas of land, e.g.). Person 726 is shown carrying an unmanned aerial device 701 containing itineraries 761, 762 (in a memory 395 or other medium 195 thereof, e.g.) in one or more contexts further described below. In one context, person 726 is walking, and UAD 701 is traveling, toward a person 725 or device 775 that is currently a distance 788 away. In another, the destination 530 is defined as a vicinity 785 (a detection range of a proximity sensor 449, e.g.) of such a device 775. In another context, UAD 701 is guiding person 726 generally along a static or dynamic path 743 comprising a waypoint 742. In yet another context, a subject (person 727, e.g.) has one or more attributes (clothing 728 or voice or face or other biometric 564, e.g.) susceptible of automatic recognition by one or more stationary event/condition detection units 400 or other recognition modules (aboard a UAD 701 or other portable device 775, e.g.). See FIG. 14.

Figure 17:
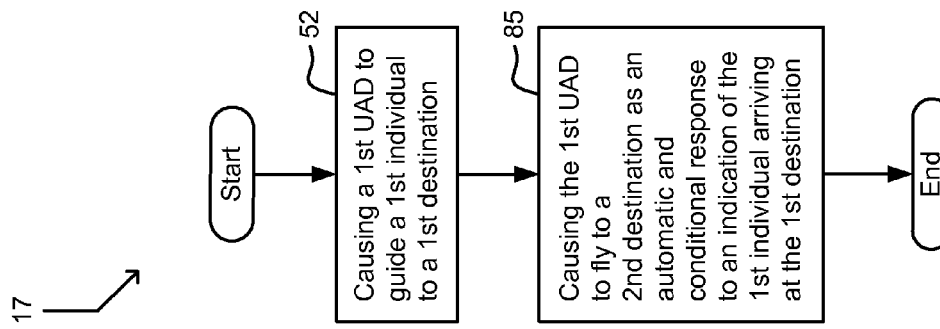
FIG. 17 depicts a high-level logic flow of an operational process described with reference to FIG. 7.

With reference now to FIG. 17, shown is a high-level logic flow 17 of an operational process. Intensive operation 52 describes causing a first unmanned aerial device to guide a first individual to a first destination (e.g. interface control module 141 causing a display, speaker, or other output 392 of unmanned aerial device 701 to provide navigational instruction 397 effective for guiding person 726 according to a first itinerary 761). This can occur, for example, in a context in which the first destination is a vicinity 785 of a person 725 or of a portable device 775; in which the first destination is also a non-stationary component of the first itinerary 761 (indicating such a person 725, device 775, or other destination, e.g.); in which person 726 is the "first" individual, who may be traveling through a zone 782 in which conventional GPS navigation devices cannot be used; and in which person 726 would otherwise have to find the "first" destination without any device assistance. On a cruise ship or tightly managed facility in which an owner (of zone 782, e.g.) does not provide a public wireless connectivity (cell tower access, e.g.) or in which individuals are not permitted to bring their own wireless devices onsite, for example, the owner may lend such UAD's 701 to visitors for authorized uses (finding a stationary or other destination 530 within or across a controlled zone 782, e.g.). Alternatively, in some variants, a flight control module 151 may perform operation 52 by flying ahead of the first individual (user 626, e.g.) slow enough to be followed. This can occur, for example, in a context in which itinerary 761 defines the first destination (parking space 648, e.g.) and in which flight control module 151 is configured to respond to a microphone, accelerometer, camera, or other input 391 of a "first" UAD signaling such flying guidance. For example, flight control module 151 may be configured to cause the first UAD to maintain a suitable lead distance (on the order of 1-3 meters, e.g.) of the first individual in some contexts, landing or otherwise slowing down as necessary if the individual follows slowly, moving laterally or backward if the individual moves orthogonally to or opposite to the first UAD's current or next direction of travel, giving up (and returning to a kiosk 250 or other "home" station, e.g.) if the individual stops following for a period of time exceeding a threshold (on the order of 1 or 60 seconds, e.g.).

Alternatively or additionally, an instance of flight control module 151 aboard UAD 701 may be configured (by including a microphone 441 operatively coupled to a speech recognition module 446, e.g.) to recognize and conditionally follow one or more commands given by the first person ("stay with me" or "fly away" e.g.). In some variants, for example, such a command 482 of "stay with me" can conditionally cause an override or modification of a default configuration of flight control module 151 so that flight control module 152 is temporarily disabled or so that itinerary 762 is suspended until after speech recognition module 446 detects and signals the "fly away" command 483 (to one or more flight control modules 151, 152, e.g.). This can occur, for example, in a context in which the latter event defines an alternative trigger 422 causing the first UAD to fly to a "home" station (or a "second" destination, e.g.) defined by itinerary 762 under the control of flight control module 152.

In light of teachings herein, numerous existing techniques may be applied for configuring special-purpose circuitry or other structures effective for interface control (remotely or locally controlling how an interface handles user input or output, e.g.) without undue experimentation or for configuring other decisions and devices as described herein. See, e.g., U.S. Pat. No. 8,201,143 ("Dynamic mating of a modified user interface with pre-modified user interface code library"); U.S. Pat. No. 8,198,568 ("Input sensitive user interface"); U.S. Pat. No. 8,185,483 ("System for design and use of decision models"); U.S. Pat. No. 8,184,070 ("Method and system for selecting a user interface for a wearable computing device"); U.S. Pat. No. 8,181,119 ("User interface with inline customization"); U.S. Pat. No. 8,171,460 ("System and method for user interface automation"); U.S. Pat. No. 8,171,394 ("Methods and systems for providing a customized user interface for viewing and editing metadata"); U.S. Pat. No. 8,165,567 ("Method and system for customizing user interface by editing multimedia content"); U.S. Pat. No. 8,151,201 ("User interface manager and method for reacting to a change in system status"); U.S. Pat. No. 8,127,233 ("Remote user interface updates using difference and motion encoding"); U.S. Pat. No. 8,122,365 ("System and method for dynamic creation and customization of a user interface in a web service environment"); U.S. Pat. No. 7,908,221 ("System providing methods for dynamic customization and personalization of user interface").

Referring again to FIG. 17, extensive operation 85 describes causing the first unmanned aerial device to fly to a second destination as an automatic and conditional response to an indication of the first individual arriving at the first destination (e.g. flight control module 152 causing a "first" UAD 701 to fly to a kiosk 250 or other station 520 as an implementation of an itinerary 762 triggered by the first UAD arriving at the first destination). This can occur, for example, in a context in which the first UAD implements one or more primary units 110 or interface devices 310; in which the "second" destination comprises the kiosk 250 or other station 520; in which a proximity sensor 449 or other such input 121 (operatively coupled to a flight control module 152 of device 775, e.g.) detects that UAD 701 is in a vicinity 785 of device 775 (as the indication of the first individual arriving at the first destination, e.g.); and in which person 726 would otherwise have to instruct UAD 701 what to do after arriving. In some variants, for example, such an input 121 may include a wireless signal processing module 450 configured to transmit a first wireless signal 451 and receive a second wireless signal 452 (echo, e.g.) responsive thereto, the wireless signals 451, 452 jointly manifesting a delay indicative of a distance 788 between the devices so that a signal 453 derived therefrom indicates the first UAD arriving "at" the first destination as the derived signal 453 crossing a threshold 458, the flight control module 152 being operatively coupled to wireless signal processing module 450 and responsive to such crossing. Alternatively or additionally, network 190 may include an event/condition detection unit 400 implemented in UAD 701. In some variants, moreover, one or more additional flight control modules 152 may be configured to perform one or more variants of operation 85 (causing the 1st UAD to fly to a 3nd destination as an automatic and conditional response to an indication of the first individual arriving at the 2nd destination or to some other indication of the first UAD arriving at the 2nd destination, e.g.).

In light of teachings herein, numerous existing techniques may be applied for configuring special-purpose circuitry or other structures effective for flight control (using one or more remote or on-board controllers to cause an aerial device to implement a user-specified or autonomously selected route or itinerary, e.g.) without undue experimentation or for configuring other decisions and devices as described herein. See, e.g., U.S. Pat. No. 8,186,589 ("UAV decision and control system"); U.S. Pat. No. 8,100,366 ("Automatic kite flight control system"); U.S. Pat. No. 8,074,941 ("Aircraft flight control"); U.S. Pat. No. 7,962,252 ("Self-contained avionics sensing and flight control system for small unmanned aerial vehicle"); U.S. Pat. No. 7,502,684 ("Method and system for the automatic piloting of an aircraft on the approach to an airdrop position"); U.S. Pat. No. 7,431,243 ("Guidance and control for an autonomous soaring UAV"); U.S. Pat. No. 7,130,741 ("Navigating a UAV with a remote control device"); U.S. Pat. No. 6,926,233 ("Automatic formation flight control system (AFFCS)—a system for automatic formation flight control of vehicles not limited to aircraft, helicopters, or space platforms"); U.S. Pat. No. 6,856,894 ("Navigating a UAV under remote control and manual control with three dimensional flight depiction"); U.S. Pat. No. 6,847,856 ("Method for determining juxtaposition of physical components with use of RFID tags"); U.S. Pat. No. 6,497,600 ("Automatic pilot system for model aircraft").

Figure 8:
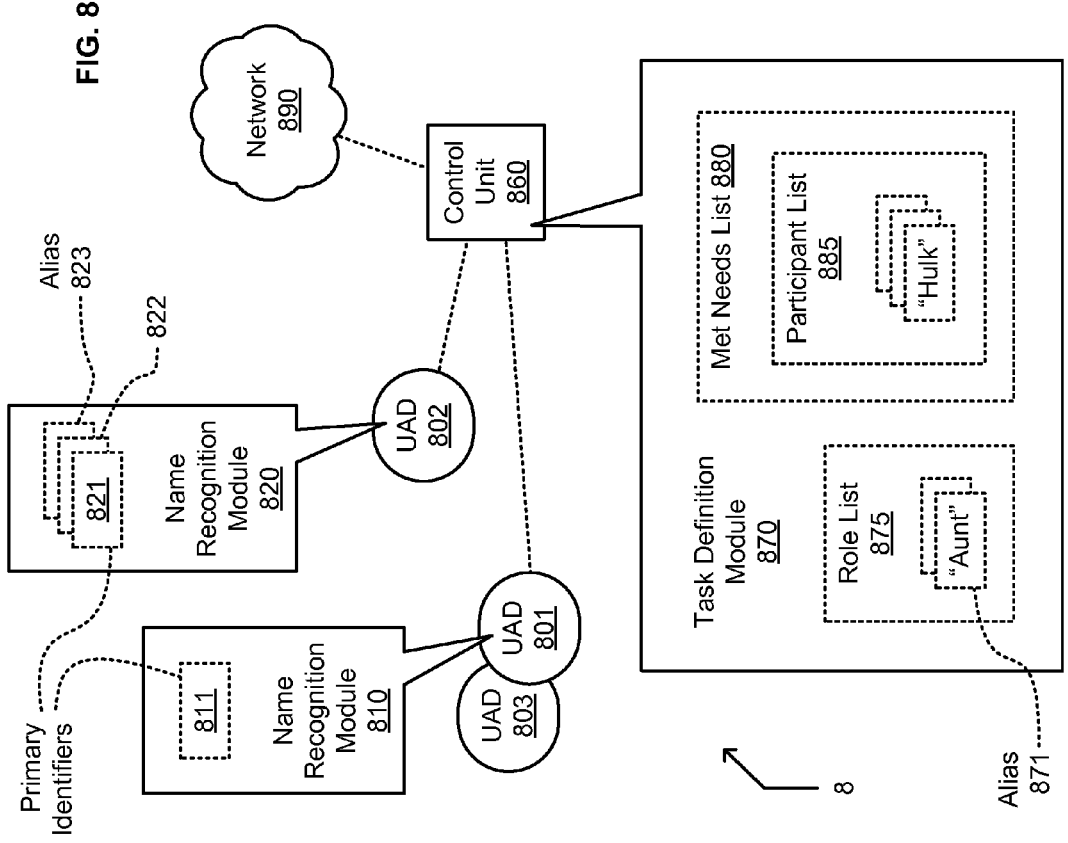
FIG. 8 depicts an exemplary environment featuring UAD's operably coupled with a network.

Another system 8 in which one or more technologies may be implemented is shown in FIG. 8, depicting a view of several unmanned aerial devices (UAD's) 801, 802, 803 configured to communicate with a control unit 860 on a network 890. Task definition module 870 (residing in control unit 860, e.g.) may include one or more aliases 871 in a role list 875 (identifying one or more unmet needs of a task 491-499, e.g.) and one or more aliases ("Hulk," e.g.) in a participant list 885 or other met needs list 880 of the task or job. UAD 801 comprises a name recognition module 810 configured to recognized a primary identifier 811 of UAD 801. UAD 802 comprises a name recognition module 820 configured to recognized a primary identifier 821 of UAD 802 as well as one or more aliases 822, 823 of UAD 802. (In some embodiments, one or more aliases or other identifiers "of" a device may also refer to a specific circuit or virtual entity at least partly aboard the device.)

Figure 18:
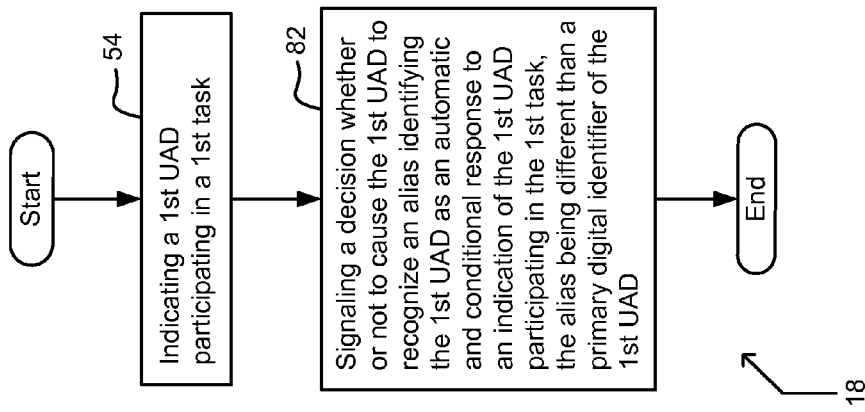
FIG. 18 depicts a high-level logic flow of an operational process described with reference to FIG. 8.

With reference now to FIG. 18, shown is a high-level logic flow 18 of an operational process. Intensive operation 54 describes indicating a first unmanned aerial device participating in a first task (e.g. enlistment module 133 generating a confirmation 381 that UAD 801 will participate in a delivery task 491 being coordinated by control unit 860). This can occur, for example, in a context in which one or more networks 190, 890 comprise interface device 310; in which control unit 860 and UAD's 801, 802, 803 may each contain (a respective instance of) primary unit 110, each optionally including event/condition detection unit 400; in which (an instance of) enlistment module 133 resides in control unit 840 and transmits an invitation 374 to UAD 801 to participate in one or more tasks 491-499; and in which UAD 801 transmits a timely acceptance 393 of the invitation 374. Alternatively or additionally, one or more enlistment modules 134 (resident in UAD 801, e.g.) may be configured to identify tasks 491, 492 suitable for UAD 801 to participate in and may transmit one or more requests 373 for such participation (to control unit 860, e.g.). This can occur, for example, in which enlistment module 133 is configured to perform an instance of operation 54 by transmitting an acceptance 394 of request 373. In some contexts, such requests 373 and invitations 374 (in an instance of network 190 that includes several UAD's 801, 802, 803 as described above, e.g.) may include a temporal threshold 459 expressing a deadline at or before which the request or invitation recipient must respond (as an expiration time of the request or invitation after which no acceptance of such request 373 or invitation 374 would be valid, e.g.). Alternatively or additionally, in the absence of such expression, one or more enlistment modules 133, 134 may be configured to apply a default deadline (within 1-2 orders of magnitude of a millisecond or a second after such transmission, e.g.), after which such recruitment subtask may be deemed unsuccessful.

In light of teachings herein, numerous existing techniques may be applied for configuring special-purpose circuitry or other structures effective for device enlistment (enabling or otherwise causing one or more available devices to participate in one or more suitable tasks, e.g.) without undue experimentation or for configuring other decisions and devices as described herein. See, e.g., U.S. Pat. No. 8,151,272 ("Optimized usage of collector resources for performance data collection through even task assignment"); U.S. Pat. No. 8,128,484 ("Game system generating second game according to game result of a device and allowing other devices to participate in second game thus generated"); U.S. Pat. No. 8,051,764 ("Fluid control system having selective recruitable actuators"); U.S. Pat. No. 7,948,447 ("Mobile display"); U.S. Pat. No. 7,864,702 ("Control and recruitment of client peripherals from server-side software"); U.S. Pat. No. 7,406,515 ("System and method for automated and customizable agent availability and task assignment management"); U.S. Pat. No. 7,308,472 ("System allowing data input device to request management server to assign a data input job to itself"); U.S. Pat. No. 6,975,820 ("Device control using job ticket scoring"); U.S. Pat. No. 6,493,581 ("System and method for rapid recruitment of widely distributed easily operated automatic external defibrillators").

Referring again to FIG. 18, extensive operation 82 describes signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device (e.g. control unit 860 transmitting a command 481 that configures name recognition module 810 to respond to an alias 871 of "Aunt" as an automatic and conditional response to control unit 860 receiving an acceptance or confirmation 381 indicating that UAD 801 will participate in delivery task 491). This can occur, for example, in a context in which "Aunt" is not a primary identifier 811 (serial number or Internet Protocol address, e.g.) that UAD 801 ordinarily responds to and in which name recognition module 810 was previously configured not to respond to "Aunt"; in which a name recognition module 820 of UAD 802 responds to an alias 822 of "Hulk" pursuant to the same delivery task 491; in which a primary identifier 821 of UAD 802 is neither "Hulk" nor "Aunt"; in which enlistment module 133 also causes alias 871 to be transferred into a participant list 885 of the delivery task 491 (in a met needs list 880 thereof, e.g.) that grows with each successful recruitment; and in which the primary digital identifier would otherwise have to be used throughout the task in addressing UAD 801. Alternatively or additionally, a primary unit 110 (residing in station 520, e.g.) remotely controlling UAD 801 may include a name recognition module 146 configured to perform operation 84 (pursuant to a successful recruitment as described above, e.g.).

In light of teachings herein, numerous existing techniques may be applied for configuring special-purpose circuitry or other structures effective for name recognition (determining whether an incoming signal is addressing an entity by comparing a component of the incoming signal against one or more names of the entity, e.g.) without undue experimentation or for configuring other decisions and devices as described herein. See, e.g., U.S. Pat. No. 8,135,764 ("Configuration management server, name recognition method and name recognition program"); U.S. Pat. No. 7,865,356 ("Method and apparatus for providing proper or partial proper name recognition"); U.S. Pat. No. 7,822,988 ("Method and system for identity recognition"); U.S. Pat. No. 7,792,837 ("Entity name recognition"); U.S. Pat. No. 7,370,078 ("Determining a remote device name"); U.S. Pat. No. 6,052,682 ("Method of and apparatus for recognizing and labeling instances of name classes in textual environments").

Figure 9:
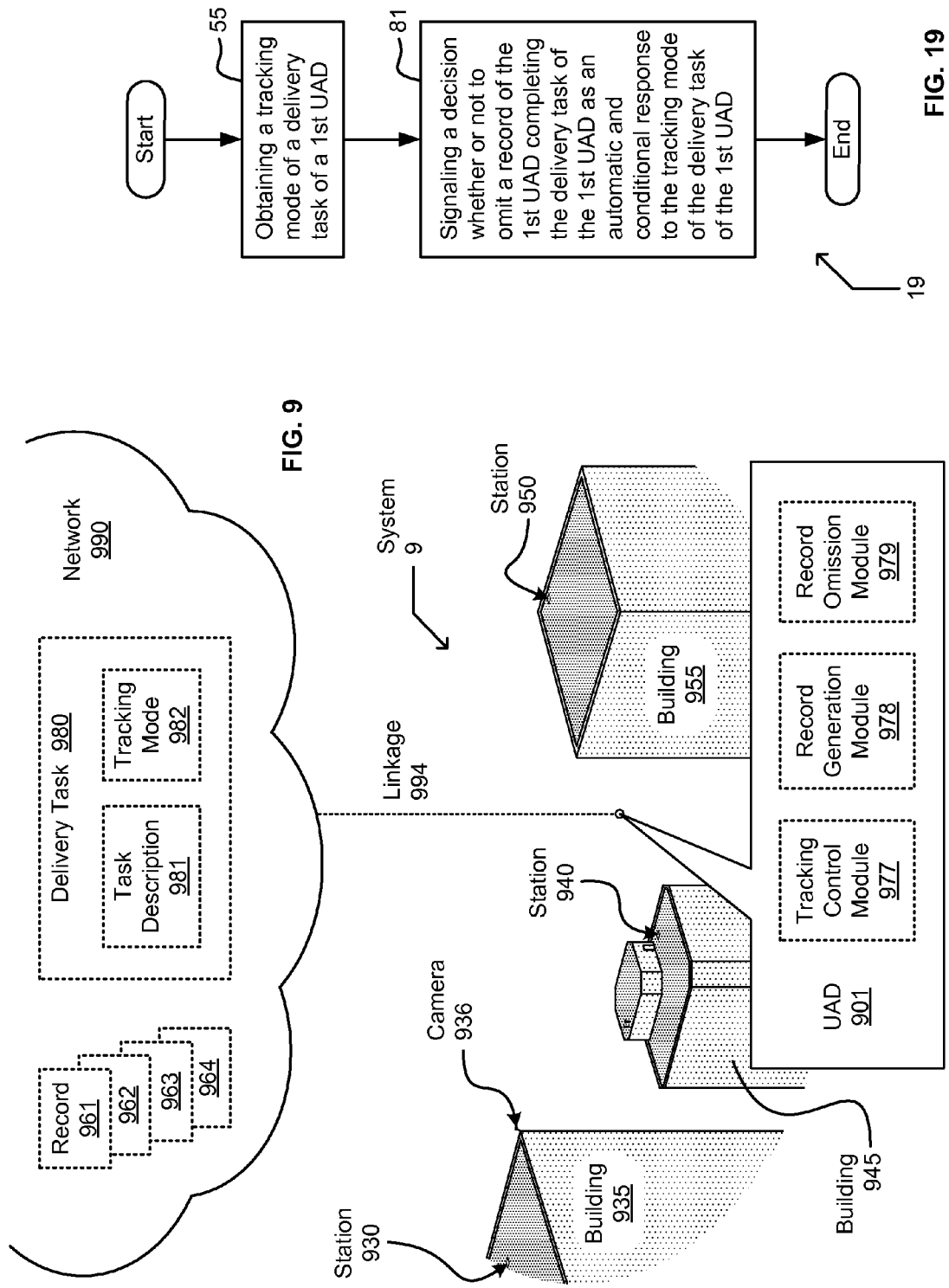
FIG. 9 depicts an exemplary environment featuring a UAD traveling among several stations.

Another system 9 in which one or more technologies may be implemented is shown in FIG. 9, depicting UAD 901 (comprising primary unit 110, e.g.) operably connected with one or more networks 190 (comprising network 990, e.g.) via a wireless communication linkage 994. Network 990 includes (a memory 395 or other data handling medium 195 containing) one or more records 961, 962, 963, 964, some of which may (optionally) include digitally represented delivery tasks 980 or other tasks 491-499, each of which may (optionally) comprise one or more instances of task descriptions 981 or tracking modes 982 as shown. UAD 901 may (optionally) include one or more instances of tracking control modules 977; record generation modules 978, or record omission modules 979. In some contexts, UAD 901 (implementing UAD 501, e.g.) may be configured to fly (along respective paths 581, 582, 583, e.g.) among two or more stations 930, 940, 950 (e.g. on respective buildings 935, 945, 955), some or all of which may be observable by a stationary or pivotable camera 936 (in a configuration like systems 3-8 described above, e.g.).

With reference now to FIG. 19, shown is a high-level logic flow 19 of an operational process. Intensive operation 55 describes obtaining a tracking mode of a delivery task of a first unmanned aerial device (e.g. tracking control module 977 receiving a tracking mode 982 of zero pertaining to a delivery task 980 that has been assigned to UAD 901). This can occur, for example, in a context in which a task description 981 of delivery task 980 indicates a physical delivery of a "first" item (envelope 551, e.g.) to station 940; in which UAD 901 implements a primary unit 110 that includes data acquisition module 138; in which one or more just-completed task 493 involved UAD 901 visiting station 950; in which a tracking mode 982 of zero corresponds to a delivery protocol 417 by which the specific item is delivered in lieu of operation 53 (without notifying a provider of an item delivered, e.g.); and in which tracking control module 977 would otherwise trigger data acquisition module 138 to obtain at least some delivery-indicative data 411-413 in response to the item being delivered to station 940 (by performing operation 53, e.g.). See FIG. 15. In some variants, for example, task 493 may include one or more instances of delivery tasks 494, pickup tasks 495, recharge tasks 496, reconfiguration tasks 497, or data transfer tasks 498. In some variants, for example, UAD 901 downloads each successive task in a resting state after completing the prior task. Alternatively or additionally, tracking control module 977 may be configured to implement a default tracking mode 361—indicating at least one of the first item(s) or UAD(s), e.g.—for each task 494-499 except when that task specifies an alternative tracking mode (such as a brief mode 362 or user-defined mode 363, e.g.).

In some variants, one or more instances of tracking control module 148 resident in network 990 may be configured to perform operation 55. This can occur, for example, in a context in which the first UAD 901 does not have any on-board capability of performing operation 55 or is currently configured not to perform operation 55; in which network 990 contains one or more instances of primary unit 110 (resident in a "second" UAD 202 or tower-based station 520, e.g.); and in which tracking control module 148 receives tracking mode 982 as a component of a delivery task 980 assigned to the first UAD 901.

In light of teachings herein, numerous existing techniques may be applied for configuring special-purpose circuitry or other structures effective for tracking control (identifying and updating how increments of task progress are documented, e.g.) without undue experimentation or for configuring other decisions and devices as described herein. See, e.g., U.S. Pat. No. 8,179,261 ("Identification and surveillance device, system and method for individual item level tracking"); U.S. Pat. No. 8,179,253 ("Location and tracking system, method and device using wireless technology"); U.S. Pat. No. 8,135,171 ("Multipoint tracking method and related device"); U.S. Pat. No. 8,115,625 ("Parental alert and child tracking device which determines if a child has deviated from a predicated travel route"); U.S. Pat. No. 8,014,917 ("Apparatus for tracking and recording vital signs and task-related information of a vehicle to identify operating patterns"); U.S. Pat. No. 7,978,065 ("Device, system and method for tracking mobile assets"); U.S. Pat. No. 7,951,046 ("Device, method and computer program product for tracking and monitoring an exercise regimen"); U.S. Pat. No. 7,451,445 ("Mechanism for tracking the execution progress of a parent task which spawns one or more concurrently executing child tasks"); U.S. Pat. No. 7,401,030 ("Method and system for tracking disposition status of an item to be delivered within an organization"); U.S. Pat. No. 6,604,124 ("Systems and methods for automatically managing work flow based on tracking job step completion status"); U.S. Pat. No. 6,463,420 ("Online tracking of delivery status information over a computer network").

Referring again to FIG. 19, extensive operation 81 describes signaling a decision whether or not to omit a record of the first unmanned aerial device completing the delivery task of the first unmanned aerial device as an automatic and conditional response to the tracking mode of the delivery task of the first unmanned aerial device (e.g. selective retention module 158 implementing either a decision 434 to deactivate record generation module 978 temporarily or a decision 435 to cause record generation module 978 to generate a record 961 of "first" UAD 901 having made such a delivery by configuring record generation module 978 before UAD 901 approaches building 945). This can occur, for example, in a context in which decision 435 is "implemented" by a selective retention module 158 (resident in network 990, e.g.) transmitting (to record generation module 978, e.g.) either (1) a Boolean expression ("yes," e.g.) indicating that a user has requested one or more records 961-963 of the delivery or (2) an identifier 444 of which tracking mode 361-363 to use in such acquisition. Alternatively or additionally, decision 435 may be implemented by causing record generation module 978 to be transmitted to or updated aboard UAD 901. Likewise a decision 434 "to omit a record" may be "implemented" by selective retention module 158 causing a selective deletion of record 961 (of UAD 901 delivering the "first" item to station 940, e.g.) before one or more similar records 962-964 (relating to other tasks, e.g.) are transmitted from UAD 901 to network 990 (in a batch transfer, e.g.). This can occur, for example, in a context in which a data acquisition module 139 residing in UAD 901 generates and holds at least one photograph 553, 554 or other record 961-963 for each delivery aboard UAD 901 (in a memory 395 or other data-handling medium 195 thereof, e.g.); in which record omission module 979 selectively deletes a subset of such records 961-963 identified by selective retention module 158; and in which a remainder (comprising record 962, e.g.) of such records is later transmitted to network 990. In other contexts a selective retention module 158 resident in network 990 can implement a decision to omit such a record 961 of the delivery task completion (from a data transmission to a station 520 outside network 990, e.g.) by explicitly listing (a) one or more records 962-963 to be included in such transmission or (b) one or more records 961 to be excluded from such transmission. This can occur, for example, in a context in which UAD 901 implements primary unit 110 and one or more of the above-described UAD's and in which either (1) unwanted tracking of delivery task 980 would occur or (2) UAD 901 would be unable to track a completion of other potentially available tasks 491-499.

In light of teachings herein, numerous existing techniques may be applied for configuring special-purpose circuitry or other structures effective for selective event tracking without undue experimentation or for configuring other decisions and devices as described herein. See, e.g., U.S. Pat. No. 8,219,572 ("System and method for searching enterprise application data"); U.S. Pat. No. 8,165,932 ("Enhancement of network accounting records"); U.S. Pat. No. 8,019,771 ("Method for dynamically finding relations between database tables"); U.S. Pat. No. 7,922,088 ("System and method to automatically discriminate between different data types"); U.S. Pat. No. 7,903,839 ("Method for canceling impact of physical property variability on image quality performance of digital imaging system"); U.S. Pat. No. 7,883,013 ("Mobile image capture and processing system"); U.S. Pat. No. 7,870,012 ("Method for managing a workflow process that assists users in procurement, sourcing, and decision-support for strategic sourcing"); U.S. Pat. No. 7,835,971 ("Method and system configured for facilitating management of international trade receivables transactions"); U.S. Pat. No. 7,792,808 ("More efficient search algorithm (MESA) using virtual search parameters"); U.S. Pat. No. 7,769,644 ("Bill of lading transmission and processing system for less than a load carriers"); U.S. Pat. No. 7,739,096 ("System for extraction of representative data for training of adaptive process monitoring equipment"); U.S. Pat. No. 7,733,223 ("Effectively documenting irregularities in a responsive user's environment"); U.S. Pat. No. 7,631,065 ("System, method and computer program product for merging data in a network-based filtering and aggregating platform"); U.S. Pat. No. 7,496,670 ("Digital asset monitoring system and method"); U.S. Pat. No. 7,467,122 ("System for aiding the design of product configuration"); U.S. Pat. No. 7,394,817 ("Distributed data caching in hybrid peer-to-peer systems"); U.S. Pat. No. 7,346,675 ("System, method and computer program product for contract-based aggregation"); U.S. Pat.

No. 7,142,110 ("Automatic conditioning of data accumulated by sensors monitoring supply chain processes").

Figure 10:
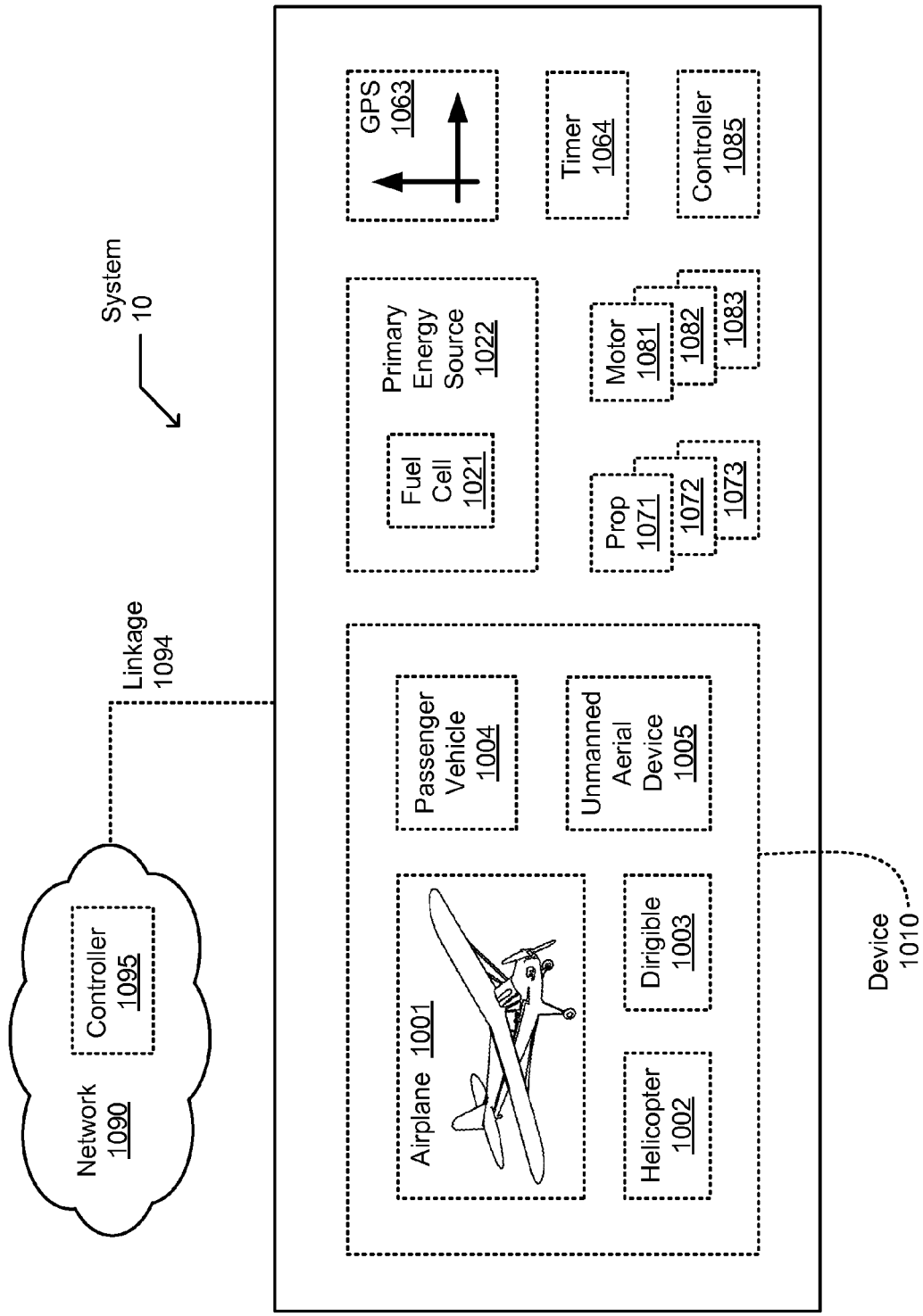
FIG. 10 depicts an exemplary environment featuring a device (UAD, e.g.) operably coupled with a network via a communication linkage.

FIG. 10 depicts another context in which one or more of the above-described systems may be implemented. System 10 comprises one or more instances of participating mobile devices 1010 such as airplanes 1001, helicopters 1002, or dirigibles 1003. Each such mobile device 1010 may, moreover, comprise a passenger vehicle 1004 (like a car 602 or passenger airplane, e.g.), a handheld device (like a cellular telephone or UAD 201, UAD 202 of FIG. 2, e.g.), or another unmanned aerial device 1005 (such as a glider, balloon, rocket, helicopter 1002, dirigible 1003, or other such device configured to be maneuvered in flight, e.g.). In some contexts, moreover, such a device may include one or more instances of fuel cells 1021 or batteries or other primary energy sources 1022 or secondary energy sources (a photovoltaic cell, e.g.); wireless communication linkages 1094 (operably coupled with one or more controllers 1095 in network 1090 and remote from device 1010, e.g.); a global positioning system (GPS) 1063; timers 1064; or local controllers 1085 operable for controlling one, two, or several props 1071, 1072, 1073 or wheels 683 (via one or more motors 1081, 1082, 1083, e.g.).

In light of teachings herein, numerous existing techniques may be applied for configuring special-purpose circuitry or other structures effective for remotely, autonomously, or otherwise controlling one or more devices in flight without undue experimentation or for configuring other decisions and devices as described herein. See, e.g., U.S. Pat. No. 8,090,525 ("Device and method for providing automatic assistance to air traffic controllers"); U.S. Pat. No. 8,078,395 ("Control system for automatic circle flight"); U.S. Pat. No. 7,890,221 ("Method and device for consolidation by software synchronisation in flight control computers"); U.S. Pat. No. 6,926,233 ("Automatic formation flight control system (AFFCS)—a system for automatic formation flight control of vehicles not limited to aircraft, helicopters, or space platforms"); U.S. Pat. No. 6,847,865 ("Miniature, unmanned aircraft with onboard stabilization and automated ground control of flight path"); U.S. Pat. No. 6,604,044 ("Method for generating conflict resolutions for air traffic control of free flight operations"); U.S. Pat. No. 6,552,669 ("Automated air-traffic advisory system and method"); U.S. Pat. No. 6,538,581 ("Apparatus for indicating air traffic and terrain collision threat to an aircraft"); U.S. Pat. No. 6,526,377 ("Virtual presence"); U.S. Pat. No. 6,133,867 ("Integrated air traffic management and collision avoidance system").

Figure 11:
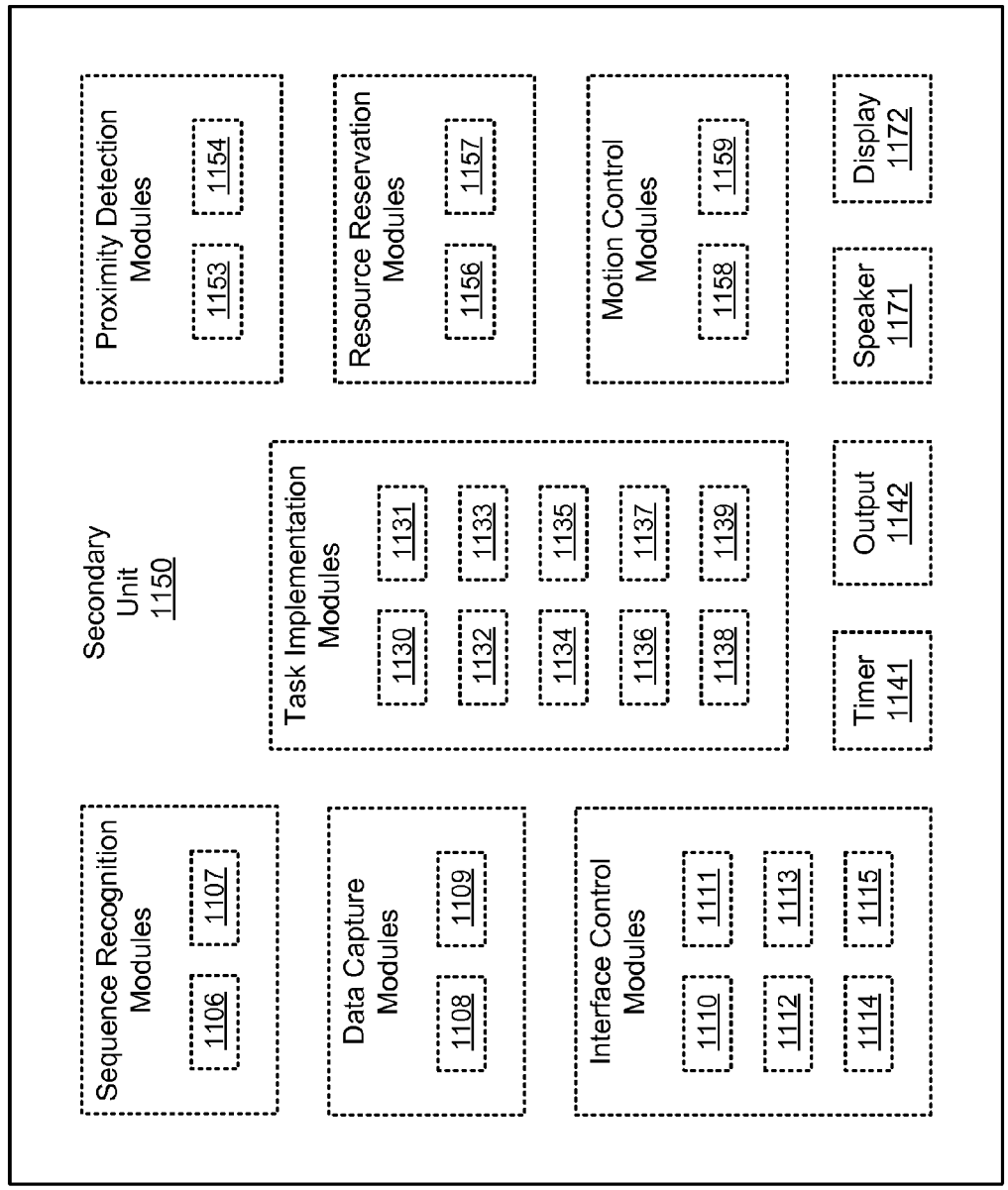
FIG. 11 depicts an exemplary environment featuring a secondary unit.

Another system in which one or more technologies may be implemented is shown in FIG. 11. Secondary unit 1150 comprises one or more instances of sequence recognition modules 1106, 1107; data capture modules 1108, 1109; interface control modules 1110, 1111, 1112, 1113, 1114, 1115; task implementation modules 1130, 1131, 1132, 1133, 1134, 1135, 1136, 1137, 1138, 1139; timers 1141 or other delay elements; outputs 1142 (speakers 1171 or displays 1172 configured to present data to device user 226, e.g.); proximity detection modules 1153, 1154; resource reservation modules 1156, 1157; or motion control modules 1158, 1159. In some variants, one or more instances of secondary unit 1150 may be operably coupled with event/condition detection unit or may reside in one or more networks 190, 990, 1090 described above.

Figure 12:
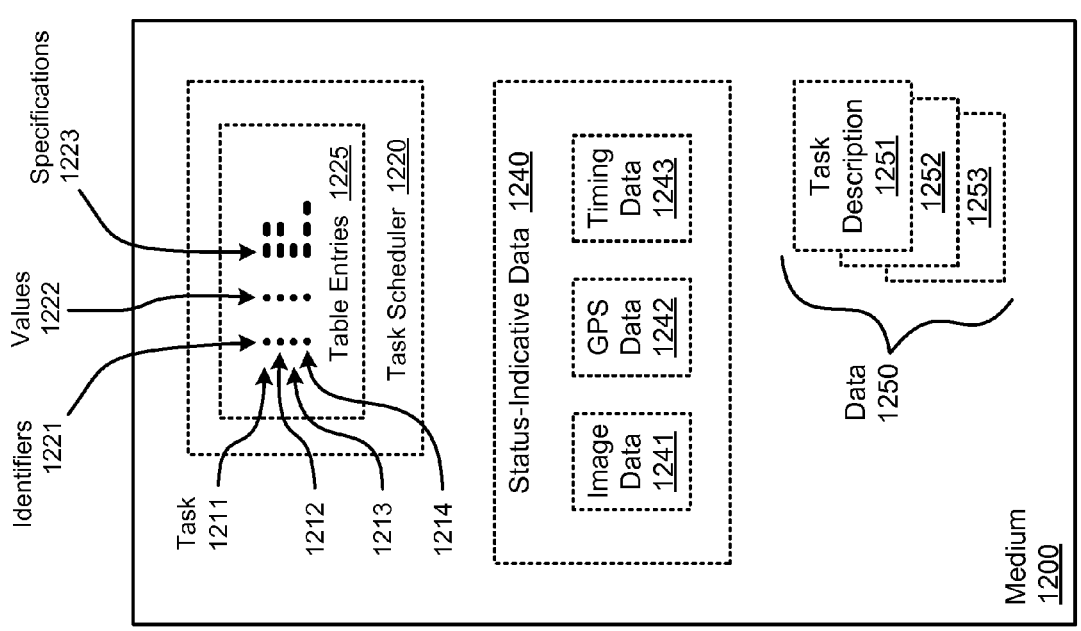
FIG. 12 depicts a physical medium residing in one or more of the above-described environments.

Another system in which one or more technologies may be implemented is shown in FIG. 12. A medium 1200 (of storage or transmission or display, e.g.) may include one or more instances of task scheduler 1220 containing or otherwise able to access table entries 1225 comprising one or more digitally represented tasks 1211, 1212, 1213, 1214 (each shown as a row, e.g.), each of which may include one or more instances of task identifiers 1221, values 1222, or specifications 1223. Medium 1200 may also include status-indicative data 1240 (comprising one or more of image data 1241, GPS data 1242, or timing data 1243, e.g.); task descriptions 1251, 1252, 1253; or other task-related data 1250 as described herein.

Figure 13:
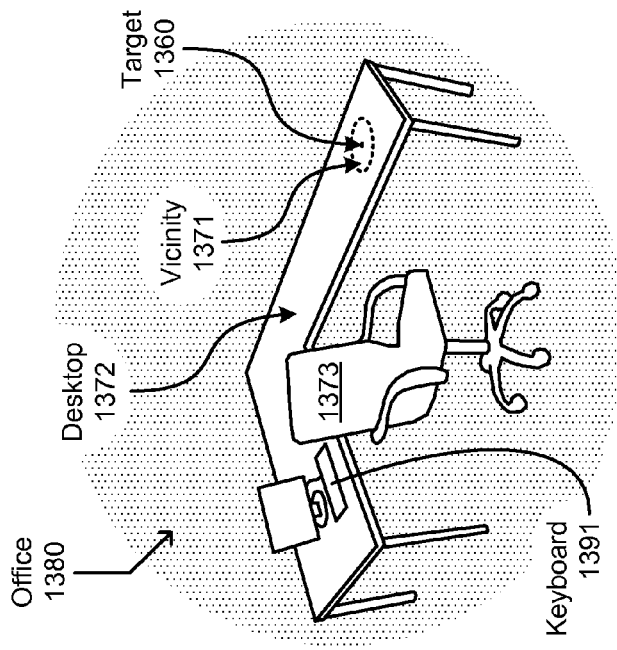
FIG. 13 depicts a chair, keyboard, and desktop in an office into which a UAD may enter.

Another context in which one or more technologies may be implemented is shown in FIG. 13, depicting a stationary computer (implementing interface device 310, e.g.) having a keyboard 1391 (implementing input 391, e.g.) and a user's chair 1373 in an office 1380. Office 1380 further comprises a desktop 1372 that supports or comprises a target 1360 (an ASIC 409, surface pattern, or other feature detectable by UAD 1005, e.g.) within a vicinity 1371 of which a delivery or landing (by or of UAD 1005, e.g.) may occur as described below.

Figure 14:
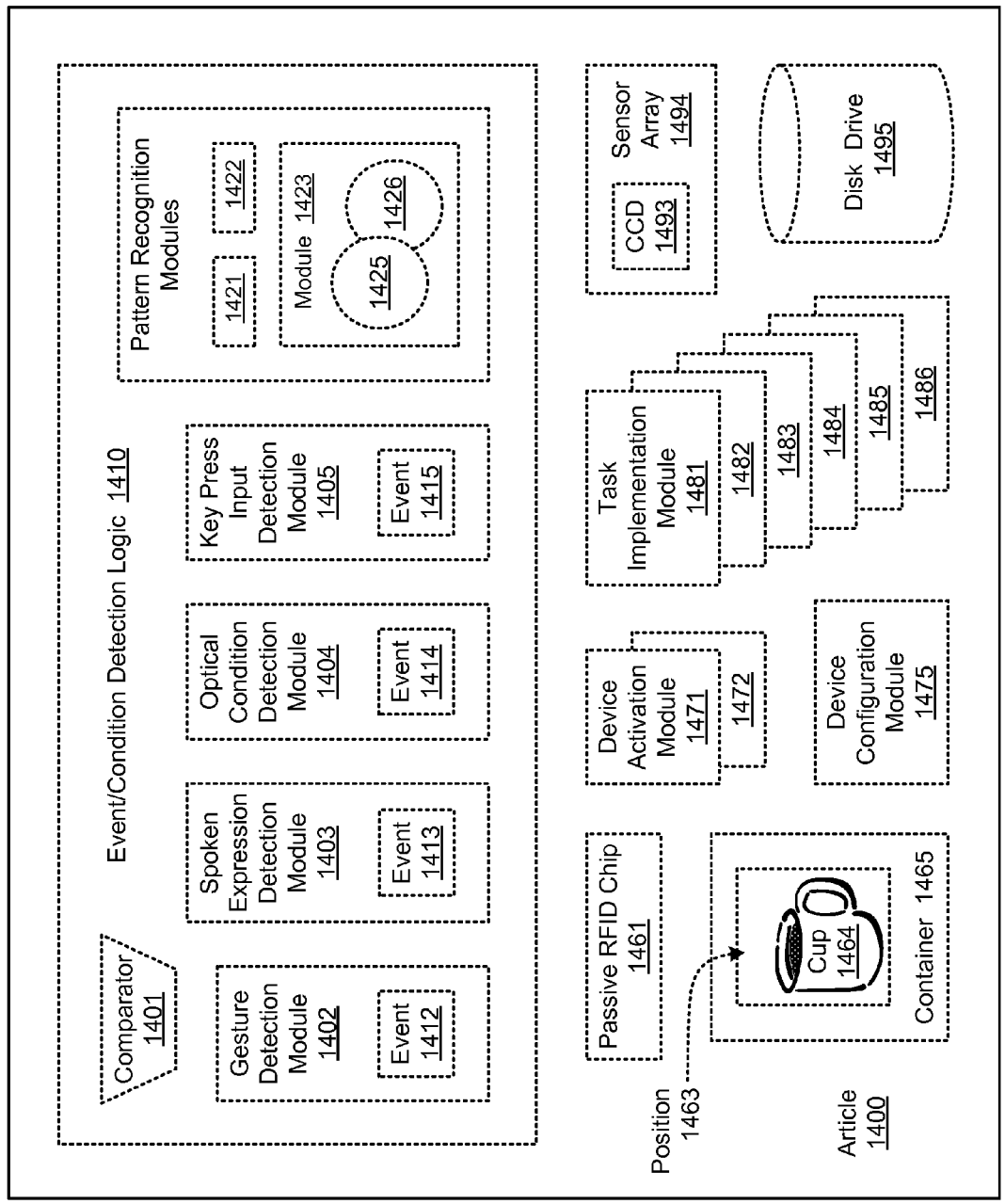
FIG. 14 depicts an exemplary environment featuring an article of manufacture.

Another context in which one or more technologies may be implemented is shown in FIG. 14, depicting one or more instances of articles 1400 each comprising a comparator 1401 or other event/condition logic 1410 that may (optionally) implement target 1360 as well. Alternatively or additionally, article 1400 may comprise one or more instances of passive radio frequency identification (RFID) chips 1461; a cup 1464 or other container 1465 above which is a position 1463 to which UAD 1005 may fly; device activations modules 1471, 1472; device configuration modules 1475; task implementation modules 1481, 1482, 1483, 1484, 1485, 1486; device configuration modules 1475; task implementation modules 1481, 1482, 1483, 1484, 1485, 1486; charge-coupled devices (CCD's) 1493 or other sensor arrays 1494; or disk drives 1495. In some contexts, as variously described herein, article 1400 (implementing UAD 1005, e.g.) may include a sensor array 1494 (camera, e.g.) configured to depict (some or all of) a vicinity (chair 1373, e.g.) of an object (target 1360, e.g.) or a person 727 or of itself.

Figure 20:
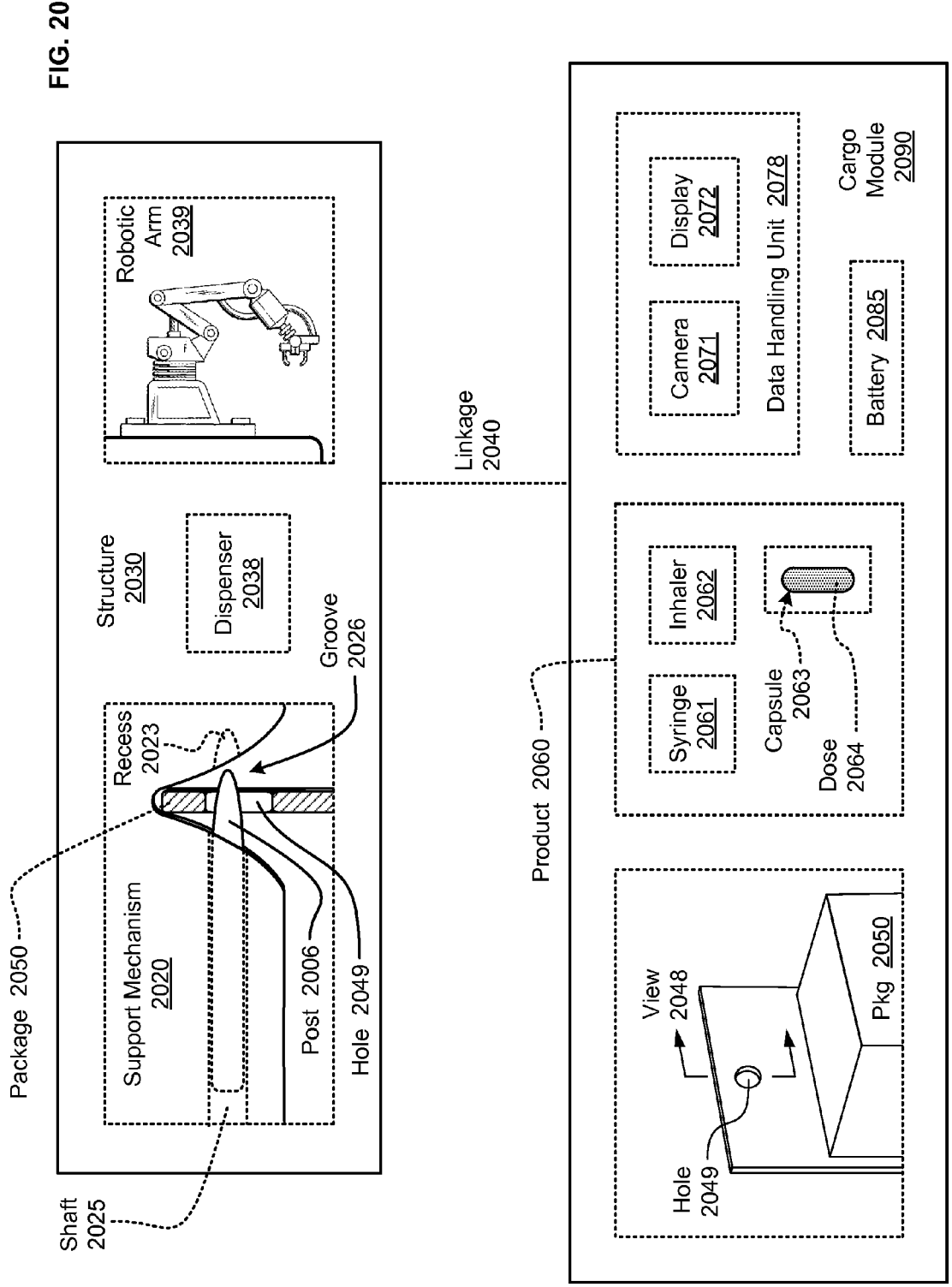
FIG. 20 depicts an exemplary environment featuring a structural component of a UAD having at least a releasable mechanical linkage to a package or other cargo module.

Another context in which one or more technologies may be implemented is shown in FIG. 20, depicting various structures forming a part of UAD 1005 (on a bottom or side thereof, e.g.) having one or more mechanical linkages 2040 (adhesives or tethers or clamps or other such releasable support mechanisms 2020, e.g.) that can physically engage or disengage one or more cargo modules 2090. As shown, each such cargo module 2090 may include one or more instances of packages 2050 (having a hole 2049 therethrough, e.g.); syringes 2061, inhalers 2062, capsules 2063 (containing a dose 2064 of therapeutic material, e.g.), or other such products 2060 (in a dispenser 2038, e.g.); data handling units 2078 (comprising a camera 2071, display 2072, or other device having a primary function of handling data, e.g.); or releasable UAD energy sources (battery 2085, e.g.). In a variant of structure 2030 configured to engage package 2050, for example, a cross-sectional view 2048 across hole 2049 is shown in a context in which package 2050 protrudes into a groove 2026 of UAD 1005. Post 2006 may be moved (e.g. magnetically by a solenoid or mechanically by a spring, not shown) toward recess 2023 (to the right, as shown) to engage package 2050 or away from recess 2023 (to the left, as shown) to disengage package 2050, as described below. Alternatively or additionally, UAD 1005 may include a robotic arm 2039 or similar structure 2030 for engaging or disengaging cargo module 2090 (pursuant to an engagement trigger or disengagement trigger from of one or more task implementation modules 1130-1139, 1481-1486, e.g.).

In some embodiments, a material is "therapeutic" if it includes a pharmaceutical (e.g. an antibiotic, pain reliever, or stimulant), a nutraceutical (e.g. a dietary supplement or other therapeutic food ingredient), a topically applied material (e.g. a liniment or lotion prescribed or used in a medical or other health-related practice), or other product or components (e.g. propellants, inhalants, inoculants, or resorbable binders or coatings) intended primarily to maintain or improve a subject's health or performance. Some embodiments relate to a delivery of a "single dose" (±50%, e.g.) generally signifying a prescribed or recommended amount of a material ("two aspirin," e.g.) to be administered into or onto a subject's body either (1) periodically or (2) at one time.

In light of teachings herein, numerous existing techniques may be applied for configuring special-purpose circuitry or other structures effective for configuring devices to engage or disengage data handling units, medical products, energy sources, or other such modular cargo without undue experimentation or for configuring other decisions and devices as described herein. See, e.g., U.S. Pat. No. 8,192,698 ("Sampling probe, gripper and interface for laboratory sample management systems"); U.S. Pat. No. 8,179,496 ("Display casing capable of accommodating LCD panel modules of different sizes"); U.S. Pat. No. 8,167,236 ("Hybrid lift air vehicle"); U.S. Pat. No. 8,164,302 ("System for replenishing energy sources onboard different types of automatic vehicles"); U.S. Pat. No. 8,141,814 ("Lighter-than-air vertical load lifting system"); U.S. Pat. No. 8,128,026 ("Removable cargo pod with lifting mechanism and open top"); U.S. Pat. No. 8,122,982 ("Mobile robot systems and methods"); U.S. Pat. No. 8,101,434 ("Method for LED-module assembly"); U.S. Pat. No. 8,091,463 ("Machine gun ammunition holder incorporating center of gravity downward ejection-deflector"); U.S. Pat. No. 8,066,460 ("Apparatus and method for cargo loading system"); U.S. Pat. No. 8,037,839 ("Device for handling a load hoisted between two locations offset both vertically and horizontally"); U.S. Pat. No. 8,029,228 ("Cable hoisting apparatus"); U.S. Pat. No. 7,919,060 ("Dispenser for flattened articles"); U.S. Pat. No. 7,913,370 ("Method and apparatus for assembling exterior automotive vehicle body components onto an automotive vehicle body"); U.S. Pat. No. 7,750,778 ("System and method for attachment of objects"); U.S. Pat. No. 7,717,255 ("End of arm tool, apparatus, and method of engaging an article"); U.S. Pat. No. 7,648,513 ("Surgical manipulator for a telerobotic system"); U.S. Pat. No. 7,641,461 ("Robotic systems for automated construction"); U.S. Pat. No. 7,549,204 ("Methods for picking and placing workpieces into small form factor hard disk drives"); U.S. Pat. No. 7,474,212 ("Object tagged with RFID tag and device and method for processing it"); and U.S. Pat. No. 7,252,453 ("Robot arm coupling apparatus").

Figure 21:
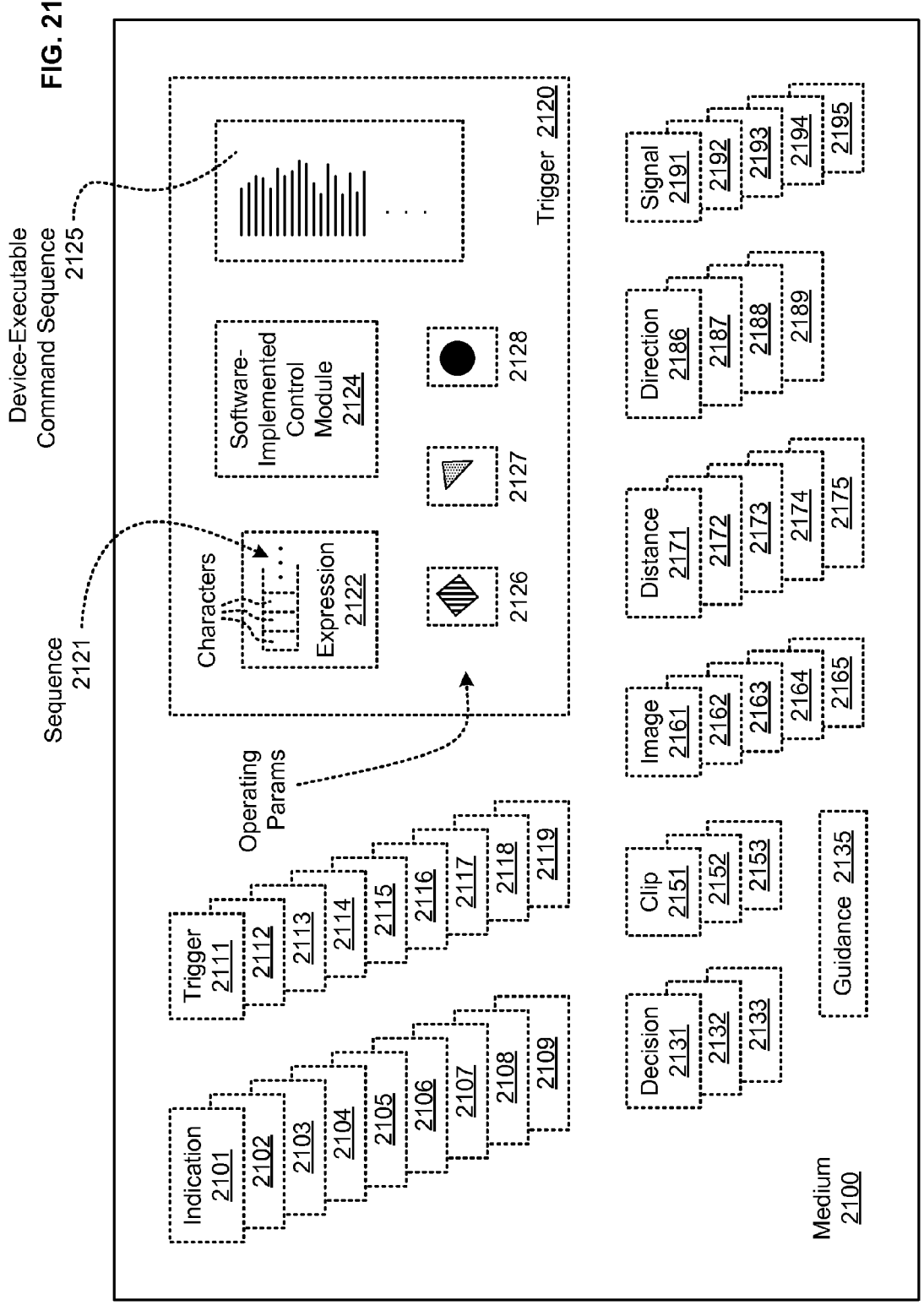
FIGS. 21-24 each depicts physical media residing in one or more of the above-described environments.

Another context in which one or more technologies may be implemented is shown in FIG. 21. A medium 2100 (configured to implement storage or transmission or display, e.g.) may bear one or more instances of indications 2101, 2102, 2103, 2104, 2105, 2106, 2107, 2108, 2109; triggers 2111, 2112, 2113, 2114, 2115, 2116, 2117, 2118, 2119, 2120; guidance 2130; decisions 2131, 2132, 2133; clips 2151, 2152, 2153; images 2161, 2162, 2163, 2164, 2165; distances 2171, 2172, 2173, 2174, 2175; directions 2186, 2187, 2188, 2189; or signals 2191, 2192, 2193, 2194, 2195. Each of these items may (optionally) include two or more components. In various embodiments, for example, one or more of triggers 2111-2120 may comprise one or more instances of a character sequence 2121 or similar digital expression 2122 (expressing a scalar operating parameter 2127, an alphanumeric identifier, or other such operating parameter 2128, e.g.) to which a trigger recipient (an instance of task implementation module 1130 residing in UAD 1005 or another module depicted in FIGS. 1-20, e.g.) is configured to respond. Each such trigger may likewise comprise one or more software-implemented control modules 2124 (comprising a command sequence 2125 executable by processor 365, e.g.) or operating parameters 2126, 2127, 2128.

Several variants described herein refer to software or other device-detectable "implementations" such as one or more instances of computer-readable code, transistor or latch connectivity layouts or other geometric expressions of logical elements, firmware or software expressions of transfer functions implementing computational specifications, digital expressions of truth tables, or the like. Such instances can, in some implementations, include source code or other human-readable portions. Alternatively or additionally, functions of implementations described herein may constitute one or more device-detectable outputs such as decisions, manifestations, side effects, results, coding or other expressions, displayable images, data files, data associations, statistical correlations, streaming signals, intensity levels, frequencies or other measurable attributes, packets or other encoded expressions, or the like from invoking or monitoring the implementation as described herein.

In some embodiments, a "state" of a component may comprise "available" or some other such state-descriptive labels, an event count or other such memory values, a partial depletion or other such physical property of a supply device, a voltage, or any other such conditions or attributes that may change between two or more possible values irrespective of device location. Such states may be received directly as a measurement or other detection, in some variants, and/or may be inferred from a component's behavior over time. A distributed or other composite system may comprise vector-valued device states, moreover, which may affect dispensations or departures in various ways as exemplified herein.

Figure 22:
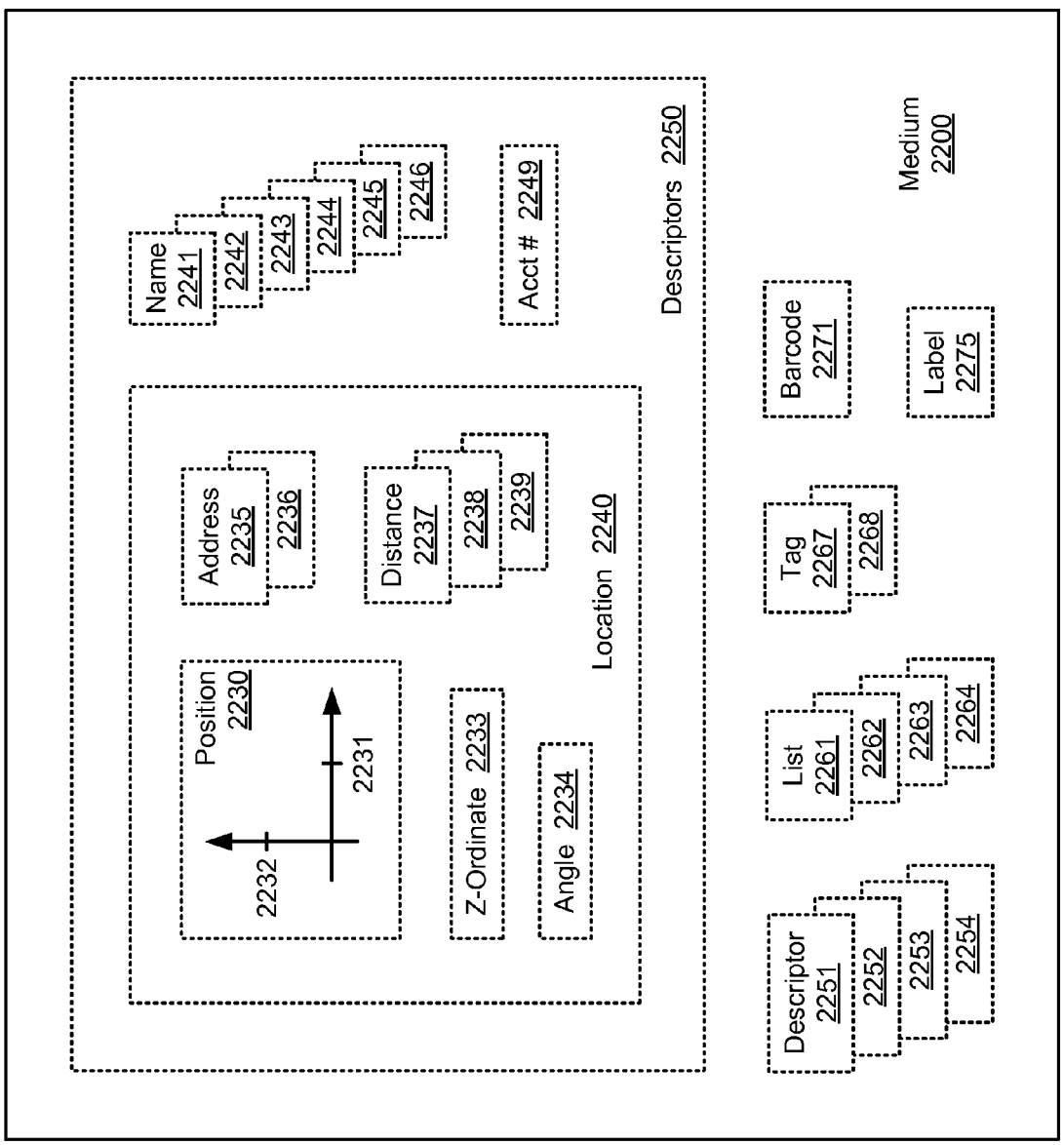

Another system in which one or more technologies may be implemented is shown in FIG. 22. A medium 2200 (of storage or transmission or display, e.g.) may include one or more instances of positions 2230 (described by a respective X-ordinate 2231 and Y-ordinate 2232, e.g.). In some contexts, such positions can each be described by other coordinates as well: a Z-ordinate 2233 (altitude, e.g.) or an angle 2234 (in a polar coordinate system, e.g.). In some contexts, locations 2240 described herein may likewise be expressed in words or numbers, such as one or more addresses 2235, 2236 or distances 2237, 2238, 2239. In various contexts, an entity herein may likewise be described by one or more names 2241, 2242, 2243, 2244, 2245, 2246; account numbers 2249; or other such descriptors 2250, 2251, 2252, 2253, 2254. Sets of entities may be identified by one or more lists 2261, 2262, 2263, 2264 on medium 2200. In some contexts, for example, such media 2200 may comprise one or more tags 2267, 2268; barcodes 2271; or other labels 2275 as further described below.

Figure 23:
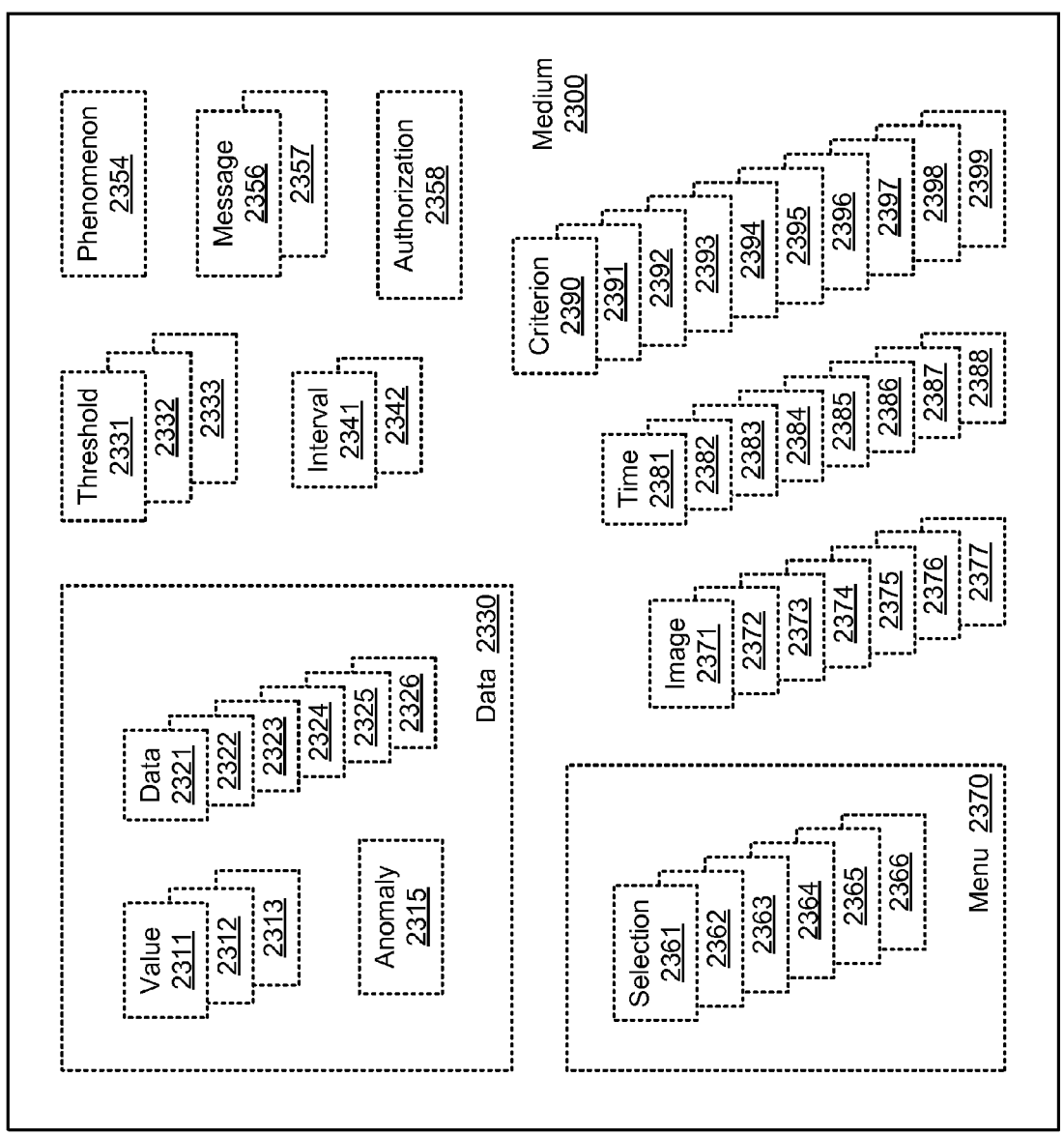

Another system in which one or more technologies may be implemented is shown in FIG. 23. A medium 2300 (of storage or transmission or display, e.g.) may include one or more instances of values 2311, 2312, 2313; data anomalies 2315; or other data 2321, 2322, 2323, 2324, 2325, 2326, 2330 as described below. In some contexts, medium 2300 may likewise contain one or more instances of thresholds 2331, 2332, 2333; intervals 2341, 2342; device-detectable phenomena 2354; messages 2356, 2357; authorizations 2358; images 2371, 2372, 2373, 2374, 2375, 2376, 2377;

times 2381, 2382, 2383, 2384, 2385, 2386, 2387, 2388; or criteria 2390, 2391, 2392, 2393, 2394, 2395, 2396, 2397, 2398, 2399. Some or all of these may be expressed digitally. In some contexts, moreover, a medium 2300 (of display, e.g.) may present one or more menus 2370 comprising one or more default selections 2361 or other selections 2362, 2363, 2364, 2365, 2366 (for a UAD operator 729 to choose among, e.g.).

Figure 24:
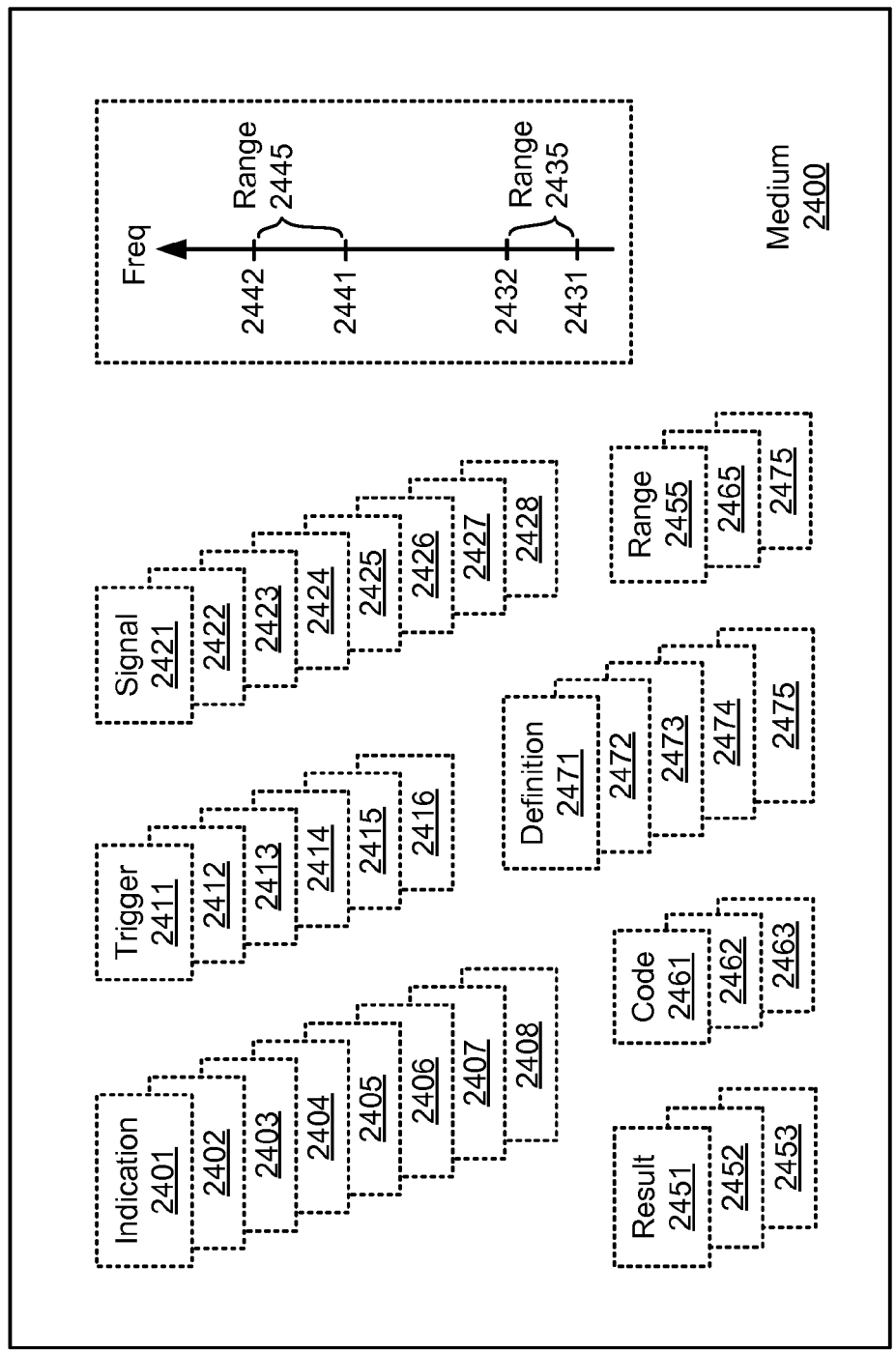

Another system in which one or more technologies may be implemented is shown in FIG. 24. A medium 2400 (of storage or transmission or display, e.g.) may include one or more instances of indications 2401, 2402, 2403, 2404, 2405, 2406, 2407, 2408; triggers 2411, 2412, 2413, 2414, 2415, 2416; or other signals 2421, 2422, 2423, 2424, 2425, 2426, 2427, 2428. In some contexts, medium 2400 may likewise contain one or more frequencies 2431, 2432, 2441, 2442 or ranges 2435, 2445 thereof; results 2451, 2452, 2453 of actions; instances of code 2461, 2462, 2463 (executable by processor 365, e.g.); definitions 2471, 2472, 2473, 2474, 2475; ranges 2455, 2465, 2475; or other thresholds. Some or all of these may be expressed digitally.

Figure 25:
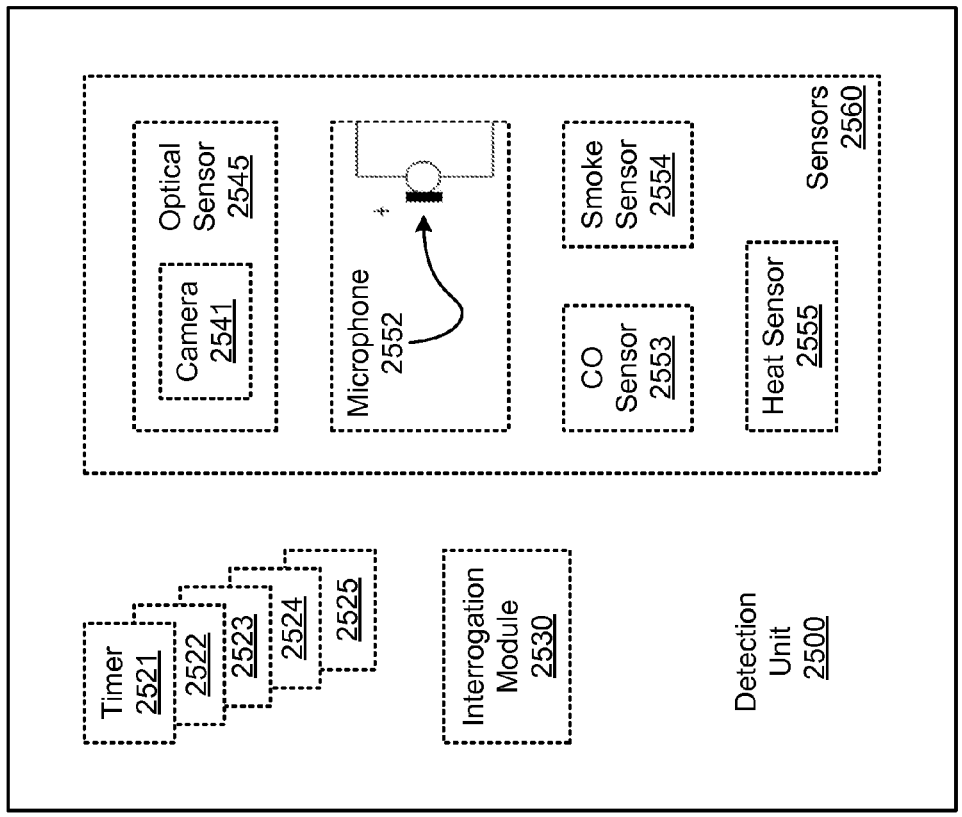
FIG. 25 depicts a detection unit usable in one or more of the above-described environments to detect time intervals or other physical phenomena.

Another system in which one or more technologies may be implemented is shown in FIG. 25. A detection unit 2500 may include one or more instances of timers 2521, 2522, 2523, 2524, 2525; interrogation modules 2530; cameras 2541 or other optical sensors 2545; microphones 2552; carbon monoxide sensors 2553, smoke sensors 2554, or other concentration sensors; or heat sensors 2555 or other such sensors 2560 (for detecting intrinsic properties of matter, e.g.).

Figure 26:
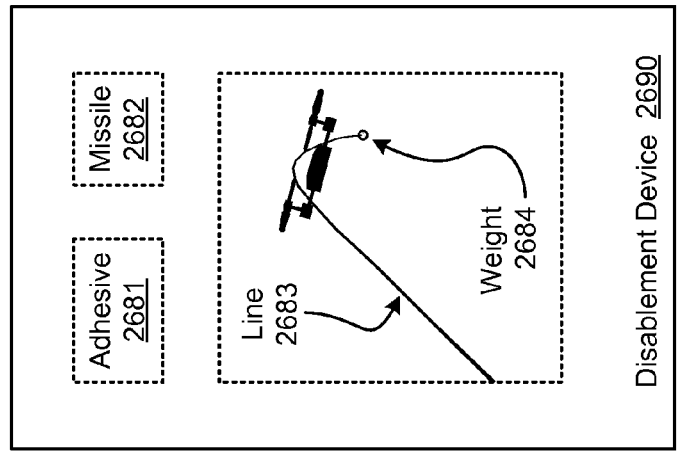
FIG. 26 depicts a disablement device usable in one or more of the above-described environments to disable a UAD.

Another system in which one or more technologies may be implemented is shown in FIG. 26. A disablement device 2690 (of a component of a UAD or other device described herein, e.g.) may include one or more instances of releasable adhesives 2681 or flammable compounds; bullets or other missiles 2682; throwable nets or lines 2683 (incorporating weights 2684, e.g.); electromagnetic pulse generators; or other such components configured to disable a UAD or other entity as described herein. In some contexts, for example, a stationary or other device (UAD, e.g.) may be configured to incorporate one or more such disablement devices 2690 (as a cargo module 2085 or other component, e.g.) to impede access into a region (room or proximity or other zone, e.g.) by at least partly disabling another entity in response to one or more triggers 2414 described herein.

Figure 27:
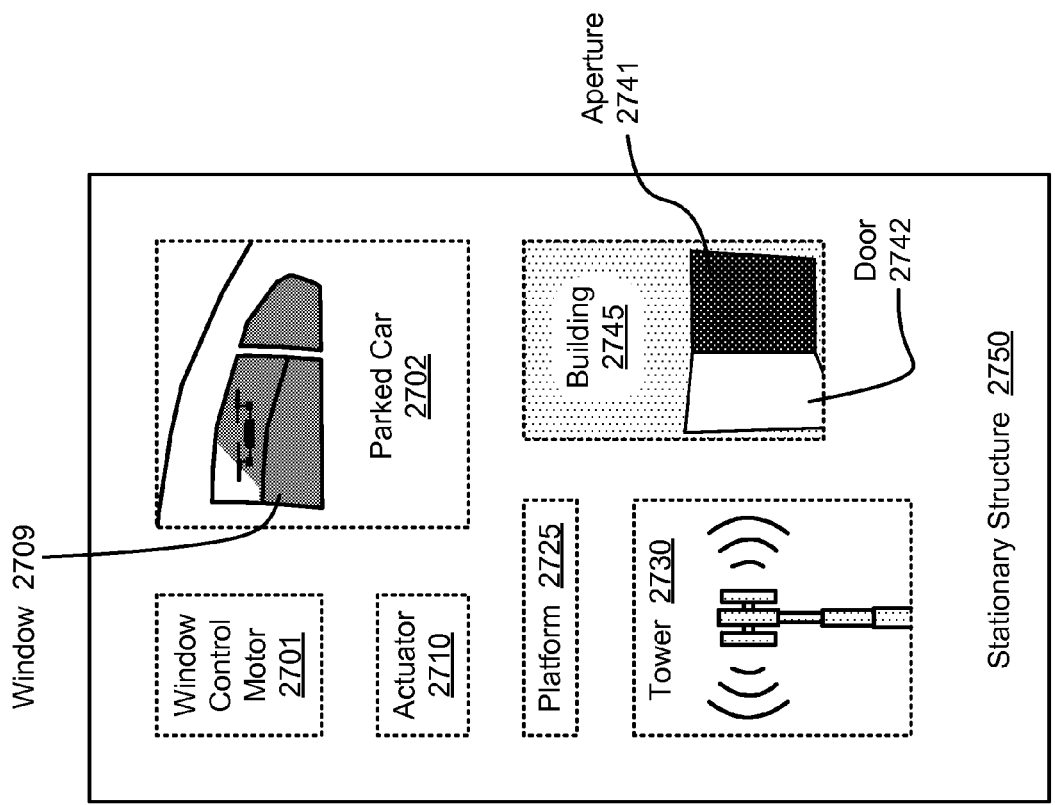
FIG. 27 depicts a stationary structure configured to support or otherwise interact with a UAD.

Another system in which one or more technologies may be implemented is shown in FIG. 27. A stationary structure 2750 may include one or more instances of windows 2709, doors 2742, or other movable actuators 2710. In a context in which stationary structure 2750 comprises a parked car 2702, for example, one or more windows 2709 may be opened by window control motor 2701. Alternatively or additionally, in some contexts, stationary structure may comprise one or more platforms 2725, towers 2730, or buildings 2745 (sometimes having one or more apertures 2741, e.g.) as described below.

Figure 35:
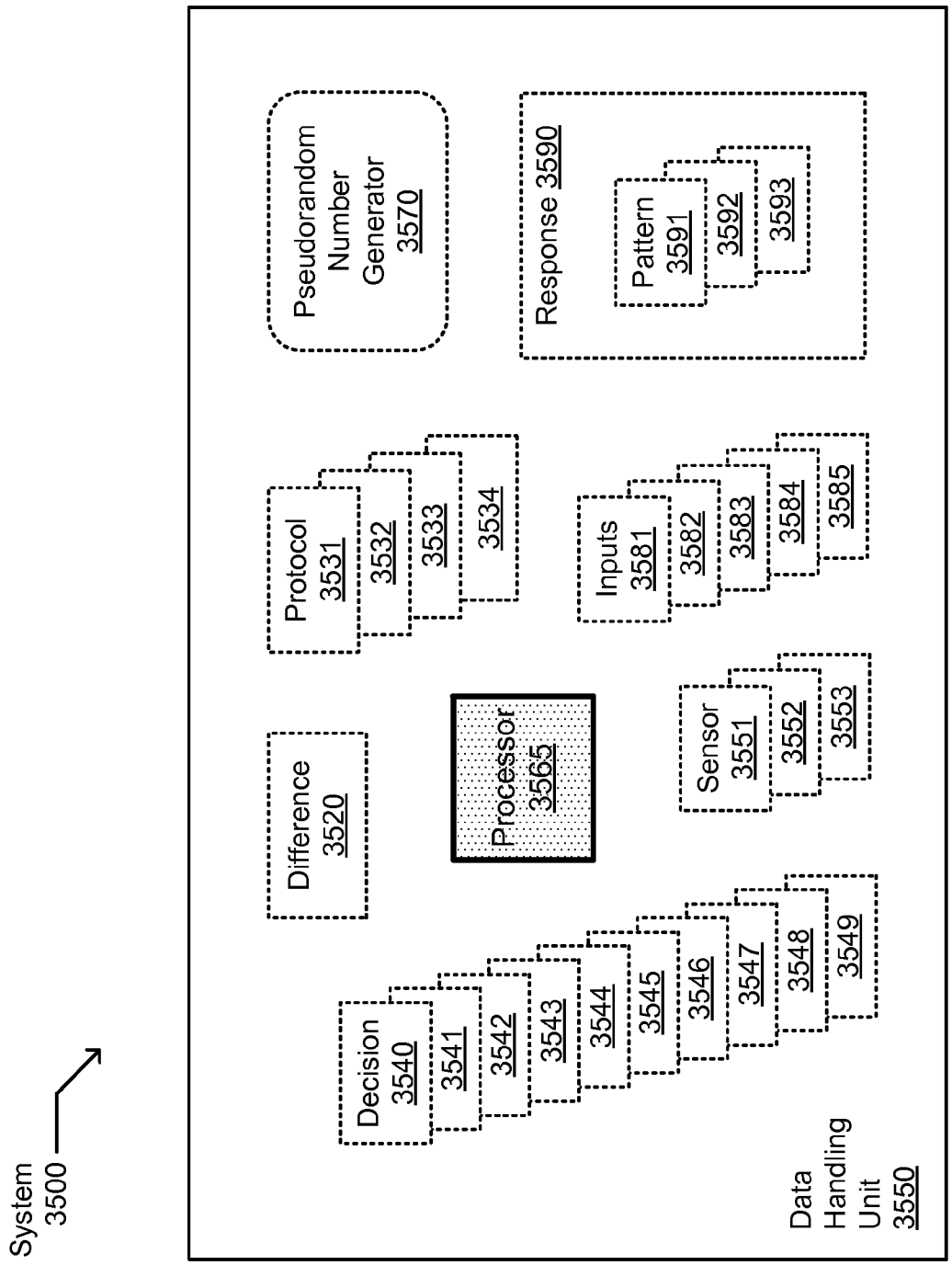
FIG. 35 depicts an exemplary environment featuring a data handling unit.

Another context in which one or more technologies may be implemented is shown in FIG. 35. System 3500 includes data handling unit 3550, one or more of which may (optionally) comprise primary unit 110, event/condition detection unit 400, or secondary unit 1150. Each data handling unit 3550 may comprise one or more differences 3520; protocols 3531, 3532, 3533, 3534; decisions 3540, 3541, 3542, 3543, 3544, 3545, 3546, 3547, 3548, 3549; sensors 3551, 3552, 3553; or pseudorandom number generators 3570 or other inputs 3581, 3582, 3583, 3584, 3585. Data handling unit 3550 may likewise comprise one or more processors 3565 configured to perform various software-implemented tasks, in some contexts, such as identifying one or more patterns 3591, 3592, 3593 that may be present in responses 3590 as described below.

Figure 36:
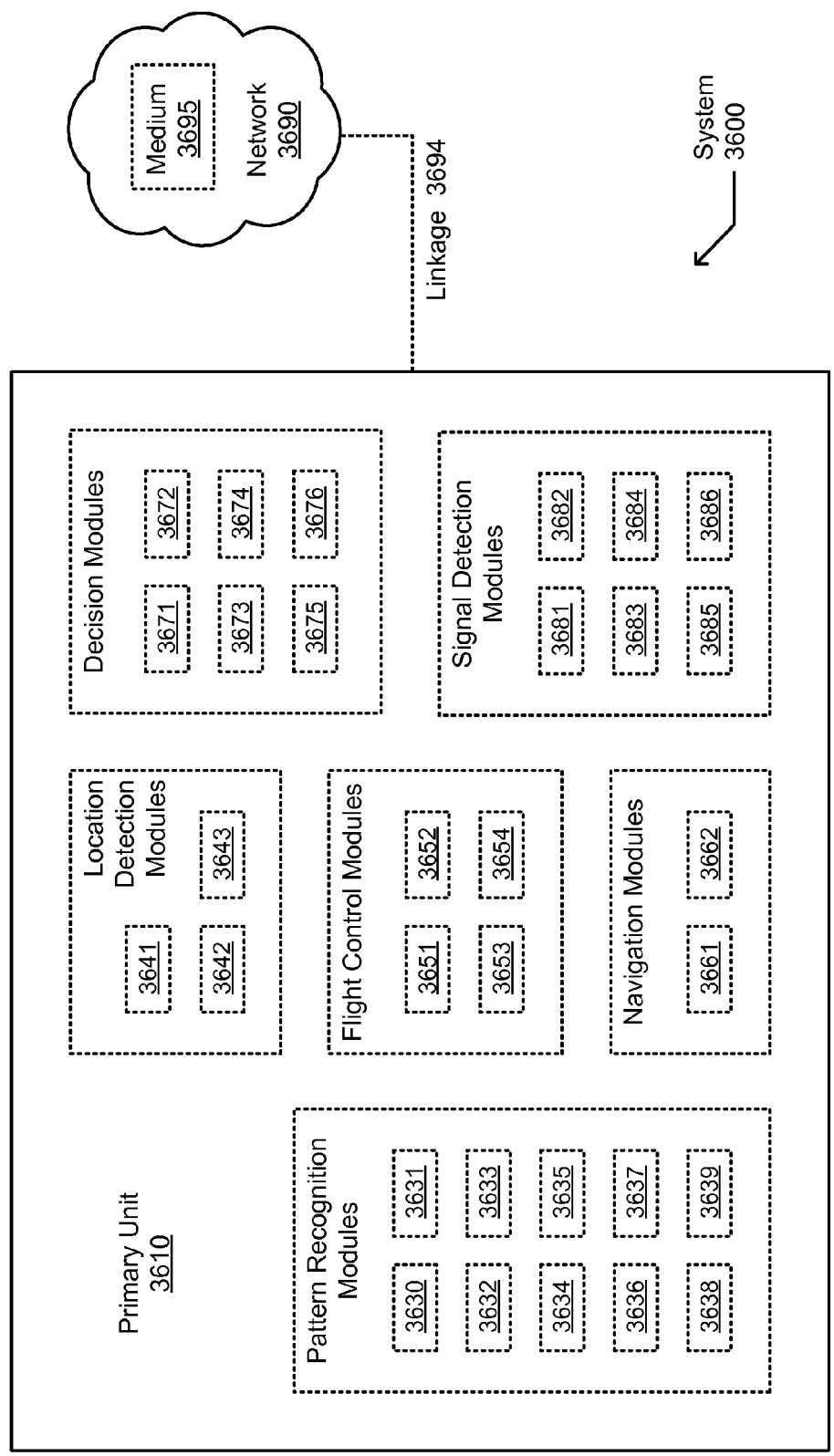
FIG. 36 depicts an exemplary environment like that of FIG. 1, featuring a primary unit operably linked to a network.

FIG. 36 depicts another context in which one or more technologies may be implemented. System 3600 comprises a primary unit 3610 that may include one or more instances of pattern recognition modules 3630, 3631, 3632, 3633, 3634, 3635, 3636, 3637, 3638, 3639; location detection modules 3641, 3642, 3643; flight control modules 3651, 3652, 3653, 3654; navigation modules 3661, 3662; decision modules 3671, 3672, 3673, 3674, 3675, 3676; or signal detection modules 3681, 3682, 3683, 3684, 3685, 3686 as described in further detail below. In some contexts, primary unit 3610 may be operably coupled to one or more networks 190, 3690 via one or more communication linkages 3694. Instances of storage or other data-handling media 3695 operably coupled to one or more such modules may, moreover, reside in primary unit 3610 or network 3690, as described below. In some contexts, moreover, primary unit 3610 may implement (an instance of) primary unit 110.

Figure 37:
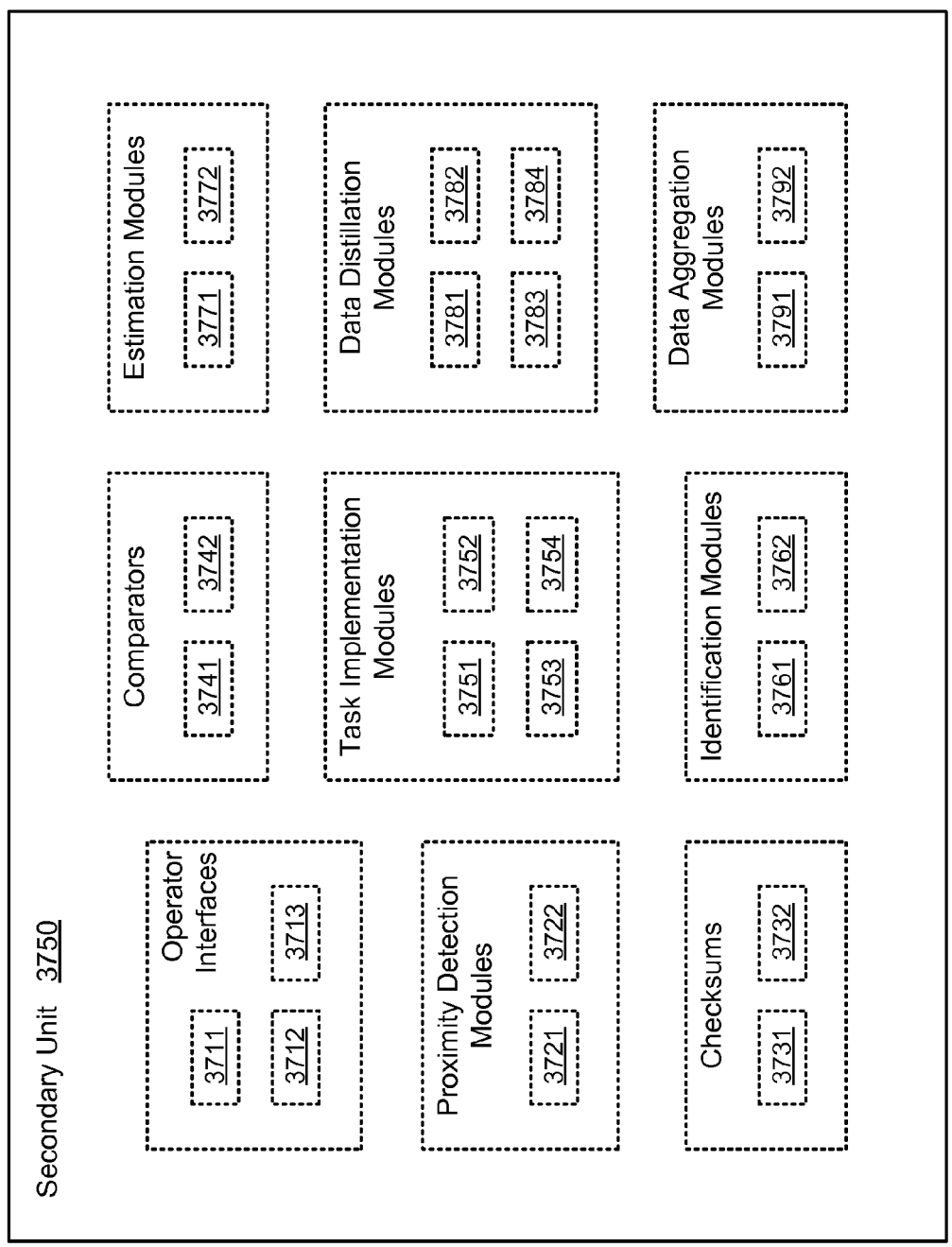
FIG. 37 depicts an exemplary environment like that of FIG. 11, featuring a secondary unit.

FIG. 37 depicts another context in which one or more technologies may be implemented. System 3700 comprises a secondary unit 3750 that may include one or more instances of operator interfaces 3711, 3712, 3713; proximity detection modules 3721, 3722; checksums 3731, 3732; comparators 3741, 3742; task implementation modules 3751, 3752, 3753, 3754; identification modules 3761, 3762; estimation modules 3771, 3772; data distillation modules 3781, 3782, 3783, 3784; or data aggregation modules 3791, 3792 as further described below. In some contexts, moreover, secondary unit 3750 may implement secondary unit 1150.

Figure 28:
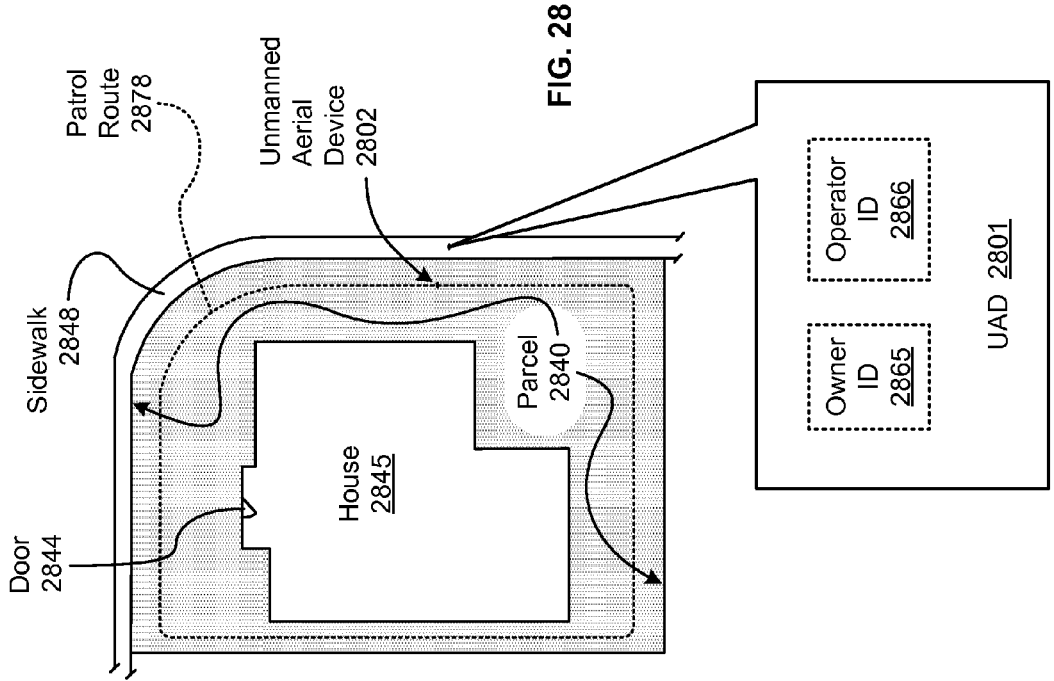
FIG. 28 depicts an exemplary environment featuring two UAD's in a vicinity of a house.

Another system in which one or more technologies may be implemented is shown in FIG. 28. A house 2845 sits upon a parcel 2840 of land adjacent a sidewalk 2848. In some contexts an unmanned aerial device 2801 (comprising one or more owner identifiers 2865 or operator identifiers 2866, e.g.) approaches the house 2845 (pursuant to one or more tasks described herein, e.g.) and encounters another UAD 2802 (following a patrol route 2878 or other path, e.g.).

Figure 38:
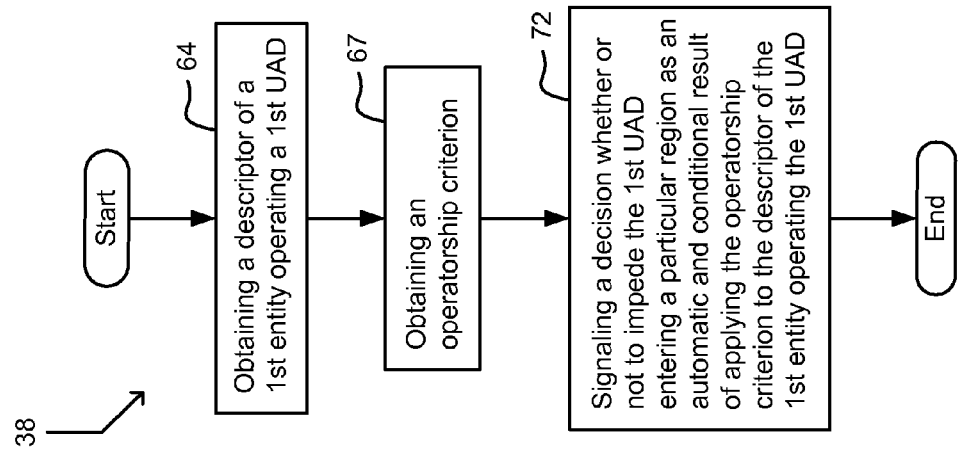
FIG. 38 depicts a high-level logic flow of an operational process described with reference to FIG. 28.

With reference now to FIG. 38, shown is a high-level logic flow 38 of an operational process. Intensive operation 64 describes obtaining a descriptor of a first entity operating a first unmanned aerial device (e.g. operator interface 3711 receiving an owner identifier 2865 or operator identifier 2866 indicating who is operating or managing the operation of UAD 2801). This can occur, for example, in a context in which operator identifier 2866 comprises a user name 2243, facility name 2244, corporate entity name 2245, or account number 2249 used for such description and in which UAD 2801 implements UAD 1005. In some contexts, for example, corporation or other entity operating UAD 2801 may choose to identify itself by one or more hardware or software identifiers (a controller name 2246, e.g.) or by one or more locations 2240 (of a house 2845 or parcel 2840 of land, e.g.). In some variants such locations 2240 may comprise a street address 2236 other expressions of distances 2238 from a reference position (mile markers, e.g.). Alternatively or additionally, operation 64 may be performed by an identification module 3761 configured to assign a default descriptor 2253 to UAD 2801 until and unless identification module 3762 receives a wireless signal 2425 containing an operator identifier 2866.

Intensive operation 67 describes obtaining an operatorship criterion (e.g. pattern recognition module 3631 implementing one or more criteria 2392-2396 applicable to one or more corresponding descriptors 2250-2254). This can occur, for example, in a context in which criterion 2396 is satisfied for any descriptor that is present in a first list 2261; in which criterion 2392 is satisfied for any descriptor that is present in a second list 2262; in which criterion 2393 is satisfied for any descriptor (expressed as a sequence 2121 of characters, e.g.) satisfying a checksum 3731 or cyclical redundancy check (of digital values each corresponding to each character, e.g.) or similar mathematically expressed requirement; in which each such criterion will otherwise not be satisfied; and in which pattern recognition module 3631 can invoke any such criteria selectively. In some variants, for example, such criteria are each implemented in an instance of code 2462 executable by processor 365 or other structure operably accessible to primary unit 3610.

Extensive operation 72 describes signaling a decision whether or not to impede the first unmanned aerial device entering a particular region as an automatic and conditional result of applying the operatorship criterion to the descriptor of the first entity operating the first unmanned aerial device (e.g. task implementation module 3754 implementing a decision 3545 to prevent UAD 2801 from entering house 2844 partly based on location detection module 3642 determining that UAD 2801 is flying over parcel 2840 and partly based on pattern recognition module 3631 failing to recognize an operator identifier 2866 received from UAD 2801). This can occur, for example, in a context in which such a decision 3545 is implemented by invoking a flight control module 3654 configured to cause UAD 2802 to block UAD 2801 from moving closer to house 2844; in which task implementation module 3754 would not otherwise implement such a decision 3545; and in which one or more such criteria 2392-2396 have previously been selected (as a corresponding selection 2362-2366 on menu 2370, e.g.) by an occupant or administrator of the particular region (a building 935 or office 1380 or parcel 2840 of land, e.g.). In some contexts, moreover, task implementation module 3754 may be configured to respond to such circumstances by implementing a decision 3546 to cause UAD 2802 to collide with or otherwise intercept or disable UAD 2801.

Figure 29:
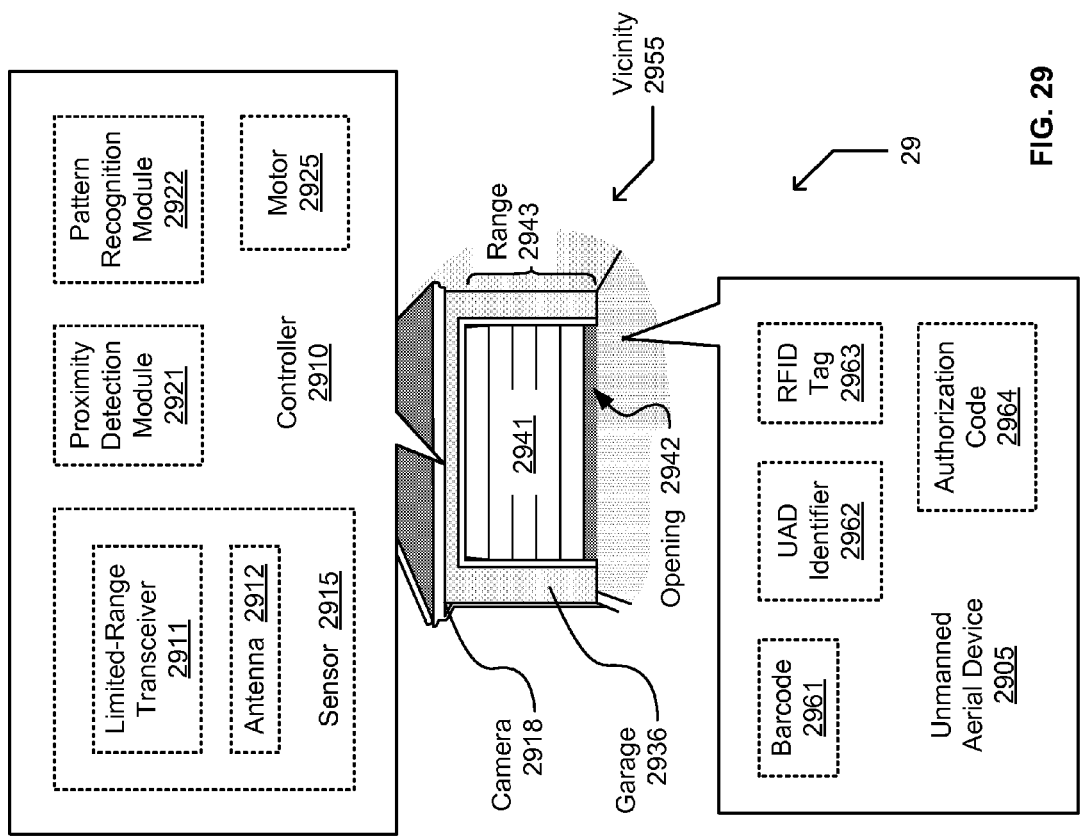
FIG. 29 depicts an exemplary environment featuring a UAD in a vicinity of a garage.

Another instance of stationary structure 2750 is shown in FIG. 29. A system 29 comprising a camera 2918 and other circuitry is configured to monitor a vicinity 2955 of an opening 2942 of a garage 2936. Such circuitry (controller 2910, e.g.) controls a door 2941 of the garage 2936 within a range 2943 of its motion via a motor 2925 thereof, limited to patentable subject matter under 35 U.S.C. 101. In some variants, such circuitry further comprises one or more limited-range transceivers 2911, antennas 2912, or other sensors 2915; proximity detection modules 2921; or pattern recognition modules 2922. In some contexts, a UAD 2905 may be configured to enter or exit garage 2936 via opening 2942. In some variants, such UAD (implementing UAD 1005, e.g.) may include one or more barcodes 2961, UAD identifiers 2962, radio frequency identification (RFID) tags 2963, or authorization codes 2964 as described below.

Figure 39:
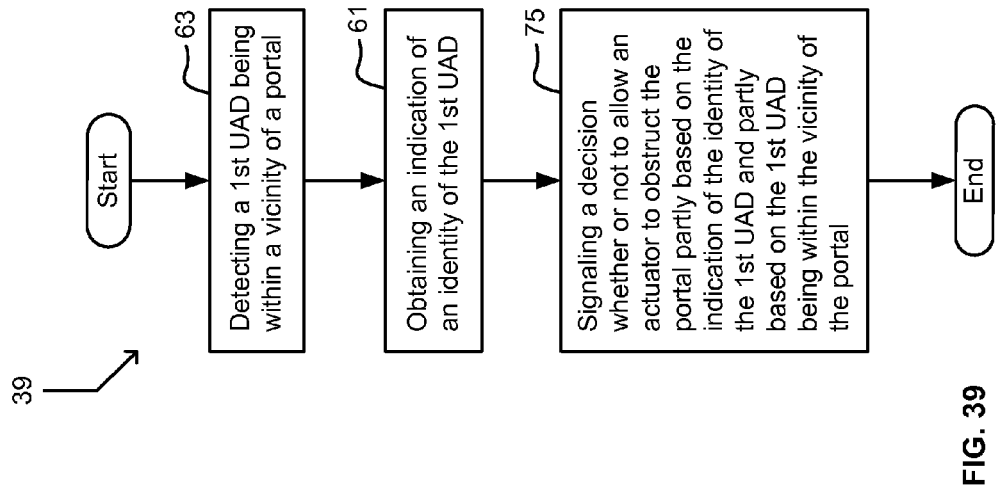
FIG. 39 depicts a high-level logic flow of an operational process described with reference to FIG. 29.

With reference now to FIG. 39, shown is a high-level logic flow 39 of an operational process. Intensive operation 63 describes detecting a first unmanned aerial device being within a vicinity of a portal (e.g. interrogation module 2530 detecting a response 3590 from UAD 2905 in a vicinity 2955 of garage door 2941). This can occur, for example, in a context in which controller 2910 includes detection unit 2500 and data handling unit 3550 and resides in or on garage 2936; in which UAD 2905 includes an RFID tag 2963 that is responsive to interrogation module 2530; and in which the vicinity 2955 is a range within which interrogation module 2530 can trigger RFID tag 2963 to transmit the response D958 and within which antenna 2912 can detect the response D958 from UAD 2905. In some contexts, for example, RFID tag 2963 may be a passive tag so that response D958 is powered entirely by interrogation module 2530.

Intensive operation 61 describes obtaining an indication of an identity of the first unmanned aerial device (e.g. optical pattern recognition module 2922 detecting a primary identifier 821 or alias 822 identifying UAD 802 on a label 2275 or other printed content on UAD 802). This can occur, for example, in a context in which such a label 2275 is affixed to UAD 802; in which UAD 802 includes primary module 3610 and implements the "first" UAD 2905; and in which optical pattern recognition module 2922 performs such processing upon image data 1242 depicting UAD 2905 (obtained via one or more cameras 2541, 2918, e.g.). Alternatively or additionally, operation 61 may be performed by a pattern recognition module 3639 generating a null or default name 2241 that initially identifies the "first" UAD 2905 (before receiving an identifier in real time, e.g.) or by the "first" UAD receiving a UAD identifier 2962 (on a barcode 2961, e.g.) that identifies it. Alternatively or additionally, in some implementations, signal detection module 3682 may perform operation 61 by receiving a wireless signal 2426 containing the identity indication 2402 (a serial number or other UAD identifier 2962, e.g.). In some variants, moreover, signal 2426 may include additional data (status-indicative data 1240 or an authorization code 2964, e.g.) as well.

Extensive operation 75 describes signaling a decision whether or not to allow an actuator to obstruct the portal partly based on the indication of the identity of the first unmanned aerial device and partly based on the first unmanned aerial device being within the vicinity of the portal (e.g. decision module 3675 transmitting a negative decision 3541 if pattern recognition module 3631 recognizes the primary identifier 821 or alias 822 identifying a UAD 802 that is within a vicinity 2955 of an entry of garage 2936). This can occur, for example, in a context in which the "actuator" comprises garage door 2941 and in which the "negative" decision 3541 is a decision (a) to raise garage door 2941 or (2) not to lower garage door 2941, either such action having the effect that the portal (opening 2942, e.g.) will not be obstructed (closed, e.g.). In some contexts, moreover, decision module 3675 may be configured to trigger the garage door 2941 to rise only partly and then immediately to close. This can occur, for example, in a context in which task implementation module 3752 triggers such closure in response to an indication that garage door 2941 has opened by ⅓ of its range 2943 or in response to sensor 2915 detecting that UAD 2905 has passed through or in response to timer 2522 detecting that 2 seconds have passed since operations 61 & 63 were complete (and that UAD 2905 has therefore had an adequate opportunity to pass through opening 2942, e.g.).

Figure 30:
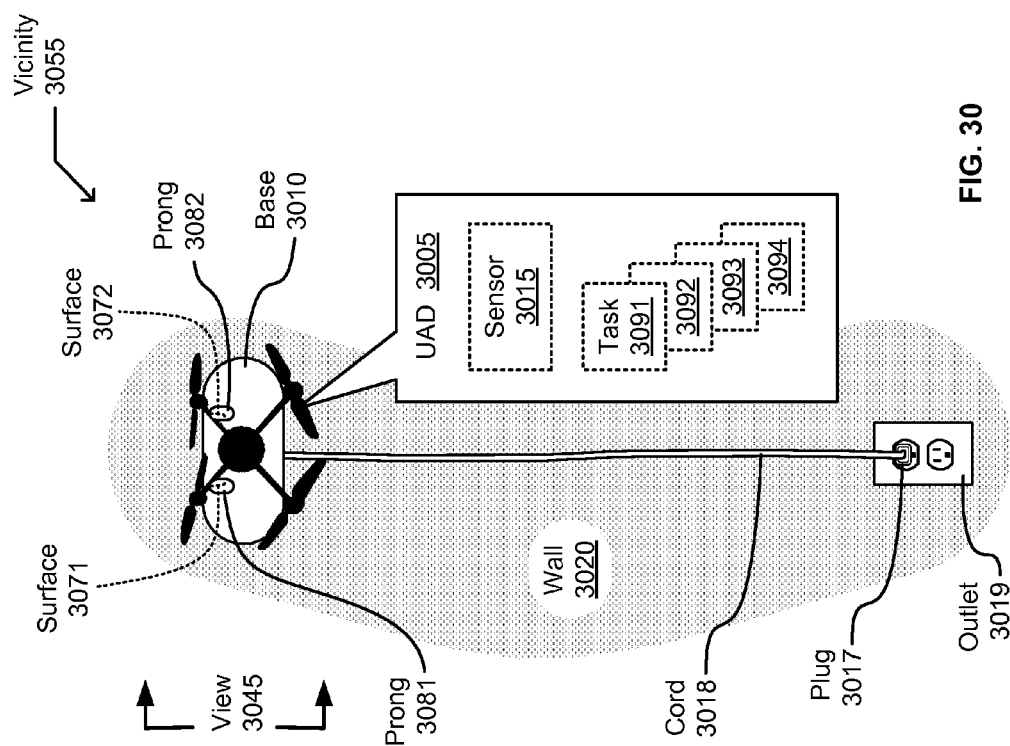
FIG. 30 depicts a front view of a structure configured to support a quadcopter-type UAD.

Another system in which one or more technologies may be implemented is shown in FIG. 30. A wall 3020 may comprise an interior or exterior structure of an office 1380, house 2845, garage 2936, or other facility described below. A base 3010 mounted onto the wall 3020 receives electrical power via a cord 3018 and plug 3017 which engages an outlet 3019 of wall 3020. Base 3010 includes one or more prongs 3081, 3082 having respective surfaces 3071, 3072 upon which a UAD 3005 may support itself. In some variants, one or more CCD's 1493 or other sensors 3015 may capture data from a vicinity of such surfaces 3071, 3072. Alternatively or additionally, UAD 3005 may be configured to perform one or more tasks 491-499, 3091, 3092, 3093, 3094 as described herein. In some context, for example, UAD 3005 may be configured to land, be recharged, or launch itself autonomously generally as described below (especially with reference to FIG. 31, which depicts a side view 3045 of base 3010, e.g.).

Figure 40:
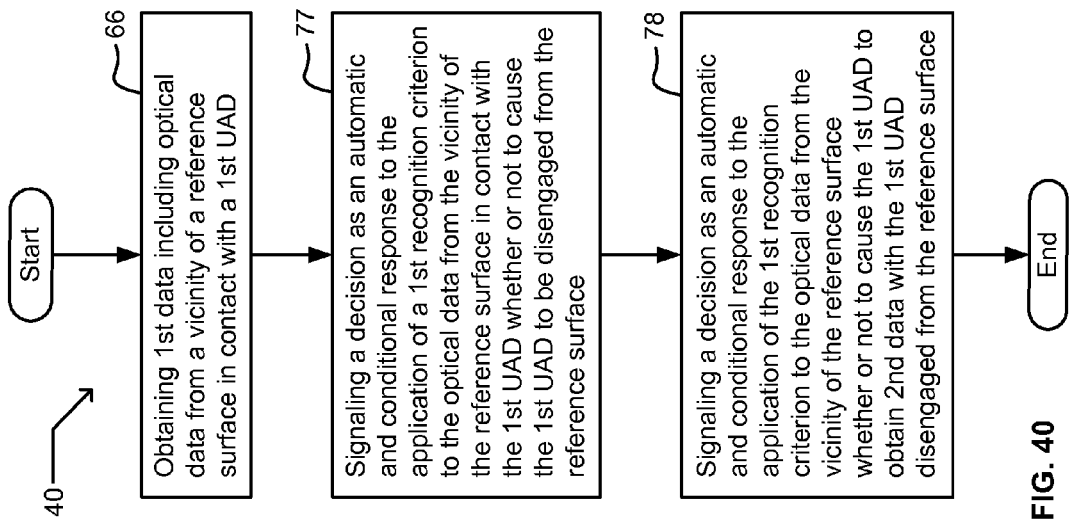
FIG. 40 depicts a high-level logic flow of an operational process described with reference to FIG. 30.

With reference now to FIG. 40, shown is a high-level logic flow 40 of an operational process. Intensive operation 66 describes obtaining first data including optical data from a vicinity of a reference surface in contact with a first unmanned aerial device (e.g. signal detection module 3681 receiving one or more images 2371 from a charge-coupled device 1493 or camera 4636 in a vicinity 3055 of one or more surfaces 3071, 3072 of a mooring structure that support UAD 3005). This can occur, for example, in a context in which the "first" data 2321 includes such optical data; in which the mooring structure comprises a base 3010 mounted upon a wall 3020 near the camera 4636 or other sensor-containing article 1400; and in which primary unit 3610 resides in UAD 3005 or base 3010. In some variants, for example, article 1400 may comprise UAD 3005 or base 3010.

Extensive operation 77 describes signaling a decision as an automatic and conditional response to the application of a first recognition criterion to the optical data from the vicinity of the reference surface in contact with the first unmanned aerial device whether or not to cause the first unmanned aerial device to be disengaged from the reference surface (e.g. optical pattern recognition module 3632 and decision module 3671 jointly transmitting a trigger 2411 instructing UAD 3005 to take off from the reference surface as a conditional result 2451 of optical pattern recognition module 3632 determining that at least one image 2371 satisfies at least one criterion 2396 specified by operator 729). This can occur, for example, in a context in which primary unit 3610 includes media 2300, 2400; in which optical pattern recognition module 3632 transmits result 2451 to decision module 3671; and in which result 2451 is a determinant by which decision module 3671 decides whether to transmit trigger 2411. In some implementations, one or more other triggers 2111-2120 may also be configured each as a determinant (as an input to decision module 3671, e.g.) that enables or prevents the transmission of trigger 2411.

Intensive operation 78 describes signaling a decision as an automatic and conditional response to the application of the first recognition criterion to the optical data from the vicinity of the reference surface whether or not to cause the first unmanned aerial device to obtain second data with the first unmanned aerial device disengaged from the reference surface (e.g. decision module 3674 implementing a decision 3542 to obtain one or more images 2372, clips, or other "second" data 2322 by invoking a detection unit 2500 or other task implementation modules 1130-1139 aboard UAD 3005 after UAD 3005 disengages from the one or more reference surfaces 3071, 3072). This can occur, for example, in a context in which UAD 3005 includes (an instance of) primary unit 3610 and secondary unit 1150; in which decision module 3674 is configured to respond directly to trigger 2411 or according to a surveillance protocol; and in which such "second" data 2322 would not otherwise be obtained from the vantage point of UAD 3005. In some contexts, for example, such a protocol may include a task sequence (executed by task implementation module 3751, e.g.) comprising a task 3091 of invoking a location detection module 3643 configured to generate location data 3482 (indicative of a position of an apparent intruder or other anomaly 2315, e.g.) from the "first" data 2321; a task 3092 of invoking one or more flight control modules 3651-3654 configured to navigate UAD 3005 from base 3010 using the location data 3482; and a task 3093 of acquiring the "second" data 2322 (periodically or continuously, e.g.) during or after such navigation (in flight, e.g.). This can occur, for example, in a context in which an intruder (a device or person, e.g.) could otherwise disable UAD 3005 (via a disablement device 2690 carried by the intruder, e.g.) before any such "second" data 2322 is acquired.

Figure 31:
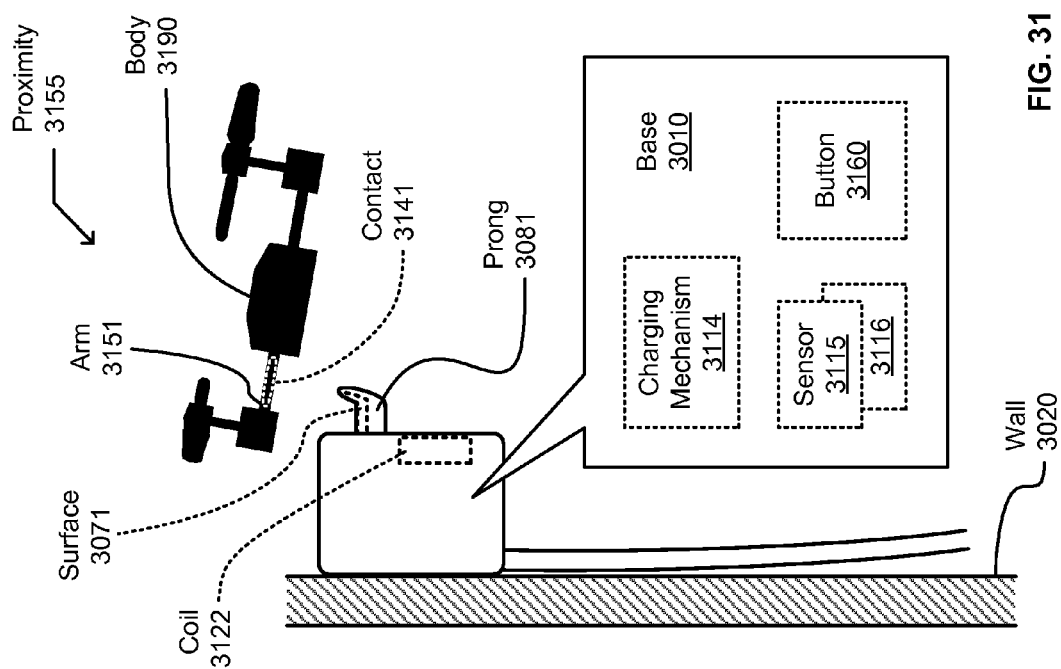
FIG. 31 depicts a side view of the structure of FIG. 30.

FIG. 31 depicts a proximity 3155 of UAD 3005 just having launched from or about to land on base 3010. When UAD 3005 is docked on base 3010, arm 3151 rests in contact with an upper inner surface 3071 of prong 3081. In some contexts base 3010 includes a charging mechanism 3114 suitable for one or more corresponding features of UAD 3005. In one implementation, for example, charging mechanism 3114 comprises a coil 3122 by which a corresponding coil (not shown) in body 3190 may receive a charging current (configured to charge a battery 2085 aboard UAD 3005. This can occur, for example, in a context in which UAD 3005 implements UAD 1005 and comprises a structure 2030 for engaging battery 2085 and in which battery 2085 is configured to power one or more motors 1081-1083. Alternatively or additionally, UAD 3005 may be configured to permit battery 2085 to be charged by a pair of electrical contacts 3141 on respective arms 3151 of UAD 3005. This can occur, for example, in a context in which charging mechanism 3114 comprises conductive surfaces 3071, 3072 configured to carry a charging voltage and engage such contacts when UAD 3005 lands. In some variants, moreover, base 3010 may include one or more sensors 3115, 3116 (comprising a camera 2541, microphone 2552, or other sensors 2560 described herein, e.g.); one or more buttons 3160 by which operator 729 may trigger UAD 3005 (to perform a surveillance or delivery task, e.g.); or other unit features described herein.

Figure 41:
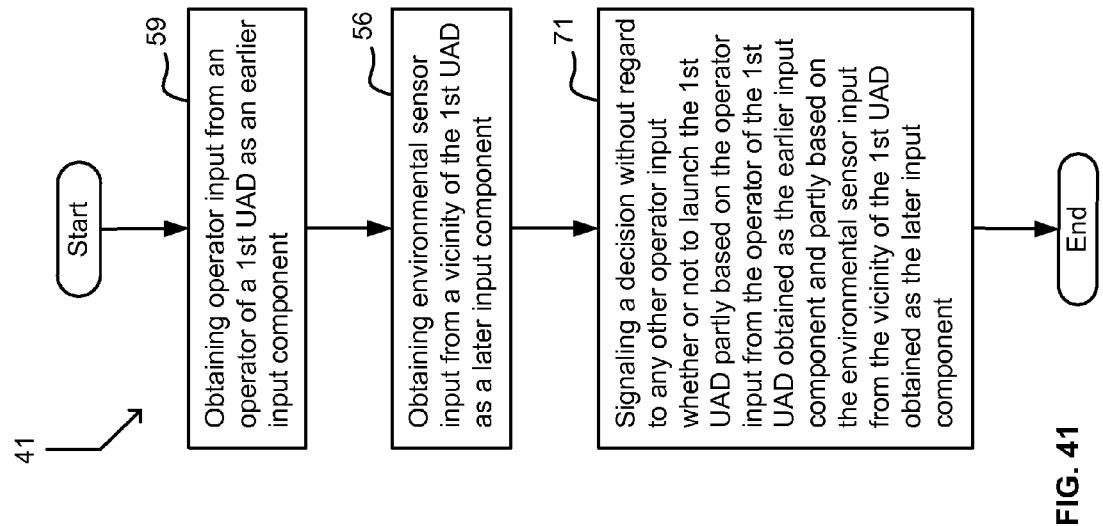
FIG. 41 depicts a high-level logic flow of an operational process described with reference to FIG. 31.

With reference now to FIG. 41, shown is a high-level logic flow 41 of an operational process. Intensive operation 59 describes obtaining operator input from an operator of a first unmanned aerial device as an earlier input component (e.g. operator interface B660 receiving device-executable code 2461 as input 3583 from a programmer or other operator 729 of UAD 3005 on "day zero"). This can occur, for example, in a context in which operator 729 has physical access to an operator interface 3713 (a mode control switch or button 3160, e.g.) of base 3110; in which UAD 3005 can receive such device-executable code 2461 (as an upgrade or patch, e.g.) directly via an electrical conduit (contact 3141, e.g.) or otherwise while docked on base 3010; and in which UAD 3005 includes a processor 365 configured to cause UAD 3005 to perform one or more tasks 491-499, 3091-3093 implemented within such code 2461. In some contexts, for example, such code defines one or more automatic or other triggers 2111-2119, 2411-2416 configured to cause such task performance to begin. Alternatively or additionally, such input 3583 can include task implementation modules 1130-1139 installed into UAD 3005 earlier (during manufacture, e.g.).

Intensive operation 56 describes obtaining environmental sensor input from a vicinity of the first unmanned aerial device as a later input component (e.g. heat sensor 2555 generating thermal data 2324 indicating an indoor fire in a vicinity 3055 of UAD 3005 as "later" environmental sensor input 3585 one or more days after "day zero"). This can occur, for example, in a context in which secondary unit 3750 implements medium 2400 and data handling unit 3550; in which primary unit 3610 implements event/condition detection unit 400; in which base 3010 includes one or both of primary unit 3610 and secondary unit 3750; in which detection unit 2500 resides in either UAD 3005 or base 3010; and in which comparator 3741 detects whether thermal data 2324 exceeds a thermal threshold 2333 as a trigger 2415 for a task implementation module described herein (configured to invoke flight control module 3651, e.g.).

Extensive operation 71 describes signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component (e.g. flight control module 3651 causing UAD 3005 to launch in response to particular sensor input 3585 irrespective of whether any operators 729 of UAD 3005 provide further input 3584 after the "day zero" operator input 3583). This can occur, for example, in a context in which the "day zero" operator input 3583 configures a task implementation module 3753 of UAD 3005 to be (potentially) triggered by sensor input 3585 indicative of fire by generating a fire-indicative trigger 2415, 2416 in response to which flight control module 3651 launches UAD 3005; in which such sensor input 3585 is received from one or more cameras 2541 or other optical sensors 2545 or microphones 2552 or carbon monoxide sensors 2553 or smoke sensors 2554 or heat sensors 2555; and in which no further operator input 3584 (after the "day zero" input) is received. In some contexts, moreover, task implementation module 3753 may be configured to disregard or otherwise do without further operator input 3584 (confirmations, e.g.) received via operator interface B660. In some variants, moreover, UAD 3005 may be configured to investigate the premises (a room or house 2845 including vicinity 3055, e.g.) and transmit data 2325 acquired via a sensor 3015 aboard UAD 3005 (as wireless signal 2422, e.g.) within a few minutes after such launch.

FIG. 32 depicts a context in which one or more technologies may be implemented. A first entity 3201 (UAD 1005, e.g.) may follow a path 3270 through a sequence of positions 3241, 3242, 3243. Each position 3241 may be described with reference to corresponding coordinates 3221, 3222, 3223 in a coordinate system (featuring at least an X-axis 3221 and a Y-axis 3222, e.g.). In some contexts, entity 3201 can detect or be detected by a second entity 3202 (via one or more energy signature paths 3271, 3272 along which light or sound may travel, e.g.) which detection may affect which path 3271, 3272 entity 3201 will follow subsequently.

With reference now to FIG. 42, shown is a high-level logic flow 42 of an operational process. Intensive operation 58 describes obtaining first data including an X-ordinate of a first location and a Y-ordinate of the first location indicating a first entity moving from the first location to a second location (e.g. global positioning system 1063 generating GPS data 3481 that signals position 3241 and an indication 2405 of entity 3201 moving southward). This can occur, for example, in a context in which distillation unit 3480 is operably coupled with entity 3201; in which position 3241 is the "first" location; in which the "first" entity 3201 comprises a helicopter 1002 or other mobile device 1010 described above; in which data 3481 includes an instance of longitude (X-ordinate 2231, e.g.) and latitude (Y-ordinate 2232, e.g.) and altitude (Z-ordinate 2233, e.g.); and in which indication 2405 signals a particular location (position 3242 or a waypoint thereof, e.g.) or heading or apparent direction of travel.

Intensive operation 60 describes obtaining second data indicative of a device-detectable energy signature path having existed between a second entity and the first location (e.g. signal detection module 3683 recognizing a radio frequency signal 2423 or optical signal 2424 transmitted by entity 3202 and received by entity 3201). This can occur, for example, in a context in which entity 3201 includes one or more antennas 455 that receive RF signal 2423 or optical sensors 2545 that receive optical signal 2424 via path 3271; in which path 3271 is sufficiently direct to permit such wireless signal travel; and in which one or more such signals 2423, 2424 are strong enough to be detectable when received at position 3241. In some contexts, for example, entity 3201 includes both an antenna 455 and an optical sensor 2545 so that operation 60 may occur even in a context in which path 3271 is only permeable to one of these signals 2423, 2424. Alternatively or additionally, (an instance of) primary detection module 3610 may reside aboard entity 3201.

Intensive operation 62 describes obtaining third data indicative of no device-detectable energy signature path having existed between the second entity and the second location (e.g. signal detection module 3684 recognizing a failure to detect radio frequency signal 2423 or optical signal 2424 transmitted by entity 3202 at position 3242). This can occur, for example, in a context in which entity 3201 includes one or more antennas 455 configured to receive RF signal 2423 except for the fact that no suitable RF signal path exists from entity 3202 to position 3242. In some contexts, for example, operation 62 can occur (because of a blocked or other unsuccessful transmission from entity 3202, e.g.) after several instances of operation 60 (resulting from successful transmissions from entity 3202, e.g.) have occurred. Alternatively or additionally, signal detection module 3684 can perform operation 62 in a context in which entity 3201 includes one or more optical sensors 2545 configured to receive optical signal 2424 except for the fact that no suitable optical signal path exists from entity 3202 to position 3242. (It will be understood that even if gamma radiation were intentionally transmitted westward toward position 3242, the path 3272 along which it travels is not a "device-detectable energy signature path" unless one or more devices are configured to detect it.)

Extensive operation 76 describes causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location (e.g. navigation module 3661 responding to signal detection module 3683 indicating that path 3271 is apparently viable and to signal detection module 3684 indicating that path 3272 is apparently not viable by routing entity 3201 from a current "third" position 3243 back toward the "first" location 3241). This can occur, for example, in a context in which location 3241 is characterized with the X-ordinate 2231 and the Y-ordinate 2232 and in which navigation module 3661 routes entity 3201 along any of the available paths 3271, 3272 in a direction of travel that will cause entity 3201 to draw nearer to the "first" position 3241.

In light of teachings herein, numerous existing techniques may be applied for configuring special-purpose circuitry or other structures effective for configuring a device to navigate without undue experimentation or for configuring other decisions and devices as described herein. See, e.g., U.S. Pat. No. 8,229,163 ("4D GIS based virtual reality for moving target prediction"); U.S. Pat. No. 8,224,508 ("Viewing device for aircraft comprising means of displaying the final destination and associated display method"); U.S. Pat. No. 8,090,526 ("Method for determining the horizontal profile of a flight plan complying with a prescribed vertical flight profile"); U.S. Pat. No. 7,881,864 ("Method and apparatus for utilizing geographic location information"); U.S. Pat. No. 7,865,277 ("Obstacle avoidance system and method"); U.S. Pat. No. 7,617,024 ("Automatic heading control system for tiltrotor aircraft and helicopters"); U.S. Pat. No. 7,228,232 ("Navigating a UAV with obstacle avoidance algorithms"); U.S. Pat. No. 7,127,334 ("System and methods for preventing the unauthorized use of aircraft"); U.S. Pat. No. 6,892,135 ("Navigation system, method and device with automatic next turn page"); U.S. Pat. No. 6,694,228 ("Control system for remotely operated vehicles for operational payload employment").

Figure 33:
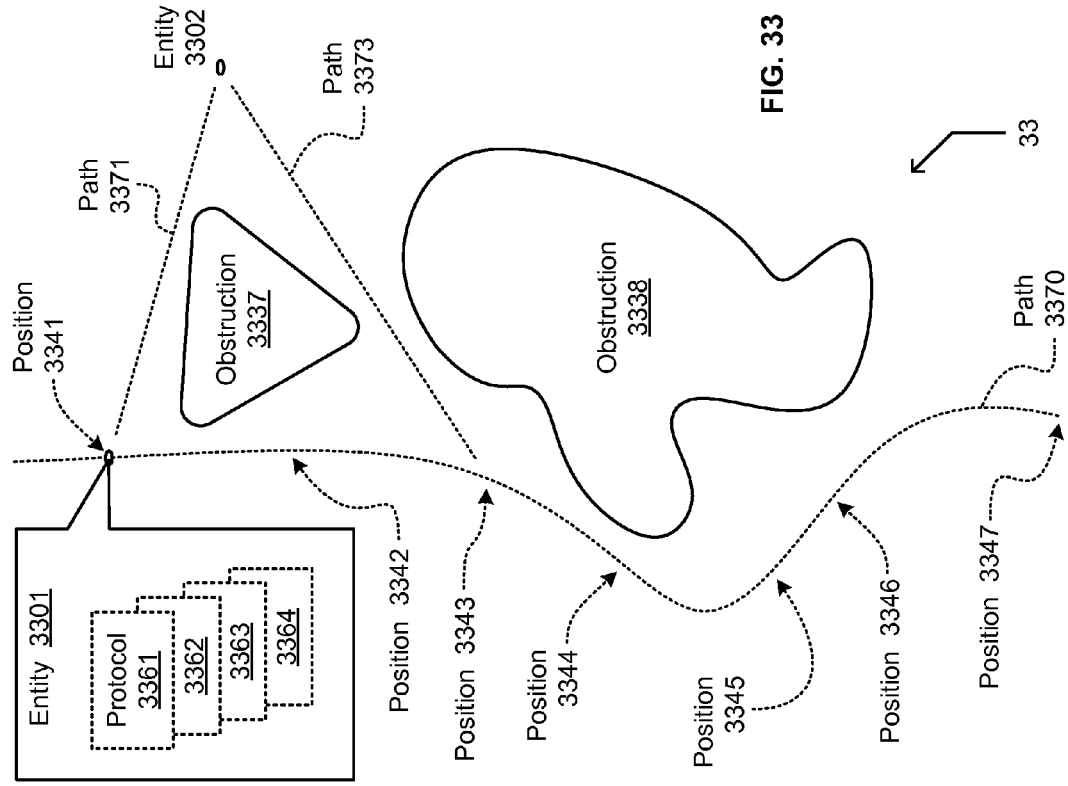
FIG. 33 depicts entities like those of FIG. 32, one only intermittently able to obtain an indication of another due to intervening obstacles.

FIG. 33 depicts a context in which one or more technologies may be implemented, a system 33 comprising first and second entities 3301, 3302. The first entity 3301 (UAD 1005, e.g.) is mobile and may travel along path 3370 through a series of positions 3341, 3342, 3343, 3344, 3345, 3346, 3347 depending upon which navigation protocol 3361, 3362, 3363, 3364 it follows. The second entity may be a mountain or building 935 or person 727 or UAD 1005 or other mobile or stationary entity. In either case, entity 3301 may (optionally) be configured to detect entity 3302 at some positions 3341, 3343 (via respective energy signature paths 3371, 3373, e.g.) as it travels. Alternatively or additionally, an entity 3302 that is a device may be configured to detect entity 3301 at some positions 3341, 3343 (via respective energy signature paths 3371, 3373, e.g.) as it travels. When entity 3301 is in some other positions 3342, 3346, no such detection is possible because one or more obstructions 3337, 3338 (buildings or trees, e.g.) prevent the existence of any device-detectable energy signature path between the first and second entities 3301, 3302.

Figure 43:
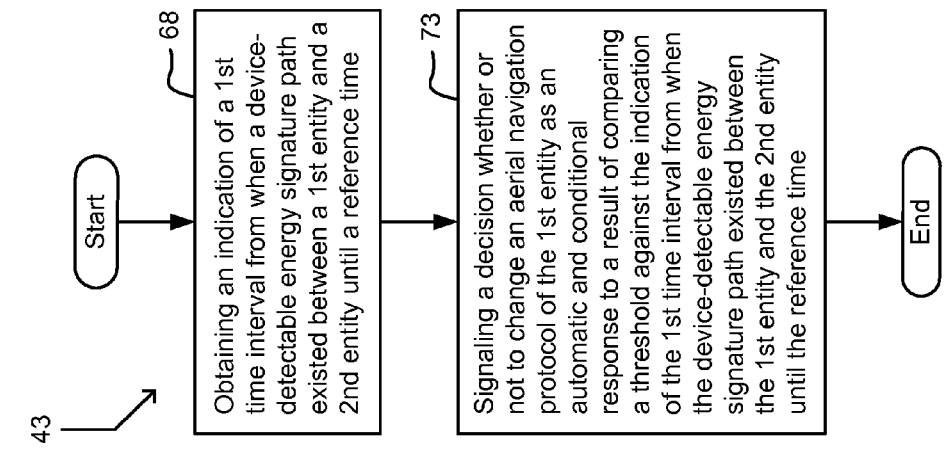
FIG. 43 depicts a high-level logic flow of an operational process described with reference to FIG. 33.

With reference now to FIG. 43, shown is a high-level logic flow 43 of an operational process. Intensive operation 68 describes obtaining an indication of a first time interval from when a device-detectable energy signature path existed between a first entity and a second entity until a reference time (e.g. estimation module 3771 computing a difference 3520 between an initial time 2381 at which entity 3301 was at position 3341 until a later time 2382 at which entity 3301 was at position 3342). This can occur, for example, in a context in which a first energy signature path P371 existed between the first and second entities 3301, 3302 when entity 3301 was at position 3341; in which entity 3301 comprises one or more unmanned aerial devices 1005 traveling southward (along path 3370, e.g.) according to a first navigation protocol 3361; in which no such energy signature path existed between the first and second entities 3301, 3302 when entity 3301 was at position 3342 (due to an opaque object or other obstruction 3337 therebetween, e.g.); and in which a timer 1141 (aboard entity 3301 or other instance of secondary unit 1150, e.g.) indicates one or more relevant times 2381-2388 to estimation module 3781. In some contexts, for example, energy signature path 3371 may comprise a line of sight (along which light reflected by entity 3302 may travel, e.g.) or some other path (a generally direct route through air 585, e.g.) viable for wireless signal transmissions (in an auditory frequency range 2465 or RF range 2475, e.g.). In other contexts, the "second" entity 3302 may be operable to transmit a distinctive optical signal 2427 (an authorization code 2964, e.g.) along energy signature path 3371.

Extensive operation 73 describes signaling a decision whether or not to change an aerial navigation protocol of the first entity as an automatic and conditional response to a result of comparing a threshold against the indication of the first time interval from when the device-detectable energy signature path existed between the first entity and the second entity until the reference time (e.g. flight control module 3652 implementing a decision 3549 to guide entity 3301 conditionally according to a new/latter navigation protocol 3362 if comparator 3742 indicates that time interval 2342 exceeds an operator-defined threshold 2332 and otherwise generally not implementing such a decision 3549). This can occur, for example, in a real-time implementation (in which the "reference" time is nominally the present, e.g.) in which timer 2524 indicates a time interval 2342 from when entity 3301 was at position 3341 until the present; in which threshold 2332 indicates a operator-defined time interval of more than ten seconds; and in which entity 3301 generally would otherwise have continued to use a prior/default navigation protocol 3361 by which entity 3301 would have stayed on a nominally southward path 3370 of travel). In some contexts, for example, navigation protocol 3362 is configured to cause entity 3301 to travel along a nominally northward or other path of travel other than path 3370. Alternatively or additionally, threshold 2332 may indicate a time interval of less than ten minutes.

In some variants, for example, primary unit 3610 and secondary unit 3750 may each reside within "first" entity 3301 or within a "third" entity (near position 3344, e.g.) in wireless communication with the "first" entity 3301. This can occur in a context in which the "third" entity is an unmanned aerial device 803, for example, or a stationary structure 2750. In one scenario, timer 1141 begins to run (upward, in some variants) as entity 3301 travels south from a position 3341 from which the "second" entity 3302 was visible. Obstruction 3337 prevents entity 3302 from being visible as entity 3301 passes position 3342 but entity 3301 continues to follow protocol 3361 because difference 3520 is still smaller than threshold 2332 and so decision 3549 is negative. As entity 3301 reaches position 3343 (at time 2383, e.g.) another device-detectable energy signature path 3373 (from entity 3302, e.g.) is observed and so timer 1141 is reset (to its initial value, e.g.). Flight control module 3652 thus continues to implement protocol 3361 at several positions 3344, 3345, 3346 so long as difference 3520 (between time 2383 and respective times 2384 and 2385 and 2386, e.g.) remains smaller than threshold 2332. But as entity 3301 reaches position 3347 comparator 3742 signals that the difference 3520 between times 2383, 2387 became larger than threshold 2332, in response to which flight control module 3652 begins to implement one or more other protocols 3362, 3363 instead. In respective variants, for example, flight control module 3652 may select between such other protocols 3362, 3363 in response to one or more enabling or other criteria 2390-2399 described herein. In some contexts such a protocol 3363 may be performed pursuant to an implementation of one or more other flows 15-19, 41-47 described herein, for example.

FIG. 34 depicts a context in which one or more technologies may be implemented. An image 3484 shows an unmanned aerial device 3401 sitting atop a vehicle of a person using a drive-up automated teller machine (ATM) 3410. In some contexts such images (depicting UAD 3401, e.g.) may be taken by a camera 3415 of a second UAD 3402 or a stationary camera 3417. This and other data 3426 (from sensor 3416, e.g.) may be distilled by a data handling module 3425 aboard UAD 3402 (implementing an event/ condition detection unit 400 or decision modules described herein, e.g.). Alternatively or additionally, such data 3426 may be aggregated (with other data 3481, 3482, 3483 pertaining to positions of entities described herein, e.g.) and processed regionally (by one or more anomaly detection modules 3485, e.g.). In some contexts, such distillation may affect whether or when subsequent notifications (to ATM 3410, e.g.) or archiving (to one or more media 3495 in network 3490, e.g.) or other responses will occur, as described herein.

With reference now to FIG. 44, shown is a high-level logic flow 44 of an operational process. Intensive operation 57 describes obtaining photographic data depicting a first unmanned aerial device (e.g. data aggregation module 3791 receiving one or more images 2374, 3484 showing an unknown UAD 3401). This can occur, for example, in a context in which secondary unit 3750 resides in distillation unit 3480 or network 3490 and in which image 3484 was initially captured by a camera 3415 aboard UAD 3402. Alternatively or additionally, the photographic data (image 2374, e.g.) depicting UAD 3401 may have been captured initially via one or more sensors 2560 (camera 3417, e.g.) comprising a stationary structure (ATM 3410, e.g.).

Intensive operation 65 describes obtaining an indication whether or not the first unmanned aerial device behaved anomalously (e.g. anomaly detection module 3485 applying a positional criterion 2390 to data 3483 indicative of an approximate location 2240 of UAD 3401 to generate an indication 2407 of whether UAD 3401 is in a region that is use-restricted or off limits). Such a region may comprise a house 2845, parcel 2840 of land, facility (a hospital or bank, e.g.), office 1380 or other room, elevation range, or other (2-dimensional or other) zone 782. In some contexts, for example, such a region or its uses may be expressed in terms of its converse (a permissible zone of operation or activity therein, e.g.) or affected by other circumstances (time of day or presence or absence of personnel, e.g.). In some contexts, a device (UAD 2802, e.g.) may implement one or more use restriction definitions 2471-2475 applicable to devices or personnel within a zone 782. Definition 2471 may permit only particular UAD's 701, 801 to perform identified tasks 491-499 within the region. Definition 2472 may forbid any UAD from flying within a given distance 2237 (specified by a facility owner or city ordinance, e.g.) of any mobile entity (animal or car 602 or other device, e.g.) within the region. Definition 2473 may require continuous movement or flight of any UAD's within the region. Definition 2474 may require any UAD within the region either to identify itself (by transmitting a, e.g.) or its purpose (by transmitting one or more task identifiers 4501-4503, e.g.) or to leave within a particular time interval (1-3 minutes, e.g.). In respective variants, anomaly detection module 3485 may be configured to detect anomalous behavior as any deviation from one or more such use restriction definitions 2471-2475 in effect. In some variants, for example, anomaly detection module 3485 may be configured to respond to such deviation by transmitting trigger 2413.

In light of teachings herein, numerous existing techniques may be applied for configuring special-purpose circuitry or other structures effective for distilling indications of anomalous behavior without undue experimentation or for config-uring other decisions and devices as described herein. See, e.g., U.S. Pat. No. 8,098,142 ("Vehicle monitoring system"); U.S. Pat. No. 8,041,664 ("Supervisory control by non-humans"); U.S. Pat. No. 7,983,447 ("Imaging environment recognition device"); U.S. Pat. No. 7,893,960 ("Smart sensors for perimeter and border security"); U.S. Pat. No. 7,737,878 ("Collision and conflict avoidance system for autonomous unmanned air vehicles (UAVs)"); U.S. Pat. No. 7,598,888 ("Rotary wing aircraft proximity warning system with a geographically based avoidance system"); U.S. Pat. No. 7,346,188 ("Motion detection method and device, program and vehicle surveillance system"); U.S. Pat. No. 7,280,696 ("Video detection/verification system"); U.S. Pat. No. 7,154,275 ("Method and apparatus for detecting individuals using electrical field sensors"); U.S. Pat. No. 7,093,294 ("System and method for detecting and controlling a drone implanted in a network attached device such as a computer"); U.S. Pat. No. 7,027,808 ("System and method for monitoring and control of wireless modules linked to assets"); U.S. Pat. No. 6,965,816 ("PFN/TRAC system FAA upgrades for accountable remote and robotics control to stop the unauthorized use of aircraft and to improve equipment management and public safety in transportation"); U.S. Pat. No. 6,734,799 ("Apparatus and method for responding to the health and fitness of a driver of a vehicle").

Extensive operation 74 describes signaling a decision whether or not to transmit the photographic data depicting the first unmanned aerial device as an automatic and conditional response to the indication whether or not the first unmanned aerial device behaved anomalously (e.g. data distillation module 3783 transmitting one or more images 2374, 3484 indicative of current or recent circumstances near UAD 3402 to medium 3495 if trigger 2413 is received and otherwise generally not transmitting such status-indicative data 1240). This can occur, for example, in a context in which image data 1241 includes video data or other images 2161-2165, 2371-2377, 3484; in which status-indicative data 1240 includes GPS data 1242, timing data 1243, or other data derived from sensor input 3582; in which data aggregation module 3791 and anomaly detection module respectively perform operations 57 and 65; and in which data distillation unit 3480 filters out (by data sampling or other selective extraction, e.g.) a portion of status-indicative data 1240 that it receives. In some contexts, for example, distillation unit 3480 may reside aboard UAD 3402. Alternatively or additionally, distillation unit 3480 may be configured to pass an alarm or other anomaly-indicative message 2356 as a real-time response (via a speaker 1171 of UAD 3402 or a display 1172 of ATM 3410, e.g.).

Figure 45:
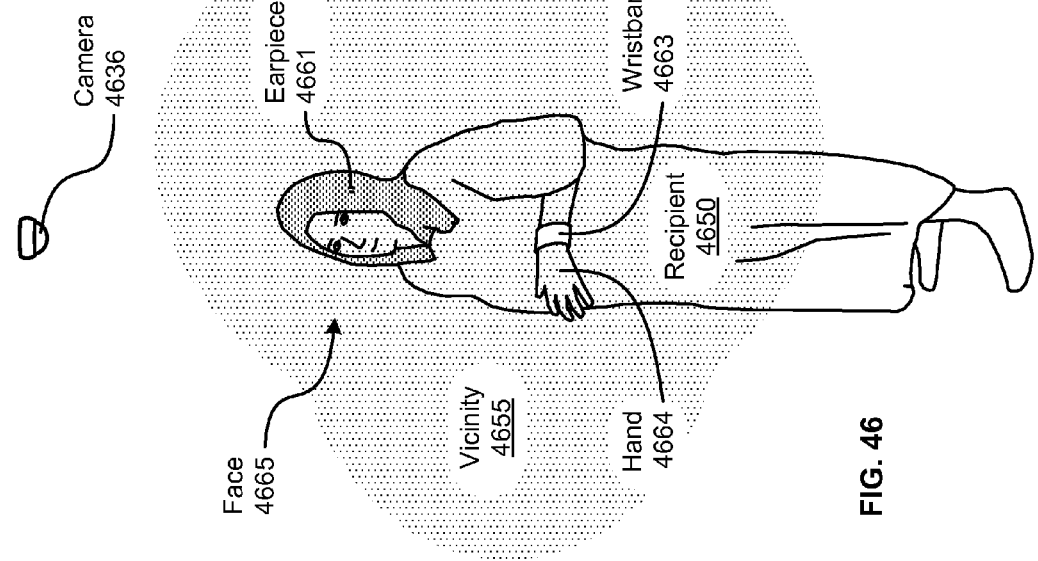
FIG. 45 depicts physical media residing in one or more of the above-described environments.

Another context in which one or more technologies may be implemented is shown in FIG. 45. A medium 4500 (configured to implement storage or transmission or display, e.g.) may bear one or more instances of job records 4510; data 4550, 4551, 4552, 4553 (comprising measurements 4511, 4512, 4513, 4514 or images or other results 4521, 4522, 4523, 4524, 4525, e.g.); triggers 4581, 4582, 4583, 4584; thresholds 4591, 4592, 4593, 4594; or components of other media 195, 410, 1200, 2100 described above. In some variants, for example, a job record may include one or more task identifiers 4501, 4502, 4503 configured to identify, in respective embodiments, any of the other tasks indicated herein to be implemented in one or more devices.

Figure 46:
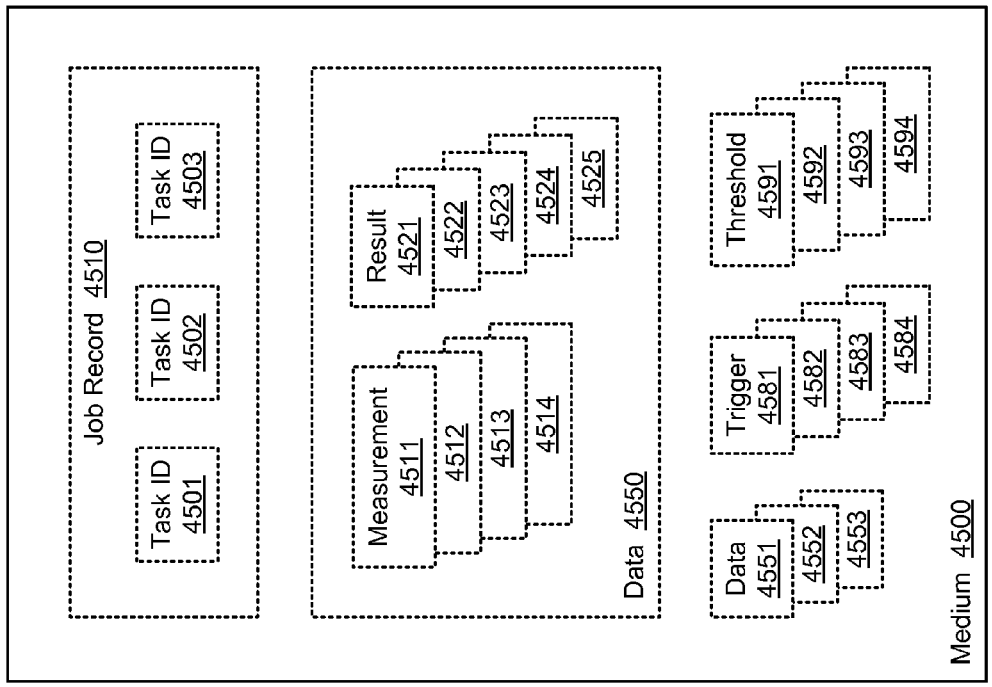
FIG. 46 depicts an exemplary environment featuring a camera mounted on a building configured to observe a person.

Another context in which one or more technologies may be implemented is shown in FIG. 46. A mounted camera 4636 (supported by a building or other stationary structure, e.g.) is configured to observe one or more instances of a particular person (a recipient 4650 of a delivery, e.g.) or a portion thereof (a hand 4664 or face 4665, e.g.) or a wearable device (an earpiece 4661 or wristband 4663, e.g.) or a partial or entire vicinity 4655 (room or other facility, e.g.) of one of these entities. Moreover in some contexts, as further described below, recipient 4650 may be a user of one or more of the above-described devices (in vicinity 4655, e.g.).

With reference now to flow 47 of FIG. 47 and to other flows 15-19 and 38-44 described above, in some variants, one or more intensive operations 4711, 4716, 4718 described below may (optionally) be performed in conjunction with one or more intensive operations 51-55 described above. Alternatively or additionally, extensive operation 4793 described below may likewise comprise or be performed in conjunction with one or more extensive operations 81-85 described above.

Intensive operation 4711 describes configuring the first unmanned aerial device to perform a first observation of a particular task in a first zone and a second unmanned aerial device to perform a second observation of the particular task in a second zone (e.g. task implementation module 1138 transmitting a trigger 4582 causing UAD 801 to capture an audio or video clip 2151 of a person 726 carrying UAD 701 seeking device 775 in zone 781 and also transmitting a trigger 4583 instructing UAD 802 to capture an audio or video clip 2152 of the person 726 seeking device 775 in zone 782). This can occur, for example, in a context in which one or more UAD's 701 or people 726 are performing the particular task 499 (monitoring person 726 seeking device 775, e.g.) across one or more zone boundaries 789; in which secondary unit 3750 includes event/condition detection unit 400 and media 2100, 4500; in which at least one UAD 801, 802 contains or otherwise interacts with secondary unit 3750; in which such UAD's 801, 802 or people 726 have different UAD operating restrictions in respective zones 781, 782 (UAD 801 lacking permission to move or transmit only within zone 782, for example, or UAD 802 lacking permission to move or transmit only within zone 781); and in which adequate surveillance of the entire task 499 would otherwise be prohibited (by the owners of the respective zones 781, 782, e.g.).

In light of teachings herein, numerous existing techniques may be applied for configuring special-purpose circuitry or other structures effective for coordinating surveillance among two or more observers without undue experimentation or for configuring other decisions and devices as described herein. See, e.g., U.S. Pat. No. 8,180,107 ("Active coordinated tracking for multi-camera systems"); U.S. Pat. No. 7,947,936 ("Apparatus and method for cooperative multi target tracking and interception"); U.S. Pat. No. 7,739,157 ("Method of tracking the real time location of shoppers, associates, managers and vendors through a communication multi-network within a store"); U.S. Pat. No. 7,647,232 ("Real-time team coordination system for reconnaissance and surveillance missions"); U.S. Pat. No. 7,295,106 ("Systems and methods for classifying objects within a monitored zone using multiple surveillance devices"); U.S. Pat. No. 6,999,876 ("Modular architecture for rapid deployment and coordination of emergency event field surveillance"); U.S. Pat. No. 6,963,279 ("System and method for transmitting surveillance signals from multiple units to a number of points"); U.S. Pat. No. 6,577,976 ("Method for dynamic autocalibration of a multi-sensor tracking system and apparatus incorporating it therein"); U.S. Pat. No. 6,333,718 ("Continuous multi-satellite tracking"); U.S. Pat. No. 6,084,827 ("Dual-head multibeam sonar apparatus and method for tracking objects underwater"); U.S. Pat. No. 6,055,523 ("Method and apparatus for multi-sensor, multi-target tracking using a genetic algorithm").

Intensive operation 4716 describes configuring the first unmanned aerial device to capture normalcy-indicative data relating to a human subject (e.g. task implementation module 1135 causing, by transmitting an appropriate trigger 4581, a data capture module 1108 to record one or more scalar measurements 4511-4514 or other data 4550-4553 directly or indirectly indicative of whether or not an item recipient 555, user 226, 626 or other human subject meets one or more recognizable criteria indicative of the human subject being impaired or otherwise abnormal). This can occur, for example, in a context in which a primary unit 3610 contains a data capture module 1108 of one secondary unit 1150 and receives the trigger 4581 from another secondary unit 3750; in which data 4551 comprises a video clip of the human subject taking something (a purse, e.g.) previously carried by another and then running away (at a pace greater than 4 miles per hour within 5 seconds of the taking event, e.g.); and in which primary unit 3610 also implements one or more media 4500 of a "first" UAD as described above. See, e.g., FIG. 2 or 5-10. In some contexts, such optically detectable events 1414 or conditions may be recognizable (as negatively indicative of normalcy, e.g.) by a corresponding optical condition detection module 1404 or by security personnel remotely viewing such data 4550. Alternatively or additionally, data 4552 may comprise (1) an infrared image indicating warmer-than-normal or cooler-than-normal regions of the human subject's skin; (2) one or more scalar measurements 4511, 4512 of the subject's body temperature, exhaled gas analysis (detecting a ketone concentration or other indication of intoxication, e.g.), rates (of respiration, speech, movement, or heartbeats, e.g.), or other such biometric parameters. Such events 1415 or conditions may be device-detectable or humanly recognizable (as negatively indicative of normalcy, e.g.) by a corresponding optical condition detection module 1404, by another pattern recognition module 1421, or by a person remotely viewing such data 4551-4553 in real time. In some contexts, for example, pattern recognition module 1421 may comprise a comparator 1401 configured to generate one or more results 4521, 4522 ("normal," e.g.) of comparing one or more performance or biometric measurements 4511-4513 of a user 226, 626 each against one or more corresponding normalcy-indicative thresholds 4591-4593 (maxima, e.g.). Such recognition may, for example, trigger the "first" UAD to obtain additional images or measurements 4514 pertaining to the apparent normalcy of the human subject.

In light of teachings herein, numerous existing techniques may be applied for configuring special-purpose circuitry or other structures effective for obtaining measurements, comparison results, or other normalcy-indicative data without undue experimentation or for configuring other decisions and devices as described herein. See, e.g., U.S. Pat. No. 8,135,957 ("Access control system based on brain patterns"); U.S. Pat. No. 8,061,842 ("Method of eye aliveness testing and device for eye aliveness testing"); U.S. Pat. No. 7,809,163 ("Method for prohibiting a person with a facial mask to operate an automatic teller machine"); U.S. Pat. No. 7,840,346 ("Real time performance comparison"); U.S. Pat. No. 7,571,101 ("Quantifying psychological stress levels using voice patterns"); U.S. Pat. No. 7,825,815 ("Apparatus, systems, and methods for gathering and processing biometric and biomechanical data"); U.S. Pat. No. 7,733,214 ("System and methods for the remote measurement of a person's biometric data in a controlled state by way of synchronized music, video and lyrics"); U.S. Pat. No. 8,094, 009 ("Health-related signaling via wearable items"); U.S. Pat. No. 8,145,199 ("Controlling mobile device functions"); U.S. Pat. No. 8,211,035 ("System and method for monitoring health using exhaled breath"); U.S. Pat. No. 7,477,993 ("Multiple sensing system and device"); U.S. Pat. No. 8,172,459 ("Apparatus and method for measuring biologic parameters"); U.S. Pat. No. 8,108,083 ("Vehicular system which retrieves hospitality information promoting improvement of user's current energy value based on detected temporal change of biological condition"); U.S. Pat. No. 7,787,663 ("System and method for detecting thermal anomalies").

Intensive operation 4718 describes causing the first unmanned aerial device to undertake a performance observation task of a job that includes a performance task and the performance observation task (e.g. task implementation module 1137 transmitting to UAD 501, as the "first" UAD, a task identifier 4501 corresponding to a task description 1251 calling for specific status-indicative data 1240 relating to another device 1010 undertaking to fulfill a performance task description 1252 corresponding to task identifier 4502). This can occur, for example, in which secondary unit 3750 and media 1200, 4500 reside aboard UAD 501; in which the "performance" specified by task description 1252 comprises delivering an envelope 551; in which task description 1251 relates to obtaining one or more of image data 1241 (including photograph 553, e.g.), GPS data 1242 (of destination 530, e.g.), or timing data 1243 documenting the delivery; and in which such observation and performance are respectively identified by task identifiers 4501, 4502 of a single common job record 4510. Alternatively or additionally, such task description 1251 and other task descriptions 1252, 1253 may comprise job description or other task-related data 1250 managed and delegated by a common task implementation module 1137. Other such task identifiers or descriptions may (optionally) comprise a scalar or other operating parameter 2126 of one or more triggers 421-423, 2111-2120 transmitted by task implementation modules 1130-1139, for example, as described herein.

In light of teachings herein, numerous existing techniques may be applied for configuring special-purpose circuitry or other structures effective for assigning tasks to respective devices without undue experimentation or for configuring other decisions and devices as described herein. See, e.g., U.S. Pat. No. 7,945,470 ("Facilitating performance of submitted tasks by mobile task performers"); U.S. Pat. No. 8,127,300 ("Hardware based dynamic load balancing of message passing interface tasks"); U.S. Pat. No. 7,716,667 ("Migrating virtual machines among computer systems to balance load caused by virtual machines"); U.S. Pat. No. 8,200,084 ("Encoding for information needed for routing and wavelength assignment in wavelength switched optical networks"); U.S. Pat. No. 8,181,168 ("Memory access assignment for parallel processing architectures"); U.S. Pat. No. 7,665,092 ("Method and apparatus for distributed state-based load balancing between task queues"); U.S. Pat. No. 8,184,860 ("Image processing device for controlling a plurality of tasks"); U.S. Pat. No. 7,996,893 ("Determining roles for automated tasks in a role-based access control environment"); U.S. Pat. No. 8,184,860 ("Image processing device for controlling a plurality of tasks").

Extensive operation 4793 describes configuring the first unmanned aerial device to transmit a wireless signal indicative of having performed a particular task and not to store any indication of having performed the particular task (e.g. task implementation module 1136 transmitting a trigger 2114 to which a component of UAD 1005 responds by transmitting one or more optical or other wireless signals 454 indicative of UAD 1005 having completed a particular task 491-499 without any component borne by UAD 1005 storing any indication of the particular task having been performed). This can occur, for example, in a context in which volatile memory 395 contains an indication 2108 of such completion that task implementation module 1136 includes in wireless signal 454 and in which task implementation module 1136 comprises event/condition detection unit 400. Alternatively or additionally, task implementation module 1136 may be configured to generate an indication 2108 of such completion (in response to one or more of photographs 553, 554 or GPS data 1242 or timing data 1243 documenting a completed delivery task, e.g.) for inclusion in wireless signal 454.

With reference now to flow 48 of FIG. 48 and to other flows 15-19, 38-44, and 47 described above, in some variants, intensive operation 4815 described below may (optionally) be performed in conjunction with one or more intensive operations described above. Alternatively or additionally, one or more extensive operations 4894, 4897, 4898 described below may likewise comprise or be performed in conjunction with one or more extensive operations described above.

Intensive operation 4815 describes transmitting a wireless signal indicative of a delivery of a package to a device associated with a recipient of the package, the wireless signal indicating at least one of the first unmanned aerial device or the package or a sender of the package (e.g. data delivery module 154 transmitting a wireless signal 451 indicative of a delivery of a package 2050 into a vicinity of an article 1400 associated with a purchaser of the package 2050, the wireless signal 451 indicating at least one of the 1st UAD 1005 or the package 2050 or a sender 510 of the package 2050). This can occur, for example, in a context in which primary unit 3610 resides in the "first" UAD 1005 or in another device 1010 described herein; in which the "vicinity" comprises the room in which article 1400 is situated; in which task implementation module 1481 transmits various operating parameters 2126-2128 (specified by a UAD user 226 or package sender 510, e.g.) relating to such delivery. One such sequence 2121, for example, may (optionally) comprise an alias 823 or other expression 2122 facilitating an identification of article 1400. Another such expression 2122 may comprise global positioning system (GPS) or other destination coordinates 605, 606 (of the article 1400, e.g. or of an alternative destination to be used if the "first" UAD 1005 cannot locate the article 1400, e.g.). Other such parameters may comprise one or more distances 2171-2175; directions 2186-2189; protocol identifiers, or other such indications 2101-2109 described herein.

In light of teachings herein, numerous existing techniques may be applied for configuring special-purpose circuitry or other structures effective for specifying how a delivery is to be performed without undue experimentation or for configuring other decisions and devices as described herein. See, e.g., U.S. Pat. No. 8,156,542 ("Conditional data delivery to remote devices"); U.S. Pat. No. 8,112,475 ("Managing data delivery based on device state"); U.S. Pat. No. 8,090,826 ("Scheduling data delivery to manage device resources"); U.S. Pat. No. 7,647,230 ("Method and apparatus for tracking a special service delivery of a mail item created by an office worker"); U.S. Pat. No. 7,587,369 ("Trusted and secure techniques, systems and methods for item delivery and execution"); U.S. Pat. No. 7,401,030 ("Method and system for tracking disposition status of an item to be delivered within an organization"); U.S. Pat. No. 7,225,983 ("Intelligent parcel monitoring and controlling apparatus and method and terminal for executing real-time parcel pickup and delivery and operation method thereof"); U.S. Pat. No. 7,143,937 ("Systems and methods for utilizing a tracking label in an item delivery system"); U.S. Pat. No. 6,463,354 ("System and method for automatic notification of upcoming delivery of mail item").

Extensive operation 4894 describes signaling a decision whether or not to reserve a space for a passenger vehicle (e.g. resource reservation module 1156 transmitting a trigger 2118 that is effective to allocate parking space 648 for the use of car 602). This can occur, for example, in a context in which the trigger 2118 includes an affirmative decision 2133 (to reserve parking space 648, e.g.) that has been received from a person (user 626, e.g.) aboard the passenger vehicle; in which secondary unit 3750 resides in UAD 601 or in a stationary unit (at station 520, e.g.) operable to communicate with UAD 601 and in which resource reservation module 1156 maintains one or more records 964 indicating available and unavailable parking spaces (in the same parking lot, e.g.) monitored by UAD 601. In some contexts, moreover, UAD 601 may (optionally) perform operation 4894 by hovering or landing in parking space 648 to notify passersby that the space is taken.

In light of teachings herein, numerous existing techniques may be applied for configuring special-purpose circuitry or other structures effective for associating a thing or person with another thing or person without undue experimentation or for configuring other decisions and devices as described herein. See, e.g., U.S. Pat. No. 8,196,809 ("System and method for associating an absorbent article with a user"); U.S. Pat. No. 8,180,827 ("Method and apparatus for associating graphic icon in internet virtual world with user's experience in real world"); U.S. Pat. No. 8,160,615 ("Method and system for generating associations between a user profile and wireless devices"); U.S. Pat. No. 8,131,745 ("Associating user identities with different unique identifiers"); U.S. Pat. No. 8,051,429 ("Method for associating data bearing objects with user interface objects"); U.S. Pat. No. 8,006,194 ("Associating an object with a relevant data source"); U.S. Pat. No. 7,979,585 ("System and method to associate a private user identity with a public user identity"); U.S. Pat. No. 7,941,505 ("System and method for associating a user with a user profile in a computer network environment"); U.S. Pat. No. 7,787,870 ("Method and system for associating a user profile to a caller identifier").

Extensive operation 4897 describes signaling a decision whether or not to reserve a specific resource by associating the specific resource with a specific device or with a specific person (e.g. resource reservation module 157 transmitting one or more triggers 2113, 2120 effective for implementing or broadcasting an association of a sender 510 or device 775 with person 725). This can occur, for example, in a context in which network 190 comprises one or more systems 4-9 and media 1200, 2100, 4500 as described herein; in which trigger 2113 includes one expression 2122 for the specific resource (sender 510 or device 775, e.g.) and another expression 2122 for the specific entity (device or person, e.g.) with which the specific resource is or will be associated. Alternatively or additionally, in some implementations, resource reservation module 1157 may perform operation 4897 by transmitting an indication 2103 that a specific resource (a modular data handling unit 2078, e.g.) not be reserved for a specific entity (UAD 201, e.g.) by associating the specific resource with another specific entity (UAD 202, e.g.). This can occur, for example, in a context in which the specific resource can only be associated with one such entity.

In light of teachings herein, numerous existing techniques may be applied for configuring special-purpose circuitry or other structures effective for allocating resources without undue experimentation or for configuring other decisions and devices as described herein. See, e.g., U.S. Pat. No. 8,204,770 ("Computer-implemented systems and methods for resource allocation"); U.S. Pat. No. 8,200,583 ("Method and system for leasing or purchasing domain names"); U.S. Pat. No. 8,099,339 ("Systems and methods for pharmacy inventory management"); U.S. Pat. No. 7,979,309 ("Method and system for automating inventory management of consumer items"); U.S. Pat. No. 7,956,769 ("Method and system for reservation-based parking"); U.S. Pat. No. 7,941,354 ("Method and system for lease of assets, such as trailers, storage devices and facilities"); U.S. Pat. No. 7,865,409 ("Vehicle inventory management system and method"); U.S. Pat. No. 7,839,526 ("Reservation of secondary printing devices in a substitute printing system"); U.S. Pat. No. 7,836,186 ("Automated adjustment of IP address lease time based on usage"); U.S. Pat. No. 7,797,077 ("System and method for managing vending inventory"); U.S. Pat. No. 7,680,691 ("Inventory management system using RFID"); U.S. Pat. No. 7,636,687 ("Method and system for completing a lease for real property in an on-line computing environment"); U.S. Pat. No. 7,636,669 ("Recreational outing reservation system").

Extensive operation 4898 describes responding to an indication of the first unmanned aerial device becoming within a proximity of a mobile device (e.g. proximity detection module 1153 determining whether UAD 1005 has come into a vicinity 4655 of an earpiece 4661, wristband 4663, or other article 1400 wearable by a person). This can occur, for example, in a context in which such an article 1400 (comprising device 775, e.g.) is worn by a person 725 who is moving (toward or away from UAD 1005, e.g.); in which proximity detection module 1153 resides within the (wearable or other mobile) device 775 or within the "first" UAD 1005; in which one or more components of such device are thereby able to detect a proximity of the other device; and in which proximity detection module 1153 responds by invoking one or more task implementation modules 1130-1139, 1481-1486 described herein.

A first device may "become within" a proximity of a second device by one or both such devices moving toward the other. Each proximity detection module 1153 may, in some instances, operate by having a sensor as a component of a first device that detects the other device becoming close enough to the sensor to be detected by the sensor, irrespective of which device(s) moved. Alternatively or additionally, some implementations of proximity detection module 1153 may reside remotely from both devices and may be configured to determine the devices' mutual proximity from their respective coordinates 605, 606. In some contexts, for example, a proximity of an object may comprise a room (of a patient in a hospital, e.g.) containing the object. In others, a proximity (of target 1360, e.g.) may comprise only an immediate vicinity 1371 (within a few centimeters, e.g.) of the object or may comprise an entire surface (desktop 1372, e.g.) on which such an object is positioned.

In light of teachings herein, numerous existing techniques may be applied for configuring special-purpose circuitry or other structures effective for computing a difference between locations without undue experimentation or for configuring other decisions and devices as described herein. See, e.g., U.S. Pat. No. 8,044,798 ("Passive microwave speed and intrusion detection system"); U.S. Pat. No. 8,026,850 ("Apparatus and method for computing location of a moving beacon using time difference of arrival and multi-frequencies"); U.S. Pat. No. 7,962,283 ("Deviation-correction system for positioning of moving objects and motion tracking method thereof"); U.S. Pat. No. 7,778,792 ("Systems and methods for location, motion, and contact detection and tracking in a networked audiovisual device"); U.S. Pat. No. 7,775,329 ("Method and detection system for monitoring the speed of an elevator car"); U.S. Pat. No. 7,671,795 ("Wireless communications device with global positioning based on received motion data and method for use therewith"); U.S. Pat. No. 7,647,049 ("Detection of high velocity movement in a telecommunication system"); U.S. Pat. No. 7,460,052 ("Multiple frequency through-the-wall motion detection and ranging using a difference-based estimation technique"); U.S. Pat. No. 7,242,462 ("Speed detection methods and devices"); U.S. Pat. No. 6,985,206 ("Baseball pitch speed measurement and strike zone detection devices"); U.S. Pat. No. 6,400,304 ("Integrated GPS radar speed detection system").

In light of teachings herein, numerous existing techniques may be applied for configuring special-purpose circuitry or other structures effective for detecting whether two devices are near one another without undue experimentation or for configuring other decisions and devices as described herein. See, e.g., U.S. Pat. No. 8,078,107 ("Automatic network and device configuration for handheld devices based on bluetooth device proximity"); U.S. Pat. No. 8,050,243 ("Method and system for evaluating proximity to a WLAN for a UMA/GAN compatible electronic device"); U.S. Pat. No. 8,019,283 ("Automatic data encryption and access control based on Bluetooth device proximity"); U.S. Pat. No. 7,769,984 ("Dual-issuance of microprocessor instructions using dual dependency matrices"); U.S. Pat. No. 7,574,077 ("Optical imaging device for optical proximity communication"); U.S. Pat. No. 7,289,184 ("Liquid crystal panel and equipment comprising said liquid crystal panel"); U.S. Pat. No. 7,010,098 ("Ultrasonic proximity detector for a telephone device"); U.S. Pat. No. 6,735,444 ("Method and system for locating a device using a local wireless link"); U.S. Pat. No. 6,114,950 ("Obstacle proximity warning device for vehicles").

With reference now to flow 49 of FIG. 49 and to other flows 15-19, 38-44, 47, 48 described above, in some variants, one or more intensive operations 4911, 4913, 4917 described below may (optionally) be performed in conjunction with one or more intensive operations described above. Alternatively or additionally, one or more extensive operations 4992, 4999 described below may likewise comprise or be performed in conjunction with one or more extensive operations described above.

Intensive operation 4911 describes presenting navigation guidance via a display aboard the first unmanned aerial device while a primary motor of the first unmanned aerial device is not moving the first unmanned aerial device (e.g. triggering interface control module 1111 to output navigation guidance 2130 via a touchscreen or other display 1172 borne by UAD 1005 after controller 1085 stops motor 1081). This can occur, for example, in a context in which UAD 1005 includes a secondary unit 3750 that includes one or more media 2110 and in which controller 1085 switches motor 1081 off. Alternatively or additionally, task implementation module 1131 may perform operation 4911 by displaying guidance 2130 (arrows, words, or other turn-by-turn navigation instructions for a pedestrian or motor vehicle, e.g.). In some variants, for example, such guidance 2130 may be outputted locally (to a user 226 via a speaker 1171 or display 1172, 2072 aboard UAD 1005, e.g.) while UAD 1005 is stationary (tethered or hovering or landed, e.g.). Alternatively or additionally, in some variants, such task implementation modules 1131, 1132 may be disabled selectively by a signal from controller 1085 (a control signal indicating that motor 1081 is active, e.g.).

In light of teachings herein, numerous existing techniques may be applied for configuring special-purpose circuitry or other structures effective for providing navigational guidance without undue experimentation or for configuring other decisions and devices as described herein. See, e.g., U.S. Pat. No. 8,179,287 ("Method and apparatus for communicating map and route guidance information for vehicle navigation"); U.S. Pat. No. 8,170,798 ("Navigation system and operation guidance display method for use in this navigation system"); U.S. Pat. No. 8,155,805 ("Flight guidance and navigation display for a helicopter"); U.S. Pat. No. 7,970,539 ("Method of direction-guidance using 3D sound and navigation system using the method"); U.S. Pat. No. 7,899,617 ("Navigation system providing route guidance in multi-lane road according to vehicle lane position"); U.S. Pat. No. 7,881,497 ("Vision based navigation and guidance system"); U.S. Pat. No. 7,805,306 ("Voice guidance device and navigation device with the same"); U.S. Pat. No. 6,901,330 ("Navigation system, method and device with voice guidance"); U.S. Pat. No. 6,459,935 ("Integrated filter feed-thru"); U.S. Pat. No. 6,374,182 ("Method and system for providing walking instructions with route guidance in a navigation program").

Intensive operation 4913 describes transmitting navigation guidance via a speaker of the first unmanned aerial device while a primary motor of the first unmanned aerial device is not moving the first unmanned aerial device (e.g. task implementation module 1132 triggering interface control module 1111 to output navigation guidance 2130 via a speaker 1171 borne by UAD 1005 after controller 1085 disengages motor 1081 from propeller 1071). This can occur, for example, in a context in which UAD 1005 includes a secondary unit 3750 that includes one or more media 2110 and in which controller 1085 permits UAD 1005 to idle (drift or land, e.g.) by disengaging one or more primary motors 1081, 1082 thereof from one or more props 1071, 1072 to which it/they correspond (by mechanical coupling, e.g.). In some variants, for example, such task implementation modules 1131, 1132 may be enabled (so that it is possible for the transmission to coincide with the condition recited in operation 4913, e.g.) by a signal from a sensor array 1494 positioned adjacent one or more props 1071, 1072 (indicating that they are stopped, e.g.).

Intensive operation 4917 describes identifying an operating mode of the first unmanned aerial device audibly or visibly while a primary motor of the first unmanned aerial device is not moving the first unmanned aerial device (e.g. task implementation module 1133 identifying one or more triggers 2111-2120 or operating parameters 2126-2128 relating to how UAD 701 is performing or will perform a current or scheduled task 491-499 so that a person 726 who is carrying UAD 701 can hear or see such information). This can occur, for example, in a context in which speaker 1171 can announce such information audibly (in response to a voice menu aboard UAD 701, e.g.) or in which a display 1172, 2072 aboard UAD 701 can present such information visibly, or both. This can occur, for example, in a context in which the operating mode(s) that currently apply to the UAD (silent or not, flight permitted or not, e.g.) can be a function of which of the proximate zones 781, 782 currently contain UAD 701.

In light of teachings herein, numerous existing techniques may be applied for configuring special-purpose circuitry or other structures effective for reporting current or scheduled operating parameters without undue experimentation or for configuring other decisions and devices as described herein. See, e.g., U.S. Pat. No. 8,203,426 ("Feed protocol used to report status and event information in physical access control system"); U.S. Pat. No. 8,171,318 ("Reporting flash memory operating voltages"); U.S. Pat. No. 8,121,083 ("Method and device for reporting request for uplink scheduling or emergency in wireless network"); U.S. Pat. No. 8,024,138 ("Power supply circuitry, collection and reporting of power supply parameter information"); U.S. Pat. No. 8,014,974 ("System and method for analyzing and reporting machine operating parameters"); U.S. Pat. No. 7,983,759 ("Advanced patient management for reporting multiple health-related parameters"); U.S. Pat. No. 7,756,822 ("Operational reporting architecture"); U.S. Pat. No. 7,245,702 ("Method and apparatus for determining and reporting the operational status of an integrated services hub").

Extensive operation 4992 describes causing a modular observation unit to be lifted and activated within at most about an hour of the modular observation unit becoming part of the first unmanned aerial device (e.g. an interface control module 1114, motion control module 1158, device activation module 1472, and an engagement structure 2030 of UAD 1005 jointly picking up cargo module 2090 and then activating a data handling unit 2078 thereof). This can occur, for example, in a context in which engagement structure 2030 (one or more robotic arms 2039, e.g.) comprise a mechanical linkage 2040 between cargo module 2090 and the remainder of UAD 1005; in which interface control module 1114 transmits one trigger 2115 causing motion control module 1158 to engage one or more motors 1081, 1082 to rotate props 1071, 1072 so that UAD 1005 takes off; and in which interface control module 1114 transmits another trigger 2116 causing device activation module 1472 to acquire image data 1241 by activating a camera 2071 of data handling unit 2078. In some variants, for example, trigger 2116 may be configured to actuate post 2006 (sliding it along shaft 2025 rightward, as shown, into recess 2023, e.g.) so that post 2006 engages and supports a modular observation unit (a package 2050 containing a sensor array 1494, e.g.). This can occur in a context in which motion control module 1158 positions UAD 1005 so that a topmost portion of package 2050 extends up into groove 2026, for example. In other contexts, a user may (optionally) position structure 2030 (relative to package 2050, e.g.) or may otherwise facilitate linkage 2040. Alternatively or additionally, in some variants, the modular observation unit (a camera 2071 or GPS 1063 in cargo module 2090, e.g.) may be lifted (by engagement structure 2030, e.g.) responsive to an indication of the modular observation unit becoming part of the first unmanned aerial device (a control signal activating engagement structure 2030 or a sensor signal indicating an activation of engagement structure 2030, e.g.) or to the modular observation unit being activated. In some variants, moreover, the modular observation unit may be activated (by device activation module 1472, e.g.) responsive to an indication of the modular observation unit becoming part of the first unmanned aerial device (a control signal activating engagement structure 2030 or a sensor signal indicating an activation of engagement structure 2030, e.g.) or to the modular observation unit being lifted. In a context in which UAD 1005 implements UAD 501, moreover, such a user may generate one or more triggers 2111-2120 as described herein (trigger 2116 causing device activation module 1472 to acquire sensor data, e.g.) by pressing a button 561 (positioned on a cargo module 2090 of UAD 1005, e.g.).

In light of teachings herein, numerous existing techniques may be applied for configuring special-purpose circuitry or other structures effective for aerial motion control without undue experimentation or for configuring other decisions and devices as described herein. See, e.g., U.S. Pat. No. 7,962,254 ("Method and system for assisting flight control of a low-flying aircraft"); U.S. Pat. No. 7,931,238 ("Automatic velocity control system for aircraft"); U.S. Pat. No. 7,837,143 ("Method and apparatus for disabling pilot control of a hijacked aircraft"); U.S. Pat. No. 7,806,371 ("Remote control model aircraft with laser tag shooting action"); U.S. Pat. No. 7,787,998 ("Method and device for assisting the lateral control of an aircraft running on a runway"); U.S. Pat. No. 7,669,805 ("Device for remotely controlling aircraft control surfaces"); U.S. Pat. No. 7,617,024 ("Automatic heading control system for tiltrotor aircraft and helicopters"); U.S. Pat. No. 7,262,730 ("Method and a station for assisting the control of an aircraft"); U.S. Pat. No. 6,991,304 ("Method and device for automatic control of an aircraft deceleration in running phase"); U.S. Pat. No. 6,917,863 ("System for assuming and maintaining secure remote control of an aircraft").

Extensive operation 4999 describes signaling a decision whether or not to configure the first unmanned aerial device to continue observing a first person responsive to a prior observation of the first person (e.g. task implementation module 1134 responding to a behavioral indication 2102 from pattern recognition module 1422 by generating a positive or negative decision 2132 about whether to transmit a trigger 2117 instructing UAD 801 to continue one or more tasks 492, 493 that include observing person 727). This can occur, for example, in a context in which a portable article 1400 (UAD 701, e.g.) comprising secondary unit 3750 is positioned so that it can observe person 727 (sensing his speech or movements, e.g.); in which an initial task 492 comprises UAD 802 providing image data 1241 or other sensor data (comprising the prior observation, e.g.) to pattern recognition module 1422 for analysis; in which pattern recognition module 1422 comprises one or more of a gesture detection module 1402 or a spoken expression detection module 1403 or an optical condition detection module; and in which a positive behavioral indication 2102 results from one or more recognizable events 1412-1415 being detected. In some contexts, task implementation module 1134 may be configured so that decision 2132 will generally be negative (contraindicative of monitoring, e.g.) if the behavioral indication 2102 is normal (within expected bounds, e.g.), for example, and will otherwise generally be positive. In some variants, moreover, pattern recognition module 1422 may be configured to detect events (a key press input detection event 1415, e.g.) relating to person 727 from other UAD's or systems described herein (a keyboard 1391 or other input 121 of a stationary primary unit 3610, e.g.). Alternatively or additionally, in some contexts, pattern recognition module 1422 may be configured to transmit a positive or negative behavioral indication 2102 resulting from some other event (a timer expiration, e.g.) occurring before any of such recognizable events (recognizable by whichever event/condition detection logic 1410 is active, e.g.) are detected.

Alternatively or additionally, task implementation module 1134 may be configured to perform operation 4999 by responding to one or more attribute indications 2101 (relating to identity, shape, preference, or other such static attributes, e.g.) of a subject of observation (an item recipient 4650 or other person described herein, e.g.). Task implementation module 1134 may thus be configured to implement a continued observation of such a subject via a "first" UAD 801 in response to any combination of (1) one or more indications 2104 that the subject's face 4665 or clothing 728 resembles that of a particular person of interest, (2) one or more indications 2105 that the subject has spoken or otherwise used particular terminology of interest (a threat or classified program name, e.g.), or (3) one or more indications 2106 that the subject has taken a recognizable action of interest (fired a gun or entered an office 1380, e.g.). Such recognizable indications 2104-2106 may be based on the "prior observations" from the "first" UAD 801, from another UAD 802, from another device, or from some combination of these. In some contexts, for example, such indications 2104-2106 from two or more such devices may be correlated or otherwise aggregated (by selective retention module 159, e.g.) according to status-indicative data (image data 1241, GPS data 1242, or timing data 1243 indicative of performance, e.g.) from each respective device.

In light of teachings herein, numerous existing techniques may be applied for configuring special-purpose circuitry or other structures effective for detecting a particular person or event without undue experimentation or for configuring other decisions and devices as described herein. See, e.g., U.S. Pat. No. 8,184,914 ("Method and system of person identification by facial image"); U.S. Pat. No. 8,170,532 ("Method and system for identification using a portable wireless communication device of a person"); U.S. Pat. No. 8,144,881 ("Audio gain control using specific-loudness-based auditory event detection"); U.S. Pat. No. 8,109,891 ("Device and method for detecting an epileptic event"); U.S. Pat. No. 8,040,245 ("Hand washing monitor for detecting the entry and identification of a person"); U.S. Pat. No. 8,036,891 ("Methods of identification using voice sound analysis"); U.S. Pat. No. 7,995,731 ("Tag interrogator and microphone array for identifying a person speaking in a room"); U.S. Pat. No. 7,774,719 ("System and method for conducting online visual identification of a person"); U.S. Pat. No. 7,653,697 ("System, method and apparatus for communicating via sound messages and personal sound identifiers"); U.S. Pat. No. 7,596,248 ("Method for identification of person by recognition of a digital fingerprint"); U.S. Pat. No. 7,596,241 ("System and method for automatic person counting and detection of specific events"); U.S. Pat. No. 7,492,926 ("Method for identifying a person from a detected eye image").

With reference now to flow 50 of FIG. 50 and to other flows 15-19, 38-44, 47-49 described above, in some variants, one or more intensive operations 5011, 5016, 5017 described below may (optionally) be performed in conjunction with one or more intensive operations described above. Alternatively or additionally, one or more extensive operations 5093, 5094, 5095 described below may likewise comprise or be performed in conjunction with one or more extensive operations described above.

Intensive operation 5011 describes causing another unmanned aerial device to capture delivery data relating to the first unmanned aerial device (e.g. device activation module 1471 transmitting one or more requests 373, invitations 374, or other triggers 4584 that result in UAD 803 acquiring observations of UAD 801 completing a delivery). Referring to FIG. 8, for example, this can occur in a context in which a tracking control module 149 aboard UAD 803 receives a task description 1252 specifying what audio clips 563, photographs 553, 554 or other records may constitute acceptable delivery data 4553 and in which device activation module 1471 resides in UAD 801 (as the "first" UAD, e.g.) or in a stationary control unit 860 in wireless communication with UAD 803. Alternatively or additionally, device activation module 1471 may perform operation 5011 by configuring another UAD (an instance of UAD 1005, e.g.) to indicate an observed result 4523 (a location or other indicator of incremental success, e.g.) of one or more other tasks 491-499 (incorporating a delivery component, e.g.) being undertaken by a "first" UAD described herein.

In light of teachings herein, numerous existing techniques may be applied for configuring special-purpose circuitry or other structures effective for programmatic image capture or other event tracking without undue experimentation or for configuring other decisions and devices as described herein. See, e.g., U.S. Pat. No. 8,149,288 ("Image capture device that records image accordant with predetermined condition and storage medium that stores program"); U.S. Pat. No. 8,004,563 ("Method and system for effectively performing event detection using feature streams of image sequences"); U.S. Pat. No. 7,643,686 ("Multi-tiered image clustering by event"); U.S. Pat. No. 7,476,796 ("Image controlling apparatus capable of controlling reproduction of image data in accordance with event"); U.S. Pat. No. 6,721,640 ("Event based aircraft image and data recording system"); U.S. Pat. No. 6,167,186 ("Video recording device for retroactively reproducing a video image of an event, while also recording images in real time").

Intensive operation 5016 describes configuring the first unmanned aerial device not to be equipped with any light sensors (e.g. device configuration module 1475 transmitting a trigger 2119 that causes a robotic arm 2039 affixed to UAD 1005 to release an optical sensor aboard UAD 1005). This can occur, for example, in a context in which cargo module 2090 implements an instance of article 1400 that includes a charge-coupled device 1493 or other sensor array 1494 comprising optical sensors; in which another instance of article 1400 transmits trigger 2119 to robotic arm 2039; in which UAD 1005 implements at least one UAD 801-3 that is capable of navigating to a healthcare or item recipient 4650 or other destination 530 without any need for an onboard camera 2071 or CCD 1493; and in which a user can readily discern which cargo module 2090 (if any) is being carried by UAD 1005. In some contexts, for example, an inspection of UAD 1005 would not otherwise provide a user (recipient 4650, e.g.) with an adequate assurance of privacy.

Alternatively or additionally, operation 5016 may be performed by an instance of device configuration module 1475 that manufactures UAD 1005 (at a factory, e.g.) as a "blind" device (i.e. lacking light sensors). This can occur, for example, in a context in which "first" UAD 1005 implements UAD 801 (of FIG. 8) and in which device configuration module 1475 implements non-optical position sensing (sonar, e.g.) or optical position sensing via optical sensors not borne by UAD 1005 (in a stationary control unit 860 or aboard a second UAD 802, e.g.).

Intensive operation 5017 describes causing a data handling device aboard the first unmanned aerial device to contain a task schedule indicating a first future delivery of a first object to a first destination and a second future delivery of a second object to a second destination (e.g. task implementation module 1134 causing a memory 395 or disk drive 1495 aboard the UAD 1005 to contain several tasks 491-494, 1211-1214 comprising the first future delivery and the second future delivery). This can occur, for example, in a context in which task 491 associates (by inclusion in a single common table entry 1225, e.g.) a task identifier 1221 with one or more of a description of the "first" destination (an immediate vicinity 1371 of target 1360, e.g.) or a description of the "first" object (an inhaler 2062, e.g.) or other specifications 1223 (tracking mode, e.g.) pertaining to the first future delivery; in which task 494 associates another task identifier 1221 with one or more of a description of the "second" destination 530 or a description of the "second" object (a rescued second UAD 202, e.g.) or other specifications 1223 (aborting the delivery if anyone is present, e.g.) pertaining to the second future delivery.

In light of teachings herein, numerous existing techniques may be applied for configuring special-purpose circuitry or other structures effective for scheduling deliveries without undue experimentation or for configuring other decisions and devices as described herein. See, e.g., U.S. Pat. No. 8,090,826 ("Scheduling data delivery to manage device resources"); U.S. Pat. No. 7,929,559 ("Method of scheduling message delivery in a wireless communication system"); U.S. Pat. No. 7,516,082 ("Scheduling delivery of chemical products based on a predicted estimated time of exhaustion"); U.S. Pat. No. 7,437,305 ("Scheduling delivery of products via the internet"); U.S. Pat. No. 7,233,907 ("Parcel or service delivery with partially scheduled time windows"); U.S. Pat. No. 7,174,305 ("Method and system for scheduling online targeted content delivery"); U.S. Pat. No. 6,985,871 ("Systems and methods for scheduling reoccurring deliveries and pickups"); U.S. Pat. No. 6,826,534 ("Agent and method for dynamically scheduling publication in an automated document delivery system"); U.S. Pat. No. 6,238,290 ("System and method for scheduled delivery of a software program over a cable network"); U.S. Pat. No. 6,009,409 ("System and method for scheduling and controlling delivery of advertising in a communications network").

Extensive operation 5093 describes causing the first unmanned aerial device to execute a delivery of a single dose of a therapeutic material to a human hand within one minute of an image capture of a portion of the human hand (e.g. task implementation module 1484 causing UAD 501 to complete a delivery of a single syringe 556 directly into a hand 4664 of a healthcare recipient 4650 or caregiver). This can occur, for example in a context in which such delivery occurs within a minute before or after a camera 4636 captures one or more images (photograph 554, e.g.) depicting a palm, finger, or other feature of the hand 4664 distinctive enough to prove the delivery recipient's identity; in which such image(s) also depict the syringe 2061 or other dose clearly enough to prove the delivery occurred; in which the "first" UAD carries at most one (nominal) dose of the therapeutic material at any given time; in which the therapeutic material is highly addictive and expensive; and in which an installed dispenser or other device configured to administer more than one dose would be vulnerable to break-ins or other abuse. Alternatively, in some contexts, the only bioactive material borne by UAD 1005 (implementing UAD 501, e.g.) is the single dose 2064 in a capsule 2063.

In some embodiments, a process step occurs "within" a time interval of an event if the event occurs before or after the process step by an amount of time that does not exceed the time interval. A device or other module that is configured to perform an action "within" a time interval may include a timer 1141 or other circuitry configured to ensure such performance. In fact a module may be "configured to" perform a brief action (of 1-2 seconds, e.g.) within a long interval (of 1-2 minutes, e.g.), even if the interval is not signaled, in some contexts (in which the performance occurs during a portion of the interval in which the process step is enabled, e.g.).

In some embodiments, a device is "configured to execute" a task if special-purpose hardware or software aboard the device enables the UAD to actually complete the task. Likewise a UAD is "configured to execute" a task if such components aboard the UAD will enable the UAD to complete the task autonomously provided that no overriding instructions ("abort," e.g.) or other intervening events or conditions (blockages, e.g.) prevent such completion. A component is "aboard" a UAD if it resides in or on the UAD or is mechanically supported by the UAD (hanging from the UAD by a tether or otherwise affixed to the UAD, e.g.).

In light of teachings herein, numerous existing techniques may be applied for configuring special-purpose circuitry or other structures effective for automatic positioning without undue experimentation or for configuring other decisions and devices as described herein. See, e.g., U.S. Pat. No. 8,108,091 ("Automatic position-based guide toy vehicle apparatus"); U.S. Pat. No. 8,027,761 ("Local positioning system for automated lawn mowers"); U.S. Pat. No. 7,869,562 ("Automatic patient positioning system"); U.S. Pat. No. 7,693,565 ("Method and apparatus for automatically positioning a structure within a field of view"); U.S. Pat. No. 7,502,684 ("Method and system for the automatic piloting of an aircraft on the approach to an airdrop position"); U.S. Pat. No. 6,942,369 ("Device for the automatic adjustment of the position of the headlights on a motor vehicle"); U.S. Pat. No. 6,931,596 ("Automatic positioning of display depending upon the viewer's location").

Extensive operation 5094 describes configuring the first unmanned aerial device to execute a delivery of a particular material to a vicinity of a portable device within one minute of an image capture of the vicinity of the portable device (e.g. task implementation module 1482 responding to a photographic image 2161 depicting a position 1463 right above a cup 1464 of coffee by transmitting a trigger 2112 to one or more dispensers 2038 of UAD 1005, which respond by delivering cream or sugar into the cup 1464). This can occur, for example, in a context in which task implementation module 1482 previously transmitted a trigger 2111 commanding one or more flight control modules 151, 152 to guide UAD 1005 approximately to position 1463; in which camera 2071 comprises a cargo module 2090 carried by a robotic arm 2039 or other support structure 2030 of UAD 1005; and in which camera 2071 captures a video clip 2153 comprising a succession of images 2161, 2162 depicting a top view of cup 1464 via which an optical condition detection module 1404 may effectively control the alignment of the one or more dispensers 2038 relative to cup 1464. In some contexts, for example, other preparations (verifying a user preference, e.g.) may occur before the delivery is completed (during the "one minute," e.g.). Alternatively or additionally, in some variants, such an image 2161 (suitable for verifying alignment, e.g.) may be obtained via a charge-coupled device 1493 (aboard UAD 1005 or another UAD tasked with observation, e.g.) or via a stationary-mount surveillance camera 936 (mounted on a building 935 or other stationary object, e.g.).

In light of teachings herein, numerous existing techniques may be applied for configuring special-purpose circuitry or other structures effective for delivering an item to a vicinity of a device without undue experimentation or for configuring other decisions and devices as described herein. See, e.g., U.S. Pat. No. 8,167,786 ("Systems and methods for delivering a medical implant to an anatomical location in a patient"); U.S. Pat. No. 7,822,463 ("Method for delivering a device to a target location"); U.S. Pat. No. 7,735,631 ("Mail processing system and method of delivering articles to delivery locations therein"); U.S. Pat. No. 7,670,329 ("Systems and methods for delivering drugs to selected locations within the body"); U.S. Pat. No. 7,658,156 ("Apparatus and method for delivering beneficial agents to subterranean locations"); U.S. Pat. No. 7,361,183 ("Locator and delivery device and method of use"); U.S. Pat. No. 6,711,555 ("Method and apparatus for delivering mail items to non-postal route locations").

Extensive operation 5095 describes causing the first unmanned aerial device to execute a delivery of a particular object to a human recipient contemporaneously with an image capture of a portion of the human recipient (e.g. task implementation module 1483 transmitting one or more triggers 2110, 2116 that configure UAD 1005 to deliver the object to recipient 4650 within about ten seconds of when a camera 2071, 4636 captures an image 2164 of a hand 4664 or face 4665 of the recipient 4650). This can occur, for example, in a context in which the object comprises a passive radio frequency identification (RFID) chip 1461, an envelope 551 or other package 2050 (containing an inhaler 2062 or other therapeutic product 2060, e.g.), a data handling unit 2078 (a memory 395 or other medium, e.g.), a battery 2085 or other power source, a wearable article (earpiece 4661 or wristband 4663, e.g.), a "second" UAD, or similar physical objects. In some variants, for example, such image capture occurs in response to one or more triggers from task implementation module 1483.

In light of teachings herein, numerous existing techniques may be applied for configuring special-purpose circuitry or other structures effective for determining how one or more portions of a person's body are positioned without undue experimentation or for configuring other decisions and devices as described herein. See, e.g., U.S. Pat. No. 7,978,084 ("Body position monitoring system"); U.S. Pat. No. 7,949,089 ("Apparatus and method for tracking feature's position in human body"); U.S. Pat. No. 7,934,267 ("Articles of apparel providing enhanced body position feedback"); U.S. Pat. No. 7,916,066 ("Method and apparatus for a body position monitor and fall detector using radar"); U.S. Pat. No. 7,889,913 ("Automatic compositing of 3D objects in a still frame or series of frames"); U.S. Pat. No. 7,630,806 ("System and method for detecting and protecting pedestrians"); U.S. Pat. No. 7,029,031 ("Method and device for detecting the position and the posture of a human body"); U.S. Pat. No. 6,692,449 ("Methods and system for assessing limb position sense during movement").

With reference now to flow 51 of FIG. 51 and to other flows 15-19, 38-44, 47-50 described above, in some variants, one or more intensive operations 5112, 5119 described below may (optionally) be performed in conjunction with one or more intensive operations described above. Alternatively or additionally, one or more extensive operations 5195, 5196 described below may likewise comprise or be performed in conjunction with one or more extensive operations described above.

Intensive operation 5112 describes determining whether or not an operator of the first unmanned aerial device has indicated a tracking mode of the first unmanned aerial device (e.g. interface control module 1110 determining whether any specifications 1223 provided by a user 226 of UAD 1005 contain any indication 2109 of whether or how any ongoing or future task 491-499, 1211-1214 assigned to UAD 1005 should be tracked). This can occur, for example, in a context in which user 226 indicates via input 391 (a mouse or keyboard 1391, e.g.) a decision 2131 that a default tracking mode 361 for UAD 1005 (for use in tasks not specifying an exception, e.g.) should be "none" (not record any aspect of tasks performed by UAD 1005, e.g.). Alternatively or additionally, such decisions 2131 or specifications 1223 may indicate "periodic" tracking (recording image data 1241, GPS data 1242, wind speed, or other status-indicative data 1240 relating to UAD 1005 periodically, e.g.) with operating parameter 2127 specifying the tracking period (how long to wait between successive recording events, e.g.) and operating parameter 2128 specifying the source of data to be recorded (event/condition detection logic 1410 or camera 2071, e.g.).

In light of teachings herein, numerous existing techniques may be applied for configuring special-purpose circuitry or other structures effective for task performance monitoring without undue experimentation or for configuring other decisions and devices as described herein. See, e.g., U.S. Pat. No. 8,171,474 ("System and method for managing, scheduling, controlling and monitoring execution of jobs by a job scheduler utilizing a publish/subscription interface"); U.S. Pat. No. 8,164,461 ("Monitoring task performance"); U.S. Pat. No. 7,996,658 ("Processor system and method for monitoring performance of a selected task among a plurality of tasks"); U.S. Pat. No. 7,953,806 ("Task assignment and progress monitoring in an instant messaging session"); U.S. Pat. No. 7,784,946 ("Virtual microscope system for monitoring the progress of corneal ablative surgery and associated methods"); U.S. Pat. No. 7,764,179 ("Method of an apparatus for monitoring the processing cycle of a job and instructing workers to perform events or steps according to a standard"); U.S. Pat. No. 7,610,213 ("Apparatus and method for monitoring progress of customer generated trouble tickets"); U.S. Pat. No. 7,494,464 ("Monitoring system for monitoring the progress of neurological diseases"); U.S. Pat. No. 7,331,019 ("System and method for real-time configurable monitoring and management of task performance systems"); U.S. Pat. No. 6,669,653 ("Method and apparatus for monitoring the progress of labor"); U.S. Pat. No. 6,569,690 ("Monitoring system for determining progress in a fabrication activity"); U.S. Pat. No. 6,034,361 ("System for monitoring the progress of a chemical reaction in a microwave-assisted heating system"); U.S. Pat. No. 6,033,316 ("Golf course progress monitor to alleviate slow play").

Intensive operation 5119 describes overriding a first task being performed by the first unmanned aerial device by transmitting a wireless signal indicative of a second task to the first unmanned aerial device (e.g. task implementation module 1139 transmitting a wireless signal 2192 indicative of a pickup task 1213 and a delivery task 1214 to an interface control module 142 of a UAD 1005 that is performing a lower-priority task 1211). This can occur, for example, in a context in which interface control module 142 includes a task scheduler 1220 indicating one or more ongoing, contingent, upcoming, or other tasks 1211-1214; in which task scheduler 1220 earlier received (from one or more task implementation modules 1130-1139, e.g.) another signal 2191 indicative of the lower-priority task 1211; and in which scalar values 1222 control the respective rankings of the scheduled tasks 1211-1214 so that an intermediate-priority task 1212 (energy replenishment, e.g.) will be performed before "lower-priority" tasks and after "higher-priority" tasks. In other variants, however, task implementation module 1139 may be (a) configured to modify the scalar value 1222 of task 1212 (to indicate a higher priority, e.g.) responsive to an indication that one or more higher priority tasks 1213, 1214 will not be completed (due to capacity limitations, e.g.) without first executing task 1212 or (b) configured to be performed contingently (with a highest priority, but only if a particular condition (running below a fuel/charge threshold 4594 or other such conditions set forth in the task specification 1223, e.g.) is met.

In light of teachings herein, numerous existing techniques may be applied for configuring special-purpose circuitry or other structures effective for ranking tasks without undue experimentation or for configuring other decisions and devices as described herein. See, e.g., U.S. Pat. No. 8,200,491 ("Method and system for automatically detecting morphemes in a task classification system using lattices"); U.S. Pat. No. 8,185,536 ("Rank-order service providers based on desired service properties"); U.S. Pat. No. 8,135,708 ("Relevance ranked faceted metadata search engine"); U.S. Pat. No. 8,095,612 ("Ranking messages in an electronic messaging environment"); U.S. Pat. No. 8,087,019 ("Systems and methods for performing machine-implemented tasks"); U.S. Pat. No. 7,969,922 ("Apparatus and methods for providing configurable task management of a wireless device"); U.S. Pat. No. 7,945,470 ("Facilitating performance of submitted tasks by mobile task performers"); U.S. Pat. No. 7,885,222 ("Task scheduler responsive to connectivity prerequisites"); U.S. Pat. No. 8,127,300 ("Hardware based dynamic load balancing of message passing interface tasks"); U.S. Pat. No. 7,290,005 ("System for improving the performance of information retrieval-type tasks by identifying the relations of constituents").

Extensive operation 5195 describes causing the first unmanned aerial device to fly toward a home station in response to an indication of a specific person moving at least a threshold distance away from the first unmanned aerial device (e.g. sequence recognition module 1106 transmitting a trigger 423 to a controller 1085, 1095 of the "first" UAD instructing the latter to fly home in response to an outcome of protocol 418 indicating that one or more device-identifiable people 725 have moved at least a minimum distance 2174 in a direction generally away from the 1st UAD). This can occur, for example, in a context in which (at least) the navigation of UAD 1005 is locally controlled (via on-board controller 1085, e.g.); in which controller 1085 has access to protocol 418 (implemented therein as a software subroutine or in special-purpose circuitry, e.g.); in which the "first" UAD comprises a helicopter 1002 or other UAD 1005 of FIG. 10 (featuring one or more aspects of UAD's depicted above in systems 4-9, e.g.); and in which one or more kiosks 250 or other stations 520, 930 are qualifying "home stations" (identified by coordinates 606, a distinctive auditory or optical signal from a beacon 217 near such station(s), or other such expressions 2122 (in trigger 423, e.g.) useable by a flight control module 151, 152.

In one context, sequence recognition module 1106 (implementing one embodiment of protocol 418, e.g.) has been notified that entity identification module 144 has detected person 725 being "near" the first UAD—close enough that facial recognition, proximity sensors 449, or other suitable technologies described herein generate an output 1142 identifying person 725 as the "specific person" and explicitly or otherwise indicating a distance 2171 and direction 2186 of initial separation (in a 2- or 3-dimensional frame of reference, e.g.). Sequence recognition module 1106 responds to this notification by iteratively determining (each 0.1 or 1 second, e.g.) where person 725 is relative to her prior position (indicating her movement distance 2172 and direction 2187, e.g.) and by accumulating the movements (as vector-valued or scalar-valued components, e.g.) and comparing a resultant vector magnitude or other scalar distance 2173 (for at least those iterations in which person 725 moved generally away from the first UAD, e.g.) against the threshold distance 2174. (It should be noted that device 775 would be moving "generally away" from another UAD 701, situated directly to the south as shown, by moving west-northwest or north or east-northeast.) In some contexts, sequence recognition module 1106 may be configured to transmit a heading or otherwise-expressed direction 2188 (comprising trigger 423, e.g.) generally toward a (nearest or other) home station 520 relative to UAD 701's current location, whereby UAD 701 is caused to fly toward home station 520.

Alternatively or additionally, protocol 418 (implemented in a sequence recognition module 1107 within a controller 1095 remote from a "first" UAD 1005 under its control, e.g.) may make a similar determination of a UAD user 226, 626 (either being the "specific person") moving at least a threshold distance 2175 (of roughly 1 to 10 meters, within 1 or 2 orders of magnitude, e.g.) away from the first UAD as a manifestation of such user(s) being finished with or otherwise not in need of the first UAD. This can occur, for example, in a context in which "first" UAD 1005 has landed or started hovering in a locality in response to sequence recognition module 1107 receiving an indication of such user(s) being near the first UAD (from entity identification module 144 or proximity sensor 449, e.g.).

In light of teachings herein, numerous existing techniques may be applied for configuring special-purpose circuitry or other structures effective for estimating a distance or movement (of one person or object relative to another, e.g.) without undue experimentation or for configuring other decisions and devices as described herein. See, e.g., U.S. Pat. No. 7,782,365 ("Enhanced video/still image correlation"); U.S. Pat. No. 8,219,312 ("Determining speed parameters in a geographic area"); U.S. Pat. No. 8,219,116 ("Wireless base station location estimation"); U.S. Pat. No. 8,207,869 ("Position estimation for navigation devices"); U.S. Pat. No. 8,138,976 ("Method for position estimation using generalized error distributions"); U.S. Pat. No. 7,592,945 ("Method of estimating target elevation utilizing radar data fusion"); U.S. Pat. No. 7,532,896 ("Wireless node location mechanism using antenna pattern diversity to enhance accuracy of location estimates"); U.S. Pat. No. 8,068,802 ("Estimating the location of a wireless terminal based on calibrated signal-strength measurements"); U.S. Pat. No. 7,895,013 ("Estimation of the speed of a mobile device"); U.S. Pat. No. 7,720,554 ("Methods and apparatus for position estimation using reflected light sources").

Extensive operation 5196 describes responding to a determination of whether or not a received signal expresses a first name of the first unmanned aerial device and whether or not the received signal expresses a second name of the first unmanned aerial device (e.g. pattern recognition module 1423 transmitting respective results 4524, 4525 of searching a sequence 2121 of characters of an incoming signal 2194 for any instance of the "first" UAD name 1425 or any instance of the "second" UAD name 1426). This can occur, for example, in a context in which such results 4524, 4525 are each Boolean values ("positive" if found and otherwise "negative," e.g.); in which such names 1425, 1426 are aliases 822, 823 identifying UAD 802; in which control unit 860 includes storage or transmission media 2100, 4500; and in which instances of article 1400 comprise control unit 860 and reside in network 890. Alternatively or additionally, in some variants, pattern recognition module 1423 may respond to a positive search/comparison result (an indication that at least one of the UAD names was found among in signal 2194, e.g.) by programmatically and conditionally invoking one or more device activation modules 1471, 1472 or causing a transmission of one or more triggers 2111-2120 described herein.

In light of teachings herein, numerous existing techniques may be applied for configuring special-purpose circuitry or other structures effective for pattern matching without undue experimentation or for configuring other decisions and devices as described herein. See, e.g., U.S. Pat. No. 8,209, 278 ("Computer editing system for common textual patterns in legal documents"); U.S. Pat. No. 8,209,171 ("Methods and apparatus relating to searching of spoken audio data"); U.S. Pat. No. 8,171,567 ("Authentication method and system"); U.S. Pat. No. 8,023,695 ("Methods for analyzing electronic media including video and audio"); U.S. Pat. No. 7,917,514 ("Visual and multi-dimensional search"); U.S. Pat. No. 8,131,540 ("Method and system for extending keyword searching to syntactically and semantically annotated data").

Referring again to the flow embodiments of FIGS. 15 and 47-51, other variants of data acquisition module 138 may perform operation 53—obtaining first data indicating that a first unmanned aerial device delivered a first item to a first entity—by asking for, receiving, and recording (via an interface 390 or other data handling unit 2078 in a vicinity 4655 of an item recipient 4650, e.g.) a spoken confirmation 382 that the item was received. This can occur, for example, in a context in which UAD 1005 includes data handling unit 207; in which an engagement structure 2030 of UAD 1005 (post 2006 or robotic arm 2039, e.g.) releases cargo module 490 (a cell phone, e.g.) in a vicinity 4655 of recipient 4650; and in which data acquisition module 138 triggers the data handling unit 2078 to ask for and cause a recordation of a spoken confirmation 382 (as audio clip 563, for example, obtained by conducting an automated telephone call or similar verbal interchange via data handling unit 2078, e.g.) from recipient 4650. In the variants set forth above, for example, operation 53 and one or more others of the above-describe intensive operations may be initiated by processor 365 (executing a respective variant of high-level command 484, e.g.) or by invoking special-purpose circuitry as described above.

Other variants of data delivery module 153 may likewise perform operation 84 of flow 15—transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device—by transmitting (to a sender 510 of cargo module 490, e.g.) a wireless signal 2195 (via station 520 through air 585, e.g.) containing the recorded spoken confirmation 382 or other data indicating the delivery within a few minutes after data acquisition module 138 obtains such confirmation. This can occur, for example, in a context in which one or more systems 5-9 described above implement primary unit 3610, in which UAD 1005 implements the "first" UAD, and in which sender 510 would otherwise be unwilling to send cargo module 490 via UAD 1005. In the variants set forth above, for example, operation 84 and one or more others of the above-describe extensive operations may be initiated by processor 365 (executing a respective variant of high-level command 485, e.g.) or by invoking special-purpose circuitry as described above.

Referring again to the flow variants of FIGS. 16 and 47-51, other variants of coordinate communication module 136 may perform operation 51—obtaining first position data from a first entity, by a second entity, the first entity being a first unmanned aerial device—by receiving an address 562 from UAD 501 indicating the position of sender 510). This can occur, for example, in a context in which UAD 501 implements UAD 1005 as described above; in which sender 510 is or has the "first" resource (a data handling unit 2078 or other package 2050 or product 2060 described herein, e.g.); and in which such resource(s) may be allocated as described herein (purchased or temporarily reserved by the "second" entity, e.g.). This can occur, for example, in a context in which the second entity (recipient 4650, e.g.) is remote from the location specified by the first position data (not within the same room or facility, e.g.). In the variants set forth above, for example, operation 51 and one or more others of the above-describe intensive operations may be initiated by processor 365 (executing a respective variant of high-level command 484, e.g.) or by invoking special-purpose circuitry as described above.

Other variants of resource reservation module 156 may likewise perform operation 83 of flow 16—signaling a decision whether or not to allocate a first resource to the second entity after the first position data passes from the first unmanned aerial device to the second entity, the first resource being associated with the first position data—by transmitting an indication 2107 that a request 373 for such a resource reservation 376 has been declined. This can occur in a context in which the first resource is offline or otherwise unavailable, for example, or in which no device is authorized to grant a reservation of the first resource. In some contexts, for example, resource reservation module 156 may be configured to manage other resources within a defined zone 781 or of a particular type (products 2060, e.g.). Alternatively or additionally, in some variants, resource reservation module 156 may be configured to provide (automatically and conditionally, e.g.) one or more signals other than whether or not to allocate the first resource ("stand by while I contact an authorized agent for you," e.g.). In the variants set forth above, for example, operation 83 and one or more others of the above-describe extensive operations may be initiated by processor 365 (executing a respective variant of high-level command 485, e.g.) or by invoking special-purpose circuitry as described above.

In light of teachings herein, numerous existing techniques may be applied for configuring special-purpose circuitry or other structures effective for associating a user or a device with another user or another device without undue experimentation or for configuring other decisions and devices as described herein. See, e.g., U.S. Pat. No. 8,023,485 ("Method, system and device for realizing user identity association"); U.S. Pat. No. 7,979,585 ("System and method to associate a private user identity with a public user identity"); U.S. Pat. No. 7,970,660 ("Identifying associations between items and email-address-based user communities"); U.S. Pat. No. 7,941,505 ("System and method for associating a user with a user profile in a computer network environment"); U.S. Pat. No. 7,894,812 ("Automatic over-the-air updating of a preferred roaming list (PRL) in a multi-mode device, based on an account association between the device and a wireless local area network (WLAN) access point"); U.S. Pat. No. 7,743,099 ("Associating multiple visibility profiles with a user of real-time communication system"); U.S. Pat. No. 7,716,378 ("System and method to associate a private user identity with a public user identity"); U.S. Pat. No. 7,703,691 ("Multiple device and/or user association"); U.S. Pat. No. 7,627,577 ("System and method for maintaining an association between a distribution device and a shared end user characteristic"); U.S.

Pat. No. 6,473,824 ("Dynamic association of input/output device with application programs").

Referring again to the flow variants of FIGS. 17 and 47-51, other variants of interface control module 141 may perform operation 52—causing a first unmanned aerial device to guide a first individual to a first destination—by signaling via UAD 1005 a direction 2189 of one or more waypoints 642, 742 relative to a current position of the "first" individual along a path to the first destination. In the context of FIG. 6, for example, an interface control module 141 may be configured to perform operation 52 by prompting UAD 601 (implementing UAD 1005, e.g.) to signal (via a wireless communication linkage 694, e.g.) a direction of a waypoint 642 to guide a driver (by causing user interface 660 to display an upward arrow to user 626, e.g.) along a path 643 to the first destination (parking space 648, e.g.). Another implementation of interface control module 141 may be configured to perform operation 52 by configuring UAD 701 (implementing UAD 1005, e.g.) to signal a direction of a waypoint 742 to guide a pedestrian (via a speaker 1171 or display 1172 aboard UAD 1005, e.g.) along a path 743 (to "first" destination 530, e.g.). In relation to these variants and others set forth above, operation 52 and one or more others of the above-describe intensive operations may (optionally) be initiated by processor 365 (executing a respective variant of high-level command 484, e.g.) or by invoking special-purpose circuitry as described above.

Other variants of flight control module 152 may likewise perform operation 85 of flow 17—causing the first unmanned aerial device to fly to a second destination as an automatic and conditional response to an indication of the first individual arriving at the first destination—by causing UAD 1005 to fly to the "second" destination after, and responsive to, the "first" individual apparently arriving at a parking space 648 or other "first" destination 530). This can occur, for example, in a context in which the "second" destination relates to a task 491-499 to be performed next; in which one or more other conditions, events, or indications 2101-2109 described herein also occur (detected by event/condition detection logic 1410 or signaled by one or more triggers 2111-2120, e.g.); and in which flight control module 152 implements such flight by triggering a task implementation module 1485 aboard UAD 1005 to activate one or more motors 1081-1083 aboard UAD 1005 controlling one or more props 1071-1073 aboard UAD 1005. In the variants set forth above, for example, operation 85 and one or more others of the above-describe extensive operations may be initiated by processor 365 (executing a respective variant of high-level command 485, e.g.) or by invoking special-purpose circuitry as described above.

Referring again to the flow variants of FIGS. 18 and 47-51, other variants of enlistment module 133 may perform operation 54—indicating a first unmanned aerial device participating in a first task—by notifying device operators (e.g. users 226, 626) or other persons 725, 726 that a "first" task 491-499 (or component task thereof) as described herein has been begun by or accepted on behalf of "first" UAD 1005. This can occur, for example, in a context in which network 190 contains UAD 1005 and in which primary unit 3610 contains interface device 310 and event/condition detection unit 400. In the variants set forth above, for example, operation 54 and one or more others of the above-describe intensive operations may be initiated by processor 365 (executing a respective variant of high-level command 484, e.g.) or by invoking special-purpose circuitry as described above.

Other variants of control unit 860 may likewise perform operation 82 of flow 18—signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device—by configuring a name recognition module 147 of control unit 860 to recognize and use the primary identifier 821 of UAD 1005 (instead of an alias, e.g.) partly based on an indication of UAD 1005 participating in a "first" task 491-499 described herein and partly based on an indication that UAD 1005 has not accepted any aliases 822, 823. This can occur, for example, in a context in which the decision is negative (not to cause UAD 1005 to recognize any aliases, e.g.); in which control unit 860 makes the negative decision in response to UAD 1005 not responding to a configuration request within a prescribed interval; in which UAD 1005 implements UAD 802; in which control unit 860 implements primary unit 3610; and in which control unit 860 addresses UAD 1005 during such task(s) using primary identifier 821. Alternatively, in some contexts, UAD 1005 may generate such a negative decision. In the variants set forth above, for example, operation 82 and one or more others of the above-describe extensive operations may be initiated by processor 365 (executing a respective variant of high-level command 485, e.g.) or by invoking special-purpose circuitry as described above.

Referring again to the flow variants of FIGS. 19 and 47-51, other variants of tracking control module 977 may perform operation 55—obtaining a tracking mode of a delivery task of a first unmanned aerial device—by receiving a device-executable command sequence 2125 implementing a user-defined mode 363 of tracking one or more delivery tasks 491, 494 performed or being performed by UAD 1005. This can occur, for example, in a context in which UAD 1005 implements interface device 310 and media 1200, 2100; in which processor 365 executes device-executable command sequence 2125 (e.g. capturing one or more of image data 1241, GPS data 1242, or timing data 1243) periodically or in response to a trigger 2111-2120 described herein. Alternatively or additionally, a one or more user-specified expressions 2122 (expressing rules that incorporate OR, AND, or other logical operators, e.g.) may identify one or more device-detectable indications 2101-2109 that enable or disable such tracking (respectively as a prerequisite or exception, e.g.). In the variants set forth above, for example, operation 55 and one or more others of the above-describe intensive operations may be initiated by processor 365 (executing a respective variant of high-level command 484, e.g.) or by invoking special-purpose circuitry as described above.

Other variants of selective retention module 158 may likewise perform operation 81 of flow 19—signaling a decision whether or not to omit a record of the first unmanned aerial device completing the delivery task of the first unmanned aerial device as an automatic and conditional response to the tracking mode of the delivery task of the first unmanned aerial device—by transmitting a selection of records 961-964 that are recognized by one or more gesture detection modules 1402, spoken expression detection modules 1403, optical condition detection modules 1404, or other pattern recognition modules 1421-1423 configured to detect one or more events 1412-1414 (a gesture or word or other expression of acknowledgment from a delivery recipient 4650, e.g.) specified by the tracking mode (and detectable as visual or auditory phenomena in one or more records 961-964, e.g.). This can occur, for example, in a context in which a sender 510 of an item delivered decides to specify what kind(s) of expression (saying "take my picture," e.g.) should trigger tracking; in which the sender 510 expresses such decision(s) as the tracking mode 982; and in which the first UAD 1005 would not otherwise perform any tracking upon completion of one or more delivery tasks 491, 494. In the variants set forth above, for example, operation 81 and one or more others of the above-describe extensive operations may be initiated by processor 365 (executing a respective variant of high-level command 485, e.g.) or by invoking special-purpose circuitry as described above.

Referring again to flows 15-19 and to variants thereof described with reference to FIGS. 47-51, in some implementations, each of these flows may (optionally) be performed entirely within a "first" unmanned aerial device (in UAD 1005, e.g.) or within another device described herein. In some implementations, for example, each of these flows may be performed entirely within a vehicle as described herein (car 602, e.g.) or within a single handheld device (e.g. a cell phone or handheld UAD 202, 701) or in a wearable article (an earpiece 4661, wristband 4663, or similar chip-containing device, for example, or an article of clothing 728 having such a device affixed thereto). Alternatively or additionally, the first unmanned aerial device may include the second aerial device (as a cargo module 2090 thereof, e.g.). In some embodiments, moreover, each of these flows may be performed by a network 1090 of devices or otherwise shared among two or more such devices 1010.

Referring again to the flow variants of FIGS. 38 & 47-51, operation 64—obtaining a descriptor of a first entity operating a first unmanned aerial device—may also be performed by pattern recognition module 3639. Such performance may include generating a null or default name 2241 ("guest" or "anonymous," e.g.) initially in response to proximity detection module 3721 detecting a "first" UAD 1005 about which no operatorship information has yet been acquired. Alternatively or additionally, pattern recognition module 3639 may perform operation 64 by reading a barcode 2271 or other device-readable name 2242 from an external label 2275 affixed to UAD 1005. Alternatively or additionally, such a descriptor 2254 may comprise a passive RFID tag 2267 or other device-readable data-handling medium 2200 comprising descriptors 2250 as described herein.

Also in such variants, operation 67—obtaining an operatorship criterion—may be performed by pattern recognition module 3637. Such performance may include accepting a criterion 2394 (implemented in an instance of code 2463 executable by processor 3565, e.g.) that is satisfied for any descriptor that is defined and not blank. This can occur, for example, in a context in which stationary structure 2750 includes primary unit 3610; in which pattern recognition module 3637 is invoked whenever operation 64 occurs or whenever UAD 1005 crosses a boundary (a perimeter of parcel 2840 or entryway threshold, e.g.); and in which primary unit 3610 is configured to control a second entity as described herein.

Also in such variants, operation 72—signaling a decision whether or not to impede the first unmanned aerial device entering a particular region as an automatic and conditional result of applying the operatorship criterion to the descriptor of the first entity operating the first unmanned aerial device—may be performed by decision module 3673. Such performance may include manifesting a decision 3543 to cause a second entity (an actuator 2710 or UAD 803, e.g.) to allow the "first" UAD 1005 to approach something (by entering a room or vicinity 785, e.g.) if any descriptors 2250 of UAD 1005 satisfy one or more operatorship criteria 2392-2396 obtained in operation 67 and in which such a second entity otherwise does nothing (passively impeding the "first" UAD 1005 entering the region, e.g.). This can occur, for example, in a context in which a person 725 (an administrator or owner of a region or such a second entity, e.g.) selects or otherwise defines such operatorship criteria 2392-2396. Alternatively or additionally, decision module 3673 may perform operation 72 by transmitting a message 2357 ("exit eastward immediately" or a similar warning, e.g.) to UAD 1005 or by disabling UAD 1005 (by targeting UAD 1005 with an adhesive 2681, bullet or other missile 2682, incendiary, entanglement line 2683 extended by a grappling hook or similar weight 2684, or other such disablement device 2690, e.g.).

Referring again to the flow variants of FIGS. 39 & 47-51, operation 63—detecting a first unmanned aerial device being within a vicinity of a portal—may also be performed by proximity detection module 3722. Such performance may include a secondary unit 3750 on or in a building 945, 2745 having a portal (aperture 2741, e.g.) detecting that UAD 1005 is within a proximity of the portal. Alternatively or additionally, an instance of detection module 3722 aboard UAD 1005 may likewise perform operation 63 by determining that UAD 1005 is within a proximity (a line of sight or predetermined distance 2239, e.g.) of such a portal.

Also in such variants, operation 61—obtaining an indication of an identity of the first unmanned aerial device—may be performed by signal detection module 3682 receiving a model 352 or operatorship identifier 2866 that indicates an identity of UAD 1005. This can occur, for example, in a context in which primary unit 3610 includes interface device 310 and interacts with secondary unit 3750 and in which interface device 310 controls or comprises UAD 1005. In some variants, for example, UAD 1005 may implement UAD 2801. Alternatively or additionally, in some contexts, operation 61 may be performed before or concurrently with operation 63.

Also in such variants, operation 75—signaling a decision whether or not to allow an actuator to obstruct the portal partly based on the indication of the identity of the first unmanned aerial device and partly based on the first unmanned aerial device being within the vicinity of the portal—may be performed by task implementation module 3752. Such performance may, in some variants, include triggering an opening of door 2742 (so that it will not obstruct aperture 2741 and) so that UAD 1005 can enter aperture 2741. This can occur, for example, in a context in which secondary unit 3750 is mounted on building 2745 or near aperture 2741 and configured so that proximity detection module 3722 and signal detection module 3722 are both operably coupled with task implementation module 3752. Alternatively or additionally, secondary unit 3750 may (optionally) be configured to communicate with UAD 1005 such as by confirming the identity (a street address 2235, e.g.) of building 2745 or by transmitting an authorization 2358 to enter.

Referring again to the flow variants of FIGS. 40 & 47-51, operation 66—obtaining first data including optical data from a vicinity of a reference surface in contact with a first unmanned aerial device—may also be performed by a camera 2541 or other sensors 2560. In some contexts, such performance may include camera 2541 capturing image 2373 (as the optical data that is a component of the "first" data 2321, e.g.) while aboard a "first" UAD 1005 resting upon a landing station 950 or other suitable mooring site (platform 2725, e.g.). This can occur, for example, in a context in which UAD 1005 includes (an instance of) detection unit 2500 and medium 2300; in which part of the "first" data 2321 is obtained via a data handling unit 2078, 3550 aboard "first" UAD 1005; in which another part of the "first" data 2321 is obtained via a stationary sensor 3552, 3115 (of stationary structure 2750, e.g.); in which stationary structure 2750 comprises building 955; and in which detection unit 2500 can operate while UAD 1005 rests upon the reference surface. In some contexts, UAD 1005 may implement a UAD 3005 having electrical contacts 3141 (on respective arms 3151 thereof, e.g.) by which a primary energy source 1022 of UAD 3005 (battery 2085, e.g.) can recharge. Alternatively or additionally, the reference surface(s) may be part of a structure (comprising a combination of base 3010 and wall 3020, e.g.) that includes a stationary power source (an outlet 3019 or inductive charging coil 3122, e.g.). In some contexts, for example, a body 3190 of UAD 3005 may contain a coil (not shown) that UAD 3005 can align with inductive charging coil 3122 for contactless charging of UAD 3005 (implementing UAD 1005, e.g.).

Also in such variants, operation 77—signaling a decision as an automatic and conditional response to the application of a first recognition criterion to the optical data from the vicinity of the reference surface in contact with the first unmanned aerial device whether or not to cause the first unmanned aerial device to be disengaged from the reference surface—may be performed by decision module 3676. In some contexts, such performance may include generating such a decision 3547 to cause the "first" UAD 1005 to remain in contact with the reference surface if no anomalous event 1412-1414 is detected. This can occur, for example, in a context in which one or more of gesture detection module 1402, spoken expression module 1403, or optical condition detection module 1404 are configured to disable decision module 3676 (operably coupled by a wire or other signal path therebetween, e.g.) from generating such a decision 3547 to maintain contact (in response to an anomalous event 1412-1414, e.g.) and in which UAD 1005 is configured to perform a surveillance task 3094 (passing between stations 520, 930 or traversing a patrol route 2878, e.g.) in response to an anomalous event 1412-1414 or condition (detected by event/condition detection logic 1410, e.g.) during an interval 2341 that is expected to be uneventful (at night or on a weekend, e.g.). Alternatively or additionally, decision module 3676 may be configured to cause UAD 1005 to begin such a surveillance task in response to an expiration of a countdown timer 2523 initiated with a timer value 2311 provided by a pseudorandom number generator 3570). This can occur, for example, in a context in which the surveillance behavior of UAD 1005 might otherwise be easy for an adversary to monitor, characterize, predict, and circumvent.

Also in such variants, operation 78—signaling a decision as an automatic and conditional response to the application of the first recognition criterion to the optical data from the vicinity of the reference surface whether or not to cause the first unmanned aerial device to obtain second data with the first unmanned aerial device disengaged from the reference surface—may be performed by task implementation module 3751. In some contexts, such performance may include obtaining additional data (the "second" data 2322, e.g.) via the "first" UAD 1005 in the same manner as the "first" data 2321 was obtained. This can occur, for example, in a context in which UAD 1005 is configured to include a camera 2541 or other sensors 2560 and in which task implementation module 3751 performs operation 78 as a consequence of the same circumstance (result 2451 or decision 3547, e.g.) that caused or resulted from operation 77. In other contexts, however, task implementation module 3751 may be configured not to obtain or retain the "second" data 2322 unless one or more additional criteria 2398, 2399 are met. In some variants, for example, task implementation module 3751 may be configured to signal a decision 3540 not to configure UAD 1005 to capture any "second" data 2322 unless a predetermined criterion 2398 is met (an indication 2403 of UAD 1005 having received one or more triggers 2111-2119 described herein, e.g.). Alternatively or additionally, in some variants, task implementation module 3751 may be configured to signal a decision 3540 not to configure UAD 1005 to retain "second" data 2322 unless another predetermined criterion 2399 is met (an indication 2404 of one or more particular tasks 491-499 having been performed, e.g.).

Referring again to the flow variants of FIGS. 41 & 47-51, operation 59—obtaining operator input from an operator of a first unmanned aerial device as an earlier input component—may also be performed by data aggregation module 3792. This can occur, for example, in a context in which UAD 1005 is the "first" UAD, in which operator interface 3712 receives thresholds 2331, pattern matching criteria 2397, or other such operating parameters 2126-2128 as the earlier input component (a gesture or other input 3583, e.g.) from operator 729 and in which a pattern recognition module 3638 (of event/condition detection logic 1410, e.g.) distills such input 3583 (as a Boolean value 2312 indicating whether or not an anomaly 2315 is recognized, e.g.) from raw data 2326 (audio or video data, e.g.).

Also in such variants, operation 56—obtaining environmental sensor input from a vicinity of the first unmanned aerial device as a later input component—may be performed by microphones 2552 or other sensors 2560 in a proximity 3155 of the "first" UAD 1005. This can occur, for example, in a context in which the resulting environmental sensor input 3585 includes audio data 2323 within which a recognizable pattern 3591 (signifying a gunshot, footstep, fire alarm, human voice, or other such device-detectable phenomenon 2354, e.g.) can be found (by pattern recognition module 3630, e.g.). In some places at some times (within a jewelry store at night, e.g.), the apparent occurrence of such phenomena warrants that the UAD be launched without any (further) operator involvement. Alternatively or additionally, pattern 3591 may require one or more other specific sensor inputs 3581 (indications of abnormal environmental conditions in a vicinity of UAD 1005 from another sensor 2560 that performs operation 56, e.g.).

Likewise in such variants, operation 71—signaling a decision without regard to any other operator input whether or not to launch the first unmanned aerial device partly based on the operator input from the operator of the first unmanned aerial device obtained as the earlier input component and partly based on the environmental sensor input from the vicinity of the first unmanned aerial device obtained as the later input component—may be performed by decision module 3672. Such performance may include transmitting an affirmative decision 3544 to launch the "first" UAD 1005 if and when pattern recognition module 3630 detects a phenomenon 2354 (inferred from sensor data, e.g.), for example, and otherwise generally not transmitting such decision 3544. In some variants, moreover, UAD 1005 may be configured to investigate the premises (a building or parcel 2840 of land or patrol route 2878, e.g.) and transmit other sensor data 2327 (images 2161-2165, e.g.) therefrom as a programmatic and conditional response to such decision 3544.

Referring again to the flow variants of FIGS. 42 & 47-51, operation 58—obtaining first data including an X-ordinate of a first location and a Y-ordinate of the first location indicating a first entity moving from the first location to a second location—may also be performed by location detection module 3641 generating or receiving position data 3483 that signals position 3343 and an indication 2406 of entity 3301 moving downward). This can occur, for example, in a context in which position 3343 is the "first" location; in which the "first" entity 3301 comprises UAD 1005 or another mobile device 1010 described herein; in which the position data 3483 includes an instance of X-ordinate 2231 (horizontal offset, e.g.) and Y-ordinate 2232 (altitude, e.g.); in which indication 2406 signals a particular location (position 3346, e.g.) or heading or general direction of travel (downward, e.g.); and in which one or more media 2200, 2400 reside in primary unit 3610.

Also in such variants, operation 60—obtaining second data indicative of a device-detectable energy signature path having existed between a second entity and the first location—may be performed by pattern recognition module 3633 selectively and automatically recognizing one or more distinctive attributes (a sequence 2121 or other device-detectable pattern 3592, 3593 of frequency or shape components, e.g.) reflected or transmitted by an entity 3302 (comprising a UAD 803 or tower 2730, e.g.). This can occur, for example, in a context in which entity 3301 travels along a path 3370 via position 3343 and position 3345 and in which entity 3301 includes a lower-frequency sensor 3551 and a higher-frequency sensor 3553 of which at least one can detect an audible signal 2421, visible shape, or other distinctive pattern 3593 (along path 3373, e.g.) at the "first" location (position 3343, e.g.) that would not be detectable at the "second" location due to a signal-blocking obstruction 3338 (a bridge, e.g.) between entity 3302 and the "second" location (position 3345, e.g.). In some variants, for example, the lower-frequency sensor 3551 (an auditory or vibration sensor, e.g.) may have a nominal frequency range 2435 that is entirely lower than a nominal frequency range 2445 of the higher-frequency sensor 3553 such that the nominal maximum threshold 2432 of the former is less than half of the nominal minimum threshold 2441 of the latter. Alternatively or additionally, data handling unit 3550 may reside within entity 3301 or in a stationary structure 2750 (tower 2730, e.g.) nearby.

Also in such variants, operation 62—obtaining third data indicative of no device-detectable energy signature path having existed between the second entity and the second location—may be performed by pattern recognition module 3636 determining that a distinctive visible or other pattern 3593 was apparently not received when entity 3301 was at the "second" location at position 3345. This can occur in a context in which an obstruction 3338 blocks a view of entity 3302, for example, such that no device-detectable energy signature path apparently existed between the entity 3302 and the "second" location.

Also in such variants, operation 76—causing the first entity to travel from a third location toward the first location partly based on the X-ordinate and partly based on the Y-ordinate and partly based on the second data indicative of the device-detectable energy signature path having existed between the second entity and the first location and partly based on the third data indicative of no device-detectable energy signature path having existed between the second entity and the second location—may be performed by flight control module 3653 causing entity 3301 (implementing UAD 1005, e.g.) to travel from a vicinity of position 3347 back up (toward position 3341, e.g.) partly based on the "second" and "third" data respectively indicating that "first" entity 3301 could detect "second" entity from the "first" location but not from the "second" location. This can occur in a context in which primary unit 3610 resides in entity 3301, for example, or in stationary structure 2750.

Referring again to the flow variants of FIGS. 43 & 47-51, operation 68—obtaining an indication of a first time interval from when a device-detectable energy signature path existed between a first entity and a second entity until a reference time—may also be performed by a countdown timer 2521 given an initial positive value 2313 that effectively defines how long "first" entity 3301 can remain in positions 3342, 3346 that are apparently not observable (from the vantage of "second" entity 3302, e.g.) without switching navigation protocols. This can occur, for example, in a context in which "first" entity 3301 comprises (an instance of) primary unit 3610 and medium 2300; in which entity 3301 implements a dirigible 1003 or other unmanned aerial device 1005; and in which an initial navigation protocol 3531 of entity 3301 comprises being controlled by an interface device 310 (held by a particular user 226, e.g.).

Also in such variants, operation 73—signaling a decision whether or not to change an aerial navigation protocol of the first entity as an automatic and conditional response to a result of comparing a threshold against the indication of the first time interval from when the device-detectable energy signature path existed between the first entity and the second entity until the reference time—may be performed by navigation module 3662. Such performance may include keeping "first" entity 3301 on protocol 3531 as an automatic and conditional response to countdown timer 2521 remaining positive. Such performance may likewise include implementing a decision 3548 to reset countdown timer 2521 (to initial value 2313, e.g.) as a conditional response to a device-detectable energy signature path 3371 being detected before countdown timer 2521 reaches zero. Alternatively or additionally, such decision 3548 may (optionally) result in protocol 3532 (autopilot, e.g.) or protocol 3533 (control by an operator 729 via data handling unit 3550, e.g.) being implemented as an automatic and conditional response to navigation module 3662 detecting a device-detectable energy signature path (between the first and second entities 3301, 3302, e.g.) before countdown timer 2521 reaches zero.

Referring again to the flow variants of FIGS. 44 & 47-51, operation 57—obtaining photographic data depicting a first unmanned aerial device—may also be performed by signal detection module 3685. Such performance may include receiving a wireless signal 2428 containing one or more images 2375 of UAD 1005 (from a charge-coupled device 1493 or camera 2918, e.g.). This can occur, for example, in a context in which primary unit 3610 is configured to receive such signals via a wireless linkage 3694 from an article 1400 that includes storage or transmission media 2300, 2400 (a server in network 3690 operably coupled to a tower 2730, e.g.). In some contexts, for example, such an article 1400 may include or otherwise interact with camera 2918. Alternatively or additionally, such photographic data may include a result 2453 ("not found," e.g.) of data distillation module 3781 implementing a pattern recognition protocol upon such images (trying to recognize one or more barcodes 2271, 2961 or other shape pattern occurrences therein, e.g.).

Also in such variants, operation 65—obtaining an indication whether or not the first unmanned aerial device behaved anomalously—may be performed by pattern recognition module 3634. Such performance may include generating an indication 2408 whether or not UAD 1005 apparently transmitted any data outside a specified frequency range 2435 while within zone 781. This can occur, for example, in a context in which an operator 729 of UAD 1005 has been provided an assurance or has been notified of a requirement that UAD 1005 will only transmit within range 2435 while within zone 781 and in which use of other frequency ranges 2445 by UAD 1005 may interfere with other operations within zone 781 or may signal that UAD 1005 is untrustworthy. Alternatively or additionally, in some variants of pattern recognition module 3634, one or more such indications 2408 may signal whether UAD 1005 has apparently complied with one or more other use restriction definitions 2471-2475 applicable to UAD 1005.

Alternatively or additionally, in some contexts, a data distillation module 3784 may be configured to perform operation 65 by selectively generating a result 2452 of comparing one or more tasks 491-499 apparently being performed by UAD 1005 against a task list 2463 (of zero or more tasks) that the first unmanned aerial device normally or permissibly performs as the indication whether or not the first unmanned aerial device behaved anomalously. Alternatively or additionally, data distillation module 3784 may be configured to condition such result 2452 upon whether an identifier 543 of UAD 1005 (implementing UAD 501, e.g.) appears in an entity list 2464 (of zero or more entities) identifying any entities that are normally or permissibly present or performing such task(s) within a specific zone 781 (on a premises or within a vicinity of destination 530, e.g.).

Also in such variants, operation 74—signaling a decision whether or not to transmit the photographic data depicting the first unmanned aerial device as an automatic and conditional response to the indication whether or not the first unmanned aerial device behaved anomalously—may be performed by data distillation module 3782. Such performance may include discarding one or more images 2375 of UAD 1005 at least partly based on an indication 2408 (from pattern recognition module 3634 or data distillation module 3784, e.g.) that UAD 1005 apparently complied with any applicable requirements of use restriction definitions 2471-2475 pertaining to UAD 1005 within zone 781. In some contexts, for example, data distillation module 3782 may perform operation 74 by transmitting anomaly-indicative images 2376 at a higher sampling rate (more than 50%, e.g.) than a nominal sampling rate (of less than 50%, e.g.) of normalcy-indicative images 2377. This can occur, for example, in a context in which pattern recognition module 3634 sometimes fails to detect latent anomalies 2315 (an instance of UAD 1005 causing an injury or participating in an identity theft or other crime, e.g.) among images 2375 initially designated as normalcy-indicative images 2377 and in which such erroneously-designated normalcy-indicative images 2377 may be used (by a computer programmer, e.g.) in refining pattern recognition module 3634. Alternatively or additionally, data distillation module 3782 may be configured to condition such a decision 3672 (whether or not to transmit the photographic data, e.g.) upon whether one or more pattern recognition modules 3635 have identified the UAD 1005.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof, limited to patentable subject matter under 35 U.S.C. 101.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C. 101. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B" in respective included configurations.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

CLAUSES

1. A system comprising:
   one or more articles of manufacture including
   circuitry for obtaining photographic data depicting a first unmanned aerial device;
   circuitry for obtaining an indication whether or not the first unmanned aerial device behaved anomalously; and
   circuitry for signaling a decision whether or not to transmit the photographic data depicting the first unmanned aerial device as an automatic and conditional response to the indication whether or not the first unmanned aerial device behaved anomalously.
2. The system of any of the above SYSTEM CLAUSES in which the circuitry for obtaining an indication whether or not the first unmanned aerial device behaved anomalously comprises:
   circuitry for obtaining an indication that the first unmanned aerial device is performing a particular task; and
   circuitry for selectively generating a result of comparing the particular task against a task list of one or more tasks that the first unmanned aerial device performs as the indication whether or not the first unmanned aerial device behaved anomalously.
3. The system of any of the above SYSTEM CLAUSES in which the circuitry for obtaining an indication whether or not the first unmanned aerial device behaved anomalously comprises:
   circuitry for obtaining an indication that the first unmanned aerial device is in a specific zone; and
   circuitry for selectively generating a result of comparing an identifier of the first unmanned aerial device against an entity list identifying one or more entities that are normally in the specific zone as the indication whether or not the first unmanned aerial device behaved anomalously.
4. The system of any of the above SYSTEM CLAUSES in which the circuitry for signaling a decision whether or not to transmit the photographic data depicting the first unmanned aerial device as an automatic and conditional response to the indication whether or not the first unmanned aerial device behaved anomalously comprises:
   circuitry for transmitting the photographic data depicting the first unmanned aerial device selectively in response to an indication that the first unmanned aerial device has not been identified.
5. The system of any of the above SYSTEM CLAUSES in which the circuitry for signaling a decision whether or not to transmit the photographic data depicting the first unmanned aerial device as an automatic and conditional response to the indication whether or not the first unmanned aerial device behaved anomalously comprises:
   circuitry for transmitting the photographic data depicting the first unmanned aerial device selectively in response to an indication that the first unmanned aerial device behaved anomalously and otherwise generally not transmitting the photographic data.
6. The system of any of the above SYSTEM CLAUSES in which the one or more articles of manufacture further comprise:
   circuitry for configuring a second unmanned aerial device to perform a first observation of the first unmanned aerial device in a first zone and a third unmanned aerial device to perform a second observation of the first unmanned aerial device in a second zone.
7. The system of any of the above SYSTEM CLAUSES in which the one or more articles of manufacture comprise:
   a handheld device, including the circuitry for obtaining the photographic data depicting the first unmanned aerial device and including the circuitry for obtaining the indication whether or not the first unmanned aerial device behaved anomalously and including the circuitry for signaling the decision whether or not to transmit the photographic data depicting the first unmanned aerial device as the automatic and conditional response to the indication whether or not the first unmanned aerial device behaved anomalously.
8. The system of any of the above SYSTEM CLAUSES in which the one or more articles of manufacture comprise:
   a wearable device, including the circuitry for obtaining the photographic data depicting the first unmanned aerial device and including the circuitry for obtaining the indication whether or not the first unmanned aerial device behaved anomalously and including the circuitry for signaling the decision whether or not to transmit the photographic data depicting the first unmanned aerial device as the automatic and conditional response to the indication whether or not the first unmanned aerial device behaved anomalously.
9. The system of any of the above SYSTEM CLAUSES in which the one or more articles of manufacture further comprise:
   a vehicle having one or more wheels, the vehicle configured to support the circuitry for obtaining the photographic data depicting the first unmanned aerial device and to support the circuitry for obtaining the indication whether or not the first unmanned aerial device behaved anomalously and to support the circuitry for signaling the decision whether or not to transmit the photographic data depicting the first unmanned aerial device as the automatic and conditional response to the indication whether or not the first unmanned aerial device behaved anomalously.

10. The system of any of the above SYSTEM CLAUSES in which the one or more articles of manufacture comprise:

a second unmanned aerial device having one or more propellers and configured to support the circuitry for obtaining the photographic data depicting the first unmanned aerial device and to support the circuitry for obtaining the indication whether or not the first unmanned aerial device behaved anomalously and to support the circuitry for signaling the decision whether or not to transmit the photographic data depicting the first unmanned aerial device as the automatic and conditional response to the indication whether or not the first unmanned aerial device behaved anomalously.

11. The system of any of the above SYSTEM CLAUSES in which the one or more articles of manufacture comprise:

a second unmanned aerial device including the circuitry for obtaining the photographic data depicting the first unmanned aerial device and including the circuitry for obtaining the indication whether or not the first unmanned aerial device behaved anomalously and including the circuitry for signaling the decision whether or not to transmit the photographic data depicting the first unmanned aerial device as the automatic and conditional response to the indication whether or not the first unmanned aerial device behaved anomalously.

12. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously.

13. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously; and circuitry for configuring the second unmanned aerial device to capture normalcy-indicative data relating to a human subject.

14. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously; and circuitry for causing the second unmanned aerial device to undertake a performance observation task of a job that includes a performance task and the performance observation task.

15. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously; and circuitry for configuring the second unmanned aerial device to transmit a wireless signal indicative of having performed a particular task and not to store any indication of having performed the particular task.

16. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for transmitting a wireless signal indicative of a delivery of a package to a device associated with a recipient of the package, the wireless signal indicating at least one of the second unmanned aerial device or the package or a sender of the package.

17. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously; and circuitry for signaling a decision whether or not to reserve a space for a passenger vehicle.

18. The system of any of the above SYSTEM CLAUSES in which the one or more articles of manufacture further comprise:

a second unmanned aerial device including the circuitry for signaling the decision whether or not to transmit the photographic data depicting the first unmanned aerial device as the automatic and conditional response to the indication whether or not the first unmanned aerial device behaved anomalously; and circuitry for signaling a decision whether or not to reserve a specific resource by associating the specific resource with a specific device or with a specific person.

19. The system of any of the above SYSTEM CLAUSES in which the one or more articles of manufacture comprise:

a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for responding to an indication of the second unmanned aerial device becoming within a proximity of the first unmanned aerial device.

20. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for presenting navigation guidance via a display aboard the second unmanned aerial device while a primary motor of the second unmanned aerial device is not moving the second unmanned aerial device.

21. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for transmitting navigation guidance via a speaker of the second unmanned aerial device while a primary motor of the second unmanned aerial device is not moving the second unmanned aerial device.

22. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for identifying an operating mode of the second unmanned aerial device audibly or visibly while a primary motor of the second unmanned aerial device is not moving the second unmanned aerial device.

23. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for causing a modular observation unit to be lifted and activated within at most about an hour of the modular observation unit becoming part of the second unmanned aerial device.

24. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for signaling a decision whether or not to configure the second unmanned aerial device to continue observing a first person responsive to a prior observation of the first person.

25. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for causing a third unmanned aerial device to capture delivery data relating to the second unmanned aerial device.

26. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for configuring the second unmanned aerial device not to be equipped with any light sensors.

27. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for causing a data handling device aboard the second unmanned aerial device to contain a task schedule indicating a first future delivery of a first object to a first destination and a second future delivery of a second object to a second destination.

28. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for causing the second unmanned aerial device to execute a delivery of a single dose of a therapeutic material to a human hand within one minute of an image capture of a portion of the human hand.

29. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for causing the second unmanned aerial device to execute a delivery of a particular object to a human recipient contemporaneously with an image capture of a portion of the human recipient.

30. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for determining whether or not an operator of the second unmanned aerial device has indicated a tracking mode of the second unmanned aerial device.

31. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for overriding a first task being performed by the second unmanned aerial device by transmitting a wireless signal indicative of a second task to the second unmanned aerial device.

32. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously; and
circuitry for causing the second unmanned aerial device to fly toward a home station in response to an indication of a specific person moving at least a threshold distance away from the second unmanned aerial device.

33. The system of any of the above SYSTEM CLAUSES in which the one or more articles of manufacture comprise:
a second unmanned aerial device including the circuitry for signaling the decision whether or not to transmit the photographic data depicting the first unmanned aerial device as the automatic and conditional response to the indication whether or not the first unmanned aerial device behaved anomalously, the second unmanned aerial device including circuitry for responding to a determination of whether or not a received signal expresses a first name of the second unmanned aerial device and whether or not the received signal expresses a second name of the second unmanned aerial device.

All of the patents and other publications referred to above (not including websites) are incorporated herein by reference generally—including those identified in relation to particular new applications of existing techniques—to the extent not inconsistent herewith. While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A system comprising:
electronic circuitry configured for capturing, via at least one imaging device, imaging data depicting the at least one unmanned aerial device;
electronic circuitry configured for analyzing the imaging data depicting the at least one unmanned aerial device via pattern recognition including at least determining at least one behavior of the at least one unmanned aerial device based at least partly on analysis of the imaging data depicting the at least one unmanned aerial device;
electronic circuitry configured for determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; and
electronic circuitry configured for triggering transmission of the captured imaging data depicting the at least one unmanned aerial device responsive to a determination that the at least one behavior of the at least one unmanned aerial device deviates from the one or more use restrictions.

2. A system comprising:
at least one computing device; and
one or more instructions that, when implemented in the at least one computing device, configure the at least one computing device for:
capturing, via at least one imaging device, imaging data depicting the at least one unmanned aerial device;
analyzing the imaging data depicting the at least one unmanned aerial device via pattern recognition including at least determining at least one behavior of the at least one unmanned aerial device based at least partly on analysis of the imaging data depicting the at least one unmanned aerial device;
determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; and
triggering transmission of the captured imaging data depicting the at least one unmanned aerial device responsive to a determination that the at least one behavior of the at least one unmanned aerial device deviates from the one or more use restrictions.

3. The system of claim 2 in which the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors comprises:
- obtaining an indication that the at least one unmanned aerial device is performing a particular task; and
- comparing the particular task against a task list of one or more permitted tasks for the at least one unmanned aerial device.

4. The system of claim 2 in which the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors comprises:
- obtaining an indication that the first unmanned aerial device is in a specific zone; and
- comparing an identifier of the at least one unmanned aerial device against an entity list identifying one or more entities that are permitted in the specific zone.

5. The system of claim 2 in which the triggering transmission of the captured imaging data depicting the at least one unmanned aerial device responsive to a determination that the at least one behavior of the at least one unmanned aerial device deviates from the one or more use restrictions comprises:
- triggering transmission of the captured imaging data depicting the at least one unmanned aerial device when an indication that the at least one unmanned aerial device has not been identified is received.

6. The system of claim 2 further comprising one or more instructions that, when implemented in the at least one computing device, configure the at least one computing device for:
- at least one of:
  - configuring a second unmanned aerial device to perform a first observation of the at least one unmanned aerial device in a first zone and configuring a third unmanned aerial device to perform a second observation of the at least one unmanned aerial device in a second zone;
  - configuring the at least one unmanned aerial device to capture data relating to a human subject; or
  - causing the at least one unmanned aerial device to undertake a performance observation task following a performance task.

7. The system of claim 2 further comprising:
a handheld device configured for at least one of the capturing, via at least one imaging device, imaging data depicting the at least one unmanned aerial device; the analyzing the imaging data depicting the at least one unmanned aerial device via pattern recognition including at least determining at least one behavior of the at least one unmanned aerial device based at least partly on analysis of the imaging data depicting the at least one unmanned aerial device; the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; or the triggering transmission of the captured imaging data depicting the at least one unmanned aerial device responsive to a determination that the at least one behavior of the at least one unmanned aerial device deviates from the one or more use restrictions.

8. The system of claim 2 further comprising:
a wearable device configured for at least one of the capturing, via at least one imaging device, imaging data depicting the at least one unmanned aerial device; the analyzing the imaging data depicting the at least one unmanned aerial device via pattern recognition including at least determining at least one behavior of the at least one unmanned aerial device based at least partly on analysis of the imaging data depicting the at least one unmanned aerial device; the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; or the triggering transmission of the captured imaging data depicting the at least one unmanned aerial device responsive to a determination that the at least one behavior of the at least one unmanned aerial device deviates from the one or more use restrictions.

9. The system of claim 2 further comprising:
a second unmanned aerial device configured for at least one of the capturing, via at least one imaging device, imaging data depicting the at least one unmanned aerial device; the analyzing the imaging data depicting the at least one unmanned aerial device via pattern recognition including at least determining at least one behavior of the at least one unmanned aerial device based at least partly on analysis of the imaging data depicting the at least one unmanned aerial device; the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; or the triggering transmission of the captured imaging data depicting the at least one unmanned aerial device responsive to a determination that the at least one behavior of the at least one unmanned aerial device deviates from the one or more use restrictions.

10. The system of claim 2 further comprising:
a second unmanned aerial device configured for the triggering transmission of the captured imaging data depicting the at least one unmanned aerial device responsive to a determination that the at least one behavior of the at least one unmanned aerial device deviates from the one or more use restrictions.

11. The system of claim 2 further comprising a surveillance device configured for at least one of the capturing, via at least one imaging device, imaging data depicting the at least one unmanned aerial device; the analyzing the imaging data depicting the at least one unmanned aerial device via pattern recognition including at least determining at least one behavior of the at least one unmanned aerial device based at least partly on analysis of the imaging data depicting the at least one unmanned aerial device; the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; or the triggering transmission of the captured imaging data depicting the at least one unmanned aerial device responsive to a determination that the at least one behavior of the at least one unmanned aerial device deviates from the one or more use restrictions.

12. The system of claim 2 further comprising:

a network device configured for at least one of the capturing, via at least one imaging device, imaging data depicting the at least one unmanned aerial device; the analyzing the imaging data depicting the at least one unmanned aerial device via pattern recognition including at least determining at least one behavior of the at least one unmanned aerial device based at least partly on analysis of the imaging data depicting the at least one unmanned aerial device; the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; or the triggering transmission of the captured imaging data depicting the at least one unmanned aerial device responsive to a determination that the at least one behavior of the at least one unmanned aerial device deviates from the one or more use restrictions.

13. The system of claim 2 further comprising one or more instructions that, when implemented in the at least one computing device, configure the at least one computing device for:

configuring the at least one unmanned aerial device to transmit a wireless signal indicative of having performed a particular task and not to store any indication of having performed the particular task.

14. The system of claim 2 further comprising one or more instructions that, when implemented in the at least one computing device, configure the at least one computing device for:

transmitting a wireless signal indicative of a delivery of a package to a device associated with a recipient of the package, the wireless signal indicating at least one of the at least one unmanned aerial device or the package or a sender of the package.

15. The system of claim 2 further comprising one or more instructions that, when implemented in the at least one computing device, configure the at least one computing device for:

signaling a decision whether to reserve a specific resource by associating the specific resource with a specific device or with a specific person.

16. The system of claim 2 further comprising one or more instructions that, when implemented in the at least one computing device, configure the at least one computing device for:

responding to an indication of a second unmanned aerial device becoming within a proximity of the first unmanned aerial device.

17. The system of claim 2 further comprising one or more instructions that, when implemented in the at least one computing device, configure the at least one computing device for:

transmitting navigation guidance via a speaker of the at least one unmanned aerial device.

18. The system of claim 2 further comprising one or more instructions that, when implemented in the at least one computing device, configure the at least one computing device for:

identifying an operating mode of the at least one unmanned aerial device audibly or visibly.

19. The system of claim 2 further comprising one or more instructions that, when implemented in the at least one computing device, configure the at least one computing device for:

causing an observation unit to be lifted by the at least one unmanned aerial device and activated within a threshold time period.

20. The system of claim 2 further comprising one or more instructions that, when implemented in the at least one computing device, configure the at least one computing device for:

signaling a decision whether to configure the at least one unmanned aerial device to continue observing a first person responsive to a prior observation of the first person.

21. The system of claim 2 further comprising one or more instructions that, when implemented in the at least one computing device, configure the at least one computing device for:

causing a second unmanned aerial device to capture delivery data relating to the at least one unmanned aerial device.

22. The system of claim 2 further comprising one or more instructions that, when implemented in the at least one computing device, configure the at least one computing device for:

causing a data handling device aboard the at least one unmanned aerial device to contain a task schedule indicating a first future delivery of a first object to a first destination and a second future delivery of a second object to a second destination.

23. The system of claim 2 further comprising one or more instructions that, when implemented in the at least one computing device, configure the at least one computing device for:

causing the at least one unmanned aerial device to execute a delivery of a dose of a therapeutic material to a human subject within a threshold time period following an image capture of at least a portion of the human subject.

24. The system of claim 2 further comprising one or more instructions that, when implemented in the at least one computing device, configure the at least one computing device for:
  causing the at least one unmanned aerial device to execute a delivery of a particular object contemporaneously with an image capture.

25. The system of claim 2 further comprising one or more instructions that, when implemented in the at least one computing device, configure the at least one computing device for:
  determining whether an operator of the at least one unmanned aerial device has indicated a tracking mode of the at least one unmanned aerial device.

26. The system of claim 2 further comprising one or more instructions that, when implemented in the at least one computing device, configure the at least one computing device for:
  overriding a first task being performed by the at least one unmanned aerial device by transmitting a wireless signal indicative of a second task to the at least one unmanned aerial device.

27. The system of claim 2 further comprising one or more instructions that, when implemented in the at least one computing device, configure the at least one computing device for:
  causing the at least one unmanned aerial device to fly toward a home station in response to an indication of a specific person moving at least a threshold distance away from the at least one unmanned aerial device.

28. The system of claim 2 further comprising one or more instructions that, when implemented in the at least one computing device, configure the at least one computing device for:
  responding to a determination of whether a received signal expresses a first name of the at least one unmanned aerial device and whether the received signal expresses a second name of the at least one unmanned aerial device.

29. The system of claim 2 further comprising:
  a vehicle, having one or more wheels, configured for at least one of the capturing, via at least one imaging device, imaging data depicting the at least one unmanned aerial device; the analyzing the imaging data depicting the at least one unmanned aerial device via pattern recognition including at least determining at least one behavior of the at least one unmanned aerial device based at least partly on analysis of the imaging data depicting the at least one unmanned aerial device; the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; or the triggering transmission of the captured imaging data depicting the at least one unmanned aerial device responsive to a determination that the at least one behavior of the at least one unmanned aerial device deviates from the one or more use restrictions.

30. The system of claim 2 further comprising one or more instructions that, when implemented in the at least one computing device, configure the at least one computing device for:
  signaling a decision whether to reserve a space for a passenger vehicle.

31. The system of claim 2 further comprising one or more instructions that, when implemented in the at least one computing device, configure the at least one computing device for:
  presenting navigation guidance via a display aboard the at least one unmanned aerial device.

32. The system of 2, wherein the determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors includes:
  obtaining an indication that the at least one unmanned aerial device deviates from at least one of a proximity restriction definition, a location restriction definition, a temporal restriction definition, an identification restriction definition, or a purpose restriction definition.

33. The system of 2, wherein the capturing, via at least one imaging device, imaging data depicting the at least one unmanned aerial device includes:
  capturing, via the at least one imaging device, imaging data depicting the at least one unmanned aerial device at a first sampling rate; and
  capturing, via the at least one imaging device, imaging data depicting the at least one unmanned aerial device at a second sampling rate responsive to a determination that the at least one behavior of the at least one unmanned aerial device deviates from the one or more use restrictions.

34. A processing device-implemented method comprising:
  capturing, via at least one imaging device, imaging data depicting the at least one unmanned aerial device;
  analyzing the imaging data depicting the at least one unmanned aerial device via pattern recognition including at least determining at least one behavior of the at least one unmanned aerial device based at least partly on analysis of the imaging data depicting the at least one unmanned aerial device;
  determining whether the at least one behavior of the at least one unmanned aerial device deviates from one or more use restrictions including at least determining a location of the at least one unmanned aerial device, obtaining a definition of at least one of permitted behaviors or restricted behaviors at the location of the at least one unmanned aerial device, and classifying the at least one behavior of the at least one unmanned aerial device based at least partly on the definition of at least one of permitted behaviors or restricted behaviors; and
  triggering transmission of the captured imaging data depicting the at least one unmanned aerial device responsive to a determination that the at least one behavior of the at least one unmanned aerial device deviates from the one or more use restrictions.

* * * * *

UNITED STATES PATENT AND TRADEMARK OFFICE
CERTIFICATE OF CORRECTION

PATENT NO. : 9,713,675 B2
APPLICATION NO. : 13/601195
DATED : July 25, 2017
INVENTOR(S) : Royce A. Levien et al.

Page 1 of 1

It is certified that error appears in the above-identified patent and that said Letters Patent is hereby corrected as shown below:

In the Claims

In Column 95, Line 1, Claim 11 "The system of claim 2 further comprising" should be --The system of claim 2 further comprising:--

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*